United States Patent
Friedrich et al.

(10) Patent No.: US 9,913,814 B2
(45) Date of Patent: *Mar. 13, 2018

(54) TAMPER RESISTANT IMMEDIATE RELEASE CAPSULE FORMULATION COMPRISING TAPENTADOL

(71) Applicant: GRÜNENTHAL GMBH, Aachen (DE)

(72) Inventors: Ingo Friedrich, Aachen (DE); Richard Fuhrherr, Wedel (DE); Silke Möschter, Köln (DE); Simone Wengner, Eberbach (DE)

(73) Assignee: GRÜNENTHAL GMBH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/257,972

(22) Filed: Sep. 7, 2016

(65) Prior Publication Data

US 2016/0374965 A1 Dec. 29, 2016

Related U.S. Application Data

(63) Continuation of application No. 14/709,124, filed on May 11, 2015.

(30) Foreign Application Priority Data

May 12, 2014 (EP) .................... 14167923
Jul. 9, 2014 (EP) .................... 14176277

(51) Int. Cl.
A61K 31/137 (2006.01)
A61K 9/48 (2006.01)
A61K 9/00 (2006.01)

(52) U.S. Cl.
CPC .......... *A61K 31/137* (2013.01); *A61K 9/0053* (2013.01); *A61K 9/485* (2013.01); *A61K 9/4808* (2013.01); *A61K 9/4858* (2013.01); *A61K 9/4866* (2013.01)

(58) Field of Classification Search
None
See application file for complete search history.

(56) References Cited

U.S. PATENT DOCUMENTS

| | | |
|---|---|---|
| 2,524,855 A | 10/1950 | Schnider et al. |
| 2,806,033 A | 9/1957 | Lewenstein et al. |
| 2,987,445 A | 6/1961 | Levesque |
| 3,332,950 A | 7/1967 | Blumberg et al. |
| 3,370,035 A | 2/1968 | Ogura et al. |
| 3,652,589 A | 3/1972 | Flick et al. |
| 3,806,603 A | 4/1974 | Gaunt et al. |
| 3,865,108 A | 2/1975 | Hartop |
| 3,941,865 A | 3/1976 | Miller et al. |
| 3,966,747 A | 6/1976 | Monkovic et al. |
| 3,980,766 A | 9/1976 | Shaw et al. |
| 4,002,173 A | 1/1977 | Manning et al. |
| 4,014,965 A | 3/1977 | Stube et al. |
| 4,070,494 A | 1/1978 | Hoffmeister et al. |
| 4,070,497 A | 1/1978 | Wismer et al. |
| 4,175,119 A | 11/1979 | Porter |
| 4,200,704 A | 4/1980 | Stanley et al. |
| 4,207,893 A | 6/1980 | Michaels |
| 4,262,017 A | 4/1981 | Kuipers et al. |
| 4,343,789 A | 8/1982 | Kawata et al. |
| 4,353,887 A | 10/1982 | Hess et al. |
| 4,404,183 A | 9/1983 | Kawata et al. |
| 4,427,681 A | 1/1984 | Munshi et al. |
| 4,427,778 A | 1/1984 | Zabriskie |
| 4,457,933 A | 7/1984 | Gordon et al. |
| 4,462,941 A | 7/1984 | Lee et al. |
| 4,473,640 A | 9/1984 | Combie et al. |
| 4,483,847 A | 11/1984 | Augart |
| 4,485,211 A | 11/1984 | Okamoto |
| 4,529,583 A | 7/1985 | Porter |
| 4,599,342 A | 7/1986 | La Hann |
| 4,603,143 A | 7/1986 | Schmidt |
| 4,612,008 A | 9/1986 | Wong et al. |
| 4,629,621 A | 12/1986 | Snipes |
| 4,667,013 A | 5/1987 | Reichle |
| 4,690,822 A | 9/1987 | Uemura |
| 4,713,243 A | 12/1987 | Schiraldi et al. |
| 4,744,976 A | 5/1988 | Snipes et al. |
| 4,764,378 A | 8/1988 | Keitn et al. |
| 4,765,989 A | 8/1988 | Wong et al. |
| 4,774,074 A | 9/1988 | Snipes |

(Continued)

FOREIGN PATENT DOCUMENTS

| | | |
|---|---|---|
| AR | 046994 A1 | 12/2004 |
| AR | 045353 A1 | 10/2005 |
| AR | 049562 A1 | 8/2006 |
| AR | 053304 A1 | 5/2007 |
| AR | 054222 A1 | 6/2007 |
| AR | 054328 A1 | 6/2007 |
| AU | 769807 B2 | 3/2001 |
| AU | 2003237944 A1 | 12/2003 |
| AU | 2003274071 A1 | 5/2004 |
| AU | 2003278133 A1 | 5/2004 |

(Continued)

OTHER PUBLICATIONS

Alekseeva et al, Chemical-Pharmaceutical Journal, vol. 41, No. 9, 2007, 49-52. (Full translation attached.).
Efentakis et al, Effects of Excipients on Swelling and Drug Release from Compressed Matrices, in Drug Development and Industrial Pharmacy 23(1):107-112, Jan. 1997, Abstract.
Extended European Search Report and Opinion for Application No. EP 15184634.2-1455, dated Mar. 3, 2016.
Linz et al. "Cebranopadol: A Novel Potent Analgesic Nociception/Orphanin FQ Peptide and Opioid Receptor Agonist," J Pharmacol. Exp. Ther. 2014; 349: 535-548; available online Apr. 8, 2014.

(Continued)

*Primary Examiner* — Brian Gulledge
(74) *Attorney, Agent, or Firm* — Norris McLaughlin & Marcus, P.A.

(57) ABSTRACT

The invention is directed to an immediate release capsule which mitigates the abuse of Tapentadol or physiologically acceptable salt thereof by direct intravenous injection. The capsule comprises a tamper resistant formulation which when mixed with water and heated, results in a turbid, bubbling mixture that is not injectable with a standard insulin syringe.

13 Claims, No Drawings

(56) References Cited

U.S. PATENT DOCUMENTS

| | | |
|---|---|---|
| 4,774,092 A | 9/1988 | Hamilton |
| 4,783,337 A | 11/1988 | Wong et al. |
| 4,806,337 A | 2/1989 | Snipes et al. |
| RE33,093 E | 10/1989 | Schiraldi et al. |
| 4,880,585 A | 11/1989 | Klimesch et al. |
| 4,892,778 A | 1/1990 | Theeuwes et al. |
| 4,892,889 A | 1/1990 | Kirk |
| 4,940,556 A | 7/1990 | MacFarlane et al. |
| 4,954,346 A | 9/1990 | Sparta et al. |
| 4,957,668 A | 9/1990 | Plackard et al. |
| 4,957,681 A | 9/1990 | Klimesch et al. |
| 4,960,814 A | 10/1990 | Wu et al. |
| 4,992,278 A | 2/1991 | Khanna |
| 4,992,279 A | 2/1991 | Palmer et al. |
| 5,004,601 A | 4/1991 | Snipes |
| 5,051,261 A | 9/1991 | McGinty |
| 5,073,379 A | 12/1991 | Klimesch et al. |
| 5,082,668 A | 1/1992 | Wong et al. |
| 5,126,151 A | 6/1992 | Bodor et al. |
| 5,139,790 A | 8/1992 | Snipes |
| 5,145,944 A | 9/1992 | Steinmann |
| 5,149,538 A | 9/1992 | Granger et al. |
| 5,169,645 A | 12/1992 | Shukla et al. |
| 5,190,760 A | 3/1993 | Baker |
| 5,198,226 A | 3/1993 | MacFarlane et al. |
| 5,200,197 A | 4/1993 | Wright et al. |
| 5,211,892 A | 5/1993 | Gueret |
| 5,225,417 A | 7/1993 | Dappen |
| 5,227,157 A | 7/1993 | McGinity et al. |
| 5,229,164 A | 7/1993 | Pins et al. |
| 5,273,758 A | 12/1993 | Royce |
| 5,326,852 A | 7/1994 | Fujikake et al. |
| 5,350,741 A | 9/1994 | Takada |
| 5,378,462 A | 1/1995 | Boedecker et al. |
| 5,387,420 A | 2/1995 | Mitchell |
| 5,427,798 A | 6/1995 | Ludwig et al. |
| RE34,990 E | 7/1995 | Khanna et al. |
| 5,458,887 A | 10/1995 | Chen et al. |
| 5,460,826 A | 10/1995 | Merrill et al. |
| 5,472,943 A | 12/1995 | Crain et al. |
| 5,508,042 A | 4/1996 | Oshlack et al. |
| 5,552,159 A | 9/1996 | Mueller et al. |
| 5,556,640 A | 9/1996 | Ito et al. |
| 5,562,920 A | 10/1996 | Demmer et al. |
| 5,591,452 A | 1/1997 | Miller et al. |
| 5,593,694 A | 1/1997 | Hayashida et al. |
| 5,601,842 A | 2/1997 | Bartholomaeus |
| 5,620,697 A | 4/1997 | Tormala et al. |
| 5,679,685 A | 10/1997 | Cincotta et al. |
| 5,681,517 A | 10/1997 | Metzger |
| 5,707,636 A | 1/1998 | Rodriguez et al. |
| 5,741,519 A | 4/1998 | Rosenberg et al. |
| 5,792,474 A | 8/1998 | Rauchfuss |
| 5,801,201 A | 9/1998 | Gradums et al. |
| 5,811,126 A | 9/1998 | Krishanamurthy |
| 5,849,240 A | 12/1998 | Miller et al. |
| 5,866,164 A | 2/1999 | Kuczynski et al. |
| 5,900,425 A | 5/1999 | Kanikanti et al. |
| 5,908,850 A | 6/1999 | Zeitlin et al. |
| 5,914,132 A | 6/1999 | Elm et al. |
| 5,916,584 A | 6/1999 | O'Donoghue et al. |
| 5,928,739 A | 7/1999 | Pophusen et al. |
| 5,939,099 A | 8/1999 | Grabowski et al. |
| 5,945,125 A | 8/1999 | Kim |
| 5,948,787 A | 9/1999 | Merill et al. |
| 5,962,488 A | 10/1999 | Lang |
| 5,965,161 A | 10/1999 | Oshlack et al. |
| 5,968,925 A | 10/1999 | Knidlberger |
| 6,001,391 A | 12/1999 | Zeidler et al. |
| 6,009,390 A | 12/1999 | Gupta et al. |
| 6,009,690 A | 1/2000 | Rosenberg et al. |
| 6,051,253 A | 4/2000 | Zettler et al. |
| 6,071,970 A | 6/2000 | Mueller et al. |
| 6,077,538 A | 6/2000 | Merrill et al. |
| 6,090,411 A | 7/2000 | Pillay et al. |
| 6,093,420 A | 7/2000 | Baichwal |
| 6,096,339 A | 8/2000 | Ayer et al. |
| 6,117,453 A | 9/2000 | Seth et al. |
| 6,120,802 A | 9/2000 | Breitenbach et al. |
| 6,133,241 A | 10/2000 | Bok et al. |
| 6,183,781 B1 | 2/2001 | Burke |
| 6,235,825 B1 | 2/2001 | Yoshida et al. |
| 6,228,863 B1 | 5/2001 | Palermo et al. |
| 6,238,697 B1 | 5/2001 | Kumar et al. |
| 6,245,357 B1 | 6/2001 | Edgren et al. |
| 6,248,737 B1 | 6/2001 | Buschmann et al. |
| 6,254,887 B1 | 7/2001 | Miller et al. |
| 6,261,599 B1 | 7/2001 | Oshlack |
| 6,290,990 B1 | 9/2001 | Grabowski et al. |
| 6,306,438 B1 | 10/2001 | Oshlack et al. |
| 6,309,668 B1 | 10/2001 | Bastin et al. |
| 6,318,650 B1 | 11/2001 | Breitenbach et al. |
| 6,322,819 B1 | 11/2001 | Burnside et al. |
| 6,326,027 B1 | 12/2001 | Miller et al. |
| 6,335,035 B1 | 1/2002 | Drizen et al. |
| 6,337,319 B1 | 1/2002 | Wang |
| 6,340,475 B2 | 1/2002 | Shell et al. |
| 6,344,215 B1 | 2/2002 | Bettman et al. |
| 6,344,535 B1 | 2/2002 | Timmermann et al. |
| 6,355,656 B1 | 3/2002 | Zeitlin et al. |
| 6,375,957 B1 | 4/2002 | Kaiko et al. |
| 6,375,963 B1 | 4/2002 | Repka et al. |
| 6,387,995 B1 | 5/2002 | Sojka |
| 6,399,100 B1 | 6/2002 | Clancy et al. |
| 6,419,954 B1 | 7/2002 | Chu et al. |
| 6,436,441 B1 | 8/2002 | Sako et al. |
| 6,348,469 B1 | 9/2002 | Seth |
| 6,455,052 B1 | 9/2002 | Marcussen et al. |
| 6,461,644 B1 | 10/2002 | Jackson et al. |
| 6,488,939 B1 | 12/2002 | Zeidler et al. |
| 6,488,962 B1 | 12/2002 | Berner et al. |
| 6,488,963 B1 | 12/2002 | McGinity et al. |
| 6,534,089 B1 | 3/2003 | Ayer et al. |
| 6,547,977 B1 | 4/2003 | Yan et al. |
| 6,547,997 B1 | 4/2003 | Breithenbach et al. |
| 6,562,375 B1 | 5/2003 | Sako et al. |
| 6,569,506 B1 | 5/2003 | Jerdee et al. |
| 6,572,889 B1 | 6/2003 | Guo |
| 6,623,754 B2 | 9/2003 | Guo et al. |
| 6,635,280 B2 | 10/2003 | Shell et al. |
| 6,696,088 B2 | 2/2004 | Oshlack et al. |
| 6,699,503 B1 | 3/2004 | Sako et al. |
| 6,723,340 B2 | 4/2004 | Gusler et al. |
| 6,723,343 B2 | 4/2004 | Kugelmann |
| 6,733,783 B2 | 5/2004 | Oshlack et al. |
| 6,753,009 B2 | 6/2004 | Luber et al. |
| 6,821,588 B1 | 11/2004 | Hammer et al. |
| 6,979,722 B2 | 12/2005 | Hamamoto et al. |
| 7,074,430 B2 | 7/2006 | Miller et al. |
| 7,129,248 B2 | 10/2006 | Chapman et al. |
| 7,141,250 B2 | 11/2006 | Oshlack et al. |
| 7,157,103 B2 | 1/2007 | Sackler |
| 7,176,251 B1 | 2/2007 | Bastioli et al. |
| RE39,593 E | 4/2007 | Buschmann et al. |
| 7,201,920 B2 | 4/2007 | Kumar et al. |
| 7,214,385 B2 | 5/2007 | Gruber |
| 7,230,005 B2 | 6/2007 | Shafer et al. |
| 7,300,668 B2 | 11/2007 | Pryce et al. |
| 7,332,182 B2 | 2/2008 | Sackler |
| 7,388,068 B2 | 6/2008 | Falk et al. |
| 7,399,488 B2 | 7/2008 | Hirsh et al. |
| 7,510,726 B2 | 3/2009 | Kumar et al. |
| 7,674,799 B2 | 3/2010 | Chapman et al. |
| 7,674,800 B2 | 3/2010 | Chapman et al. |
| 7,683,072 B2 | 3/2010 | Chapman et al. |
| 7,776,314 B2 | 8/2010 | Bartholomaus et al. |
| 7,842,307 B2 | 11/2010 | Oshlack et al. |
| 7,851,482 B2 | 12/2010 | Dung et al. |
| 7,939,543 B2 | 5/2011 | Kupper |
| 7,968,119 B2 | 6/2011 | Farrell |
| 7,994,364 B2 | 8/2011 | Fischer et al. |
| 8,075,872 B2 | 12/2011 | Arkenau-Maric et al. |
| 8,101,630 B2 | 1/2012 | Kumar et al. |
| 8,114,383 B2 | 2/2012 | Bartholomaeus et al. |

(56) References Cited

U.S. PATENT DOCUMENTS

| | | |
|---|---|---|
| 8,114,384 B2 | 2/2012 | Arkenau et al. |
| 8,114,838 B2 | 2/2012 | Marchionni |
| 8,192,722 B2 | 6/2012 | Arkenau-Maric et al. |
| 8,202,542 B1 | 6/2012 | Mehta et al. |
| 8,309,060 B2 | 11/2012 | Bartholomaus et al. |
| 8,309,122 B2 | 11/2012 | Kao et al. |
| 8,323,889 B2 | 12/2012 | Arkenau-Maric et al. |
| 8,329,216 B2 | 12/2012 | Kao et al. |
| 8,337,888 B2 | 12/2012 | Wright et al. |
| 8,383,152 B2 | 2/2013 | Jans et al. |
| 8,420,056 B2 | 4/2013 | Arkenau-Maric et al. |
| 8,445,023 B2 | 5/2013 | Guimberteau et al. |
| 8,722,086 B2 | 5/2014 | Arkenau-Maric et al. |
| 8,858,963 B1 | 10/2014 | Devarakonda et al. |
| 9,192,578 B2 | 11/2015 | McGinity et al. |
| 9,629,807 B2 | 4/2017 | Arkenau-Maric et al. |
| 2001/0038852 A1 | 11/2001 | Kolter et al. |
| 2002/0012701 A1 | 1/2002 | Kolter et al. |
| 2002/0015730 A1 | 2/2002 | Hoffmann et al. |
| 2002/0051820 A1 | 5/2002 | Shell et al. |
| 2002/0114838 A1 | 8/2002 | Ayer et al. |
| 2002/0132359 A1 | 9/2002 | Waterman |
| 2002/0132395 A1 | 9/2002 | Iyer et al. |
| 2002/0176888 A1 | 11/2002 | Bartholomaeus et al. |
| 2002/0187192 A1 | 12/2002 | Joshi et al. |
| 2002/0192277 A1 | 12/2002 | Oshlack et al. |
| 2003/0008409 A1 | 1/2003 | Spearman et al. |
| 2003/0015814 A1 | 1/2003 | Krull et al. |
| 2003/0017532 A1 | 1/2003 | Biswas et al. |
| 2003/0021546 A1 | 1/2003 | Sato |
| 2003/0044458 A1 | 3/2003 | Wright et al. |
| 2003/0044464 A1 | 3/2003 | Ziegler et al. |
| 2003/0064099 A1 | 4/2003 | Oshlack et al. |
| 2003/0068276 A1 | 4/2003 | Hughes et al. |
| 2003/0068370 A1 | 4/2003 | Sackler et al. |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0069263 A1 | 4/2003 | Breder et al. |
| 2003/0077297 A1 | 4/2003 | Chen et al. |
| 2003/0091630 A1 | 5/2003 | Louie-Helm et al. |
| 2003/0092724 A1 | 5/2003 | Huaihung et al. |
| 2003/0104052 A1 | 6/2003 | Berner et al. |
| 2003/0104053 A1 | 6/2003 | Gusler et al. |
| 2003/0118641 A1 | 6/2003 | Maloney et al. |
| 2003/0124185 A1 | 7/2003 | Oshlack et al. |
| 2003/0125347 A1 | 7/2003 | Anderson et al. |
| 2003/0129230 A1 | 7/2003 | Baichwal et al. |
| 2003/0133985 A1 | 7/2003 | Louie-Helm et al. |
| 2003/0143269 A1 | 7/2003 | Oshlack et al. |
| 2003/0152622 A1 | 8/2003 | Louie-Helm et al. |
| 2003/0158242 A1 | 8/2003 | Kugelmann |
| 2003/0175326 A1 | 9/2003 | Thombre |
| 2003/0198677 A1 | 10/2003 | Pryce Lewis et al. |
| 2003/0215508 A1 | 11/2003 | Davis et al. |
| 2003/0232895 A1 | 12/2003 | Omidian et al. |
| 2004/0010000 A1 | 1/2004 | Ayer et al. |
| 2004/0011806 A1 | 1/2004 | Luciano et al. |
| 2004/0052731 A1 | 3/2004 | Hirsh et al. |
| 2004/0052844 A1 | 3/2004 | Hsiao et al. |
| 2004/0081694 A1 | 4/2004 | Oshlack |
| 2004/0091528 A1 | 5/2004 | Rogers et al. |
| 2004/0126428 A1 | 7/2004 | Hughes et al. |
| 2004/0131671 A1 | 7/2004 | Zhang et al. |
| 2004/0156899 A1 | 8/2004 | Louie-Helm et al. |
| 2004/0170567 A1 | 9/2004 | Sackler |
| 2004/0170680 A1 | 9/2004 | Oshlack et al. |
| 2004/0185105 A1 | 9/2004 | Berner et al. |
| 2004/0213845 A1 | 10/2004 | Sugihara |
| 2004/0213848 A1 | 10/2004 | Li et al. |
| 2005/0015730 A1 | 1/2005 | Gunturi et al. |
| 2005/0031546 A1 | 2/2005 | Bartholomaeus et al. |
| 2005/0058706 A1 | 3/2005 | Bartholomaeus et al. |
| 2005/0063214 A1 | 3/2005 | Takashima |
| 2005/0089475 A1 | 4/2005 | Gruber |
| 2005/0089569 A1 | 4/2005 | Bar-Shalom |
| 2005/0095291 A1 | 5/2005 | Oshlack et al. |
| 2005/0106249 A1 | 5/2005 | Hwang et al. |
| 2005/0112067 A1 | 5/2005 | Kumar et al. |
| 2005/0127555 A1 | 6/2005 | Gusik et al. |
| 2005/0152843 A1 | 7/2005 | Bartholomaus et al. |
| 2005/0181046 A1 | 8/2005 | Oshlack et al. |
| 2005/0186139 A1 | 8/2005 | Bartholomaeus et al. |
| 2005/0191244 A1 | 9/2005 | Bartholomaeus et al. |
| 2005/0191352 A1 | 9/2005 | Hayes |
| 2005/0192333 A1 | 9/2005 | Hinze et al. |
| 2005/0214223 A1 | 9/2005 | Bartholomaeus et al. |
| 2005/0220877 A1 | 10/2005 | Patel |
| 2005/0222188 A1 | 10/2005 | Chapman et al. |
| 2005/0236741 A1 | 10/2005 | Arkenau et al. |
| 2005/0245556 A1 | 11/2005 | Brogman et al. |
| 2005/0266084 A1 | 12/2005 | Li et al. |
| 2006/0002859 A1 | 1/2006 | Arkenau et al. |
| 2006/0002860 A1 | 1/2006 | Bartholomaus et al. |
| 2006/0004034 A1 | 1/2006 | Hinze et al. |
| 2006/0009478 A1 | 1/2006 | Friedman et al. |
| 2006/0017916 A1 | 1/2006 | Clarke et al. |
| 2006/0039864 A1 | 2/2006 | Bartholomaus et al. |
| 2006/0073102 A1 | 4/2006 | Huaihung et al. |
| 2006/0099250 A1 | 5/2006 | Tian et al. |
| 2006/0104909 A1 | 5/2006 | Vaghefi |
| 2006/0182801 A1 | 8/2006 | Breder et al. |
| 2006/0188447 A1 | 8/2006 | Arkenau-Maric et al. |
| 2006/0193782 A1 | 8/2006 | Bartholomaus et al. |
| 2006/0193914 A1 | 8/2006 | Ashworth et al. |
| 2006/0194759 A1 | 8/2006 | Eidelson |
| 2006/0194826 A1 | 8/2006 | Oshlack et al. |
| 2006/0240105 A1 | 10/2006 | Devane et al. |
| 2006/0240110 A1 | 10/2006 | Kiick et al. |
| 2006/0269603 A1 | 11/2006 | Brown Miller et al. |
| 2007/0003616 A1 | 1/2007 | Arkenau-Maric et al. |
| 2007/0003617 A1 | 1/2007 | Fischer et al. |
| 2007/0020188 A1 | 1/2007 | Sackler |
| 2007/0020335 A1 | 1/2007 | Chen et al. |
| 2007/0042044 A1 | 2/2007 | Fischer et al. |
| 2007/0048228 A1 | 3/2007 | Arkenau-Maric et al. |
| 2007/0065365 A1 | 3/2007 | Kugelmann et al. |
| 2007/0092573 A1 | 4/2007 | Joshi et al. |
| 2007/0183979 A1 | 8/2007 | Arkenau-Maric et al. |
| 2007/0183980 A1 | 8/2007 | Arkenau-Maric et al. |
| 2007/0184117 A1 | 8/2007 | Gregory et al. |
| 2007/0190142 A1 | 8/2007 | Breitenbach et al. |
| 2007/0196396 A1 | 8/2007 | Pilgaonkar et al. |
| 2007/0196481 A1 | 8/2007 | Amidon et al. |
| 2007/0224129 A1 | 9/2007 | Guimberteau et al. |
| 2007/0231268 A1 | 10/2007 | Emigh et al. |
| 2007/0259045 A1 | 11/2007 | Mannion et al. |
| 2007/0264327 A1 | 11/2007 | Kumar et al. |
| 2007/0269505 A1 | 11/2007 | Flath et al. |
| 2007/0292508 A1 | 12/2007 | Szamosi et al. |
| 2008/0020032 A1 | 1/2008 | Crowley et al. |
| 2008/0063725 A1 | 3/2008 | Guimberteau et al. |
| 2008/0069871 A1 | 3/2008 | Vaughn et al. |
| 2008/0075669 A1* | 3/2008 | Soscia .............. A61K 9/2077 424/10.2 |
| 2008/0075768 A1 | 3/2008 | Vaughn et al. |
| 2008/0081290 A1 | 3/2008 | Wada et al. |
| 2008/0085304 A1 | 4/2008 | Baichwal et al. |
| 2008/0131503 A1 | 6/2008 | Holm et al. |
| 2008/0145429 A1 | 6/2008 | Leyenecker et al. |
| 2008/0152595 A1 | 6/2008 | Emigh et al. |
| 2008/0181932 A1 | 7/2008 | Bortz et al. |
| 2008/0220079 A1 | 9/2008 | Chen |
| 2008/0233178 A1 | 9/2008 | Reidenberg et al. |
| 2008/0234352 A1 | 9/2008 | Fischer et al. |
| 2008/0247959 A1 | 10/2008 | Bartholomaus et al. |
| 2008/0248113 A1 | 10/2008 | Bartholomaus et al. |
| 2008/0280975 A1 | 11/2008 | Badul |
| 2008/0311049 A1 | 12/2008 | Arkenau-Maric et al. |
| 2008/0311187 A1 | 12/2008 | Ashworth et al. |
| 2008/0311197 A1 | 12/2008 | Rkenau-Maric et al. |
| 2008/0311205 A1 | 12/2008 | Habib et al. |
| 2008/0312264 A1 | 12/2008 | Arkenau-Maric et al. |
| 2008/0317695 A1 | 12/2008 | Everaert et al. |

(56) References Cited

U.S. PATENT DOCUMENTS

| | | |
|---|---|---|
| 2008/0317854 A1 | 12/2008 | Arkenau et al. |
| 2009/0004267 A1 | 1/2009 | Arkenau-Maric et al. |
| 2009/0005408 A1 | 1/2009 | Arkenau-Maric et al. |
| 2009/0011016 A1 | 1/2009 | Cailly-Dufestel et al. |
| 2009/0017121 A1 | 1/2009 | Berner et al. |
| 2009/0022798 A1 | 1/2009 | Rosenberg et al. |
| 2009/0081287 A1 | 3/2009 | Wright et al. |
| 2009/0081290 A1 | 3/2009 | McKenna et al. |
| 2009/0117191 A1 | 5/2009 | Brown Miller |
| 2009/0202634 A1 | 8/2009 | Jans et al. |
| 2009/0215808 A1 | 8/2009 | Yum et al. |
| 2009/0232887 A1 | 9/2009 | Odidi et al. |
| 2009/0253730 A1 | 10/2009 | Kumar et al. |
| 2009/0317355 A1 | 12/2009 | Roth et al. |
| 2009/0318395 A1 | 12/2009 | Schramm et al. |
| 2010/0015223 A1 | 1/2010 | Cailly-Dufestel et al. |
| 2010/0035886 A1 | 2/2010 | Cincotta et al. |
| 2010/0047345 A1 | 2/2010 | Crowley et al. |
| 2010/0092553 A1 | 4/2010 | Guimberteau et al. |
| 2010/0098758 A1 | 4/2010 | Bartholomaus et al. |
| 2010/0099696 A1 | 4/2010 | Soscia et al. |
| 2010/0104638 A1 | 4/2010 | Dai et al. |
| 2010/0151028 A1 | 6/2010 | Ashworth et al. |
| 2010/0168148 A1 | 7/2010 | Wright et al. |
| 2010/0172989 A1 | 7/2010 | Roth et al. |
| 2010/0203129 A1 | 8/2010 | Andersen et al. |
| 2010/0221322 A1 | 9/2010 | Bartholomaus et al. |
| 2010/0249045 A1* | 9/2010 | Babul .............. A61K 9/485 514/21.4 |
| 2010/0260833 A1 | 10/2010 | Bartholomaus et al. |
| 2010/0280047 A1 | 11/2010 | Kolter et al. |
| 2010/0291205 A1 | 11/2010 | Downie et al. |
| 2010/0297229 A1* | 11/2010 | Sesha .............. A61K 9/209 424/468 |
| 2011/0020451 A1 | 1/2011 | Bartholomaus et al. |
| 2011/0020454 A1 | 1/2011 | Lamarca Casado |
| 2011/0038930 A1 | 2/2011 | Barnscheid et al. |
| 2011/0082214 A1 | 4/2011 | Faure et al. |
| 2011/0092515 A1 | 4/2011 | Qiu et al. |
| 2011/0097404 A1 | 4/2011 | Oshlack et al. |
| 2011/0129535 A1 | 6/2011 | Mantelle |
| 2011/0159100 A1 | 6/2011 | Andersen et al. |
| 2011/0187017 A1 | 8/2011 | Haupts |
| 2011/0223244 A1 | 9/2011 | Liversidge et al. |
| 2011/0245783 A1 | 10/2011 | Stinchcomb |
| 2011/0262496 A1 | 10/2011 | Desai |
| 2012/0034171 A1 | 2/2012 | Arkenau-Maric et al. |
| 2012/0059065 A1 | 3/2012 | Barnscheid et al. |
| 2012/0065220 A1 | 3/2012 | Barnscheid et al. |
| 2012/0077879 A1 | 3/2012 | Vasanthavada et al. |
| 2012/0107250 A1 | 5/2012 | Bartholomaus et al. |
| 2012/0108622 A1 | 5/2012 | Wright et al. |
| 2012/0135071 A1 | 5/2012 | Bartholomaus et al. |
| 2012/0136021 A1 | 5/2012 | Barnscheid et al. |
| 2012/0141583 A1 | 6/2012 | Mannion et al. |
| 2012/0202838 A1 | 8/2012 | Ghosh et al. |
| 2012/0225901 A1 | 9/2012 | Leyendecker et al. |
| 2012/0231083 A1 | 9/2012 | Carley et al. |
| 2012/0251637 A1 | 10/2012 | Bartholomaus et al. |
| 2012/0321716 A1 | 12/2012 | Vachon et al. |
| 2013/0028970 A1 | 1/2013 | Schwier et al. |
| 2013/0090349 A1 | 4/2013 | Gei Ler et al. |
| 2013/0129825 A1 | 5/2013 | Billoet et al. |
| 2013/0129826 A1 | 5/2013 | Gei Ler et al. |
| 2013/0171075 A1 | 7/2013 | Arkenau-Maric et al. |
| 2013/0209557 A1 | 8/2013 | Barnscheid |
| 2013/0225625 A1 | 8/2013 | Barnscheid et al. |
| 2013/0251643 A1 | 9/2013 | Bartholomaus et al. |
| 2013/0289062 A1 | 10/2013 | Kumar et al. |
| 2013/0303623 A1 | 11/2013 | Barnscheid et al. |
| 2013/0330409 A1 | 12/2013 | Mohammad |
| 2014/0010874 A1 | 1/2014 | Sackler |
| 2014/0079780 A1 | 3/2014 | Arkenau Maric et al. |
| 2014/0080858 A1 | 3/2014 | Bartholomäus et al. |
| 2014/0080915 A1 | 3/2014 | Bartholomäus et al. |
| 2014/0094481 A1 | 4/2014 | Fleischer et al. |
| 2014/0112984 A1 | 4/2014 | Arkenau Maric et al. |
| 2014/0112989 A1 | 4/2014 | Bartholomaås et al. |
| 2014/0170079 A1 | 6/2014 | Arkenau Maric et al. |
| 2014/0186440 A1 | 7/2014 | Han et al. |
| 2014/0275143 A1 | 9/2014 | Devarakonda et al. |
| 2014/0356426 A1 | 12/2014 | Barnscheid et al. |
| 2014/0356428 A1 | 12/2014 | Barnscheid et al. |
| 2014/0378498 A1 | 12/2014 | Devarakonda et al. |
| 2015/0017250 A1 | 1/2015 | Wening et al. |
| 2015/0030677 A1 | 1/2015 | Adjei et al. |
| 2015/0064250 A1 | 3/2015 | Ghebre-Sellassie et al. |
| 2015/0079150 A1 | 3/2015 | Fischer et al. |
| 2015/0118300 A1 | 4/2015 | Haswani et al. |
| 2015/0118302 A1 | 4/2015 | Haswani et al. |
| 2015/0118303 A1 | 4/2015 | Haswani et al. |
| 2015/0374630 A1 | 12/2015 | Arkenau Maric et al. |
| 2016/0175256 A1 | 6/2016 | Bartholomaeus et al. |
| 2016/0184297 A1 | 6/2016 | Arkenau-Maric et al. |
| 2016/0256456 A1 | 9/2016 | Caruso et al. |
| 2016/0263037 A1 | 9/2016 | Arkenau Maric et al. |
| 2016/0361308 A1 | 12/2016 | Bartholomaeus et al. |
| 2016/0367549 A1 | 12/2016 | Bartholomaeus et al. |
| 2017/0027886 A1 | 2/2017 | Bartholomaeus et al. |

FOREIGN PATENT DOCUMENTS

| | | |
|---|---|---|
| AU | 2003279317 A1 | 5/2004 |
| AU | 2004264666 B2 | 2/2005 |
| AU | 2004264667 A1 | 2/2005 |
| AU | 2004308653 B2 | 4/2005 |
| AU | 2005259476 B2 | 1/2006 |
| AU | 2005259478 B2 | 1/2006 |
| AU | 2006210145 A1 | 8/2006 |
| AU | 2006210145 B2 | 8/2006 |
| AU | 2009207796 A1 | 7/2009 |
| AU | 2009243681 A1 | 11/2009 |
| AU | 2006311116 B2 | 1/2013 |
| BR | P10413318 A | 10/2006 |
| BR | P10413361 A | 10/2006 |
| BR | P10513300 A | 5/2008 |
| BR | P10606145 A2 | 2/2009 |
| BZ | 2352874 A1 | 6/2000 |
| CA | 0722109 A | 11/1965 |
| CA | 2082573 C | 5/1993 |
| CA | 2577233 A1 | 10/1997 |
| CA | 2650637 A1 | 10/1997 |
| CA | 2229621 A1 | 3/1998 |
| CA | 2317747 A1 | 7/1999 |
| CA | 2343234 A1 | 3/2000 |
| CA | 2414349 A1 | 1/2002 |
| CA | 2456322 A1 | 2/2003 |
| CA | 2502965 A1 | 5/2004 |
| CA | 2503155 A1 | 5/2004 |
| CA | 2534925 A1 | 2/2005 |
| CA | 2534932 A1 | 2/2005 |
| CA | 2489855 A1 | 4/2005 |
| CA | 2551231 A1 | 7/2005 |
| CA | 2572352 A1 | 1/2006 |
| CA | 2572491 A1 | 1/2006 |
| CA | 2595954 A1 | 7/2006 |
| CA | 2229650 C | 8/2006 |
| CA | 2594713 A1 | 8/2006 |
| CA | 2595979 A1 | 8/2006 |
| CA | 2625055 A1 | 4/2007 |
| CA | 2713128 A1 | 7/2009 |
| CA | 2723438 A1 | 11/2009 |
| CA | 2595954 C | 1/2011 |
| CH | 689109 A5 | 10/1998 |
| CL | 20162004 | 5/2005 |
| CL | 20172004 A1 | 5/2005 |
| CL | 200403308 A1 | 9/2005 |
| CL | 200500952 | 11/2005 |
| CL | 200501624 | 12/2005 |
| CL | 200501625 | 6/2006 |
| CL | 424-2013 | 3/2012 |
| CL | 437-2013 | 3/2012 |
| CN | 87102755 A | 10/1987 |
| CN | 1135175 A | 11/1996 |

(56) References Cited

FOREIGN PATENT DOCUMENTS

| | | | |
|---|---|---|---|
| CN | 1473562 A | 2/2004 |
| CN | 1980643 A | 4/2005 |
| CN | 101010071 A | 6/2005 |
| CN | 1671475 A | 9/2005 |
| CN | 101022787 A | 1/2006 |
| CN | 1863513 A | 11/2006 |
| CN | 1863514 A | 11/2006 |
| CN | 1917862 A | 2/2007 |
| CN | 101011395 A | 8/2007 |
| CN | 101027044 A | 8/2007 |
| CN | 101057849 A | 10/2007 |
| CN | 101484135 A | 11/2007 |
| CN | 101091721 A | 12/2007 |
| CN | 101111232 A | 1/2008 |
| CN | 101175482 A | 2/2008 |
| CN | 101370485 A | 2/2009 |
| CN | 1013984839 A | 3/2009 |
| CN | 1942174 A | 2/2010 |
| DE | 2530563 A1 | 1/1977 |
| DE | 4229085 A1 | 3/1994 |
| DE | 4309528 A1 | 9/1994 |
| DE | 4446470 A1 | 6/1996 |
| DE | 69400215 T2 | 10/1996 |
| DE | 19522899 C1 | 12/1996 |
| DE | 2808505 A1 | 1/1997 |
| DE | 19753534 A1 | 6/1999 |
| DE | 19800689 C1 | 7/1999 |
| DE | 19800698 A1 | 7/1999 |
| DE | 19822979 A1 | 12/1999 |
| DE | 69229881 T2 | 12/1999 |
| DE | 19855440 A1 | 6/2000 |
| DE | 19856147 A1 | 6/2000 |
| DE | 19940740 A1 | 3/2001 |
| DE | 19960494 A1 | 6/2001 |
| DE | 10036400 A1 | 6/2002 |
| DE | 69429710 T2 | 8/2002 |
| DE | 10250083 A1 | 12/2003 |
| DE | 10250084 A1 | 5/2004 |
| DE | 10250087 A1 | 5/2004 |
| DE | 10250088 A1 | 5/2004 |
| DE | 10336400 A1 | 3/2005 |
| DE | 10361596 A1 | 9/2005 |
| DE | 102004019916 A1 | 11/2005 |
| DE | 102004020220 A1 | 11/2005 |
| DE | 102004032049 A1 | 1/2006 |
| DE | 102004032051 A1 | 1/2006 |
| DE | 102004032103 A1 | 1/2006 |
| DE | 102005005446 A1 | 8/2006 |
| DE | 102005005449 A1 | 8/2006 |
| DE | 102007011485 A1 | 9/2008 |
| DK | 1658055 T3 | 7/2007 |
| DK | 1658054 T3 | 10/2007 |
| DK | 1515702 T3 | 1/2009 |
| EC | SP066345 A | 8/2006 |
| EP | 0008131 A1 | 2/1980 |
| EP | 0043254 A1 | 1/1982 |
| EP | 0008131 B1 | 12/1982 |
| EP | 0177893 A2 | 4/1986 |
| EP | 0216453 A2 | 4/1987 |
| EP | 0226061 A2 | 6/1987 |
| EP | 0228417 A1 | 7/1987 |
| EP | 0229652 A2 | 7/1987 |
| EP | 0232877 A2 | 8/1987 |
| EP | 0240906 A2 | 10/1987 |
| EP | 0261616 A2 | 3/1988 |
| EP | 0261616 A3 | 3/1988 |
| EP | 0270954 A1 | 6/1988 |
| EP | 0277289 A1 | 8/1988 |
| EP | 0293066 A2 | 11/1988 |
| EP | 0328775 A1 | 8/1989 |
| EP | 0228417 B1 | 9/1990 |
| EP | 0229652 B1 | 10/1991 |
| EP | 0477135 A1 | 3/1992 |
| EP | 0277289 B1 | 4/1992 |
| EP | 0293066 B1 | 4/1993 |
| EP | 0270954 B1 | 5/1993 |
| EP | 0544144 A1 | 6/1993 |
| EP | 0583726 A2 | 2/1994 |
| EP | 0598606 A1 | 5/1994 |
| EP | 0636370 A1 | 2/1995 |
| EP | 0641195 A1 | 3/1995 |
| EP | 0647448 A1 | 4/1995 |
| EP | 0654263 A1 | 5/1995 |
| EP | 0661045 A1 | 7/1995 |
| EP | 0675710 A1 | 10/1995 |
| EP | 0682945 A2 | 11/1995 |
| EP | 0693475 A1 | 1/1996 |
| EP | 0820693 A1 | 1/1996 |
| EP | 0696598 A1 | 2/1996 |
| EP | 0216453 B1 | 3/1996 |
| EP | 0583726 B1 | 11/1996 |
| EP | 0756480 A1 | 2/1997 |
| EP | 0760654 A1 | 3/1997 |
| EP | 0761211 A1 | 3/1997 |
| EP | 0780369 A1 | 6/1997 |
| EP | 0785775 A1 | 7/1997 |
| EP | 0809488 A1 | 12/1997 |
| EP | 0820698 A1 | 1/1998 |
| EP | 0820753 A2 | 1/1998 |
| EP | 0857062 A2 | 8/1998 |
| EP | 0864324 A1 | 9/1998 |
| EP | 0864326 A2 | 9/1998 |
| EP | 0598606 B1 | 6/1999 |
| EP | 0675710 B1 | 8/1999 |
| EP | 0980894 A1 | 2/2000 |
| EP | 0988106 A1 | 3/2000 |
| EP | 1014941 A1 | 7/2000 |
| EP | 1070504 A1 | 1/2001 |
| EP | 1127871 A1 | 8/2001 |
| EP | 1138321 A2 | 10/2001 |
| EP | 1152026 A1 | 11/2001 |
| EP | 1138321 A3 | 1/2002 |
| EP | 1166776 A2 | 1/2002 |
| EP | 1201233 A1 | 5/2002 |
| EP | 0661045 B1 | 7/2002 |
| EP | 1250045 A2 | 10/2002 |
| EP | 1251120 A1 | 10/2002 |
| EP | 1293127 A2 | 3/2003 |
| EP | 1293195 A1 | 3/2003 |
| EP | 1293196 A2 | 3/2003 |
| EP | 1127871 B1 | 9/2003 |
| EP | 1201233 B1 | 12/2004 |
| EP | 1251120 B1 | 12/2004 |
| EP | 1492506 B1 | 1/2005 |
| EP | 1166776 B1 | 2/2005 |
| EP | 1502592 A1 | 2/2005 |
| EP | 1658054 A1 | 2/2005 |
| EP | 1658055 A1 | 2/2005 |
| EP | 1515702 B1 | 3/2005 |
| EP | 1527775 A1 | 4/2005 |
| EP | 1558221 A1 | 8/2005 |
| EP | 1558257 A1 | 8/2005 |
| EP | 1560585 B1 | 8/2005 |
| EP | 1611880 A2 | 1/2006 |
| EP | 1658054 B1 | 5/2006 |
| EP | 1138321 B1 | 1/2007 |
| EP | 1740161 A2 | 1/2007 |
| EP | 1658055 B1 | 3/2007 |
| EP | 1765303 A1 | 3/2007 |
| EP | 0239973 A2 | 4/2007 |
| EP | 1786403 A1 | 5/2007 |
| EP | 1558221 B1 | 6/2007 |
| EP | 1842533 A2 | 10/2007 |
| EP | 1845955 A1 | 10/2007 |
| EP | 1845956 A1 | 10/2007 |
| EP | 1859789 A1 | 11/2007 |
| EP | 1980245 A1 | 10/2008 |
| EP | 1897545 A1 | 12/2008 |
| EP | 2131830 A2 | 12/2009 |
| EP | 2246063 A1 | 11/2010 |
| EP | 2249811 A1 | 11/2010 |
| EP | 2273983 A1 | 1/2011 |
| EP | 2402004 A2 | 1/2012 |
| ES | 2336571 T3 | 12/2004 |

(56) References Cited

FOREIGN PATENT DOCUMENTS

| | | | |
|---|---|---|---|
| ES | 2260042 T3 | 11/2006 |
| ES | 2285497 T3 | 11/2007 |
| ES | 2288621 T3 | 1/2008 |
| ES | 2289542 T3 | 2/2008 |
| ES | 2315505 T3 | 4/2009 |
| GB | 1147210 A | 4/1969 |
| GB | 1567727 A | 5/1980 |
| GB | 2047095 A | 11/1980 |
| GB | 2057878 A | 4/1981 |
| GB | 2238478 A | 6/1991 |
| HR | 20070456 T3 | 6/2007 |
| HR | 200702723 T3 | 11/2007 |
| JP | S36-022895 | 11/1961 |
| JP | S55162714 A | 12/1980 |
| JP | S5659708 A | 5/1981 |
| JP | S56169622 A | 12/1981 |
| JP | S62240061 A | 10/1987 |
| JP | H0249719 A | 2/1990 |
| JP | 03-501737 A | 4/1991 |
| JP | H0517566 A | 1/1993 |
| JP | H06507645 A | 9/1994 |
| JP | 08053331 A | 2/1996 |
| JP | 8-505076 A | 6/1996 |
| JP | H09508410 A | 8/1997 |
| JP | H1057450 A | 3/1998 |
| JP | H10251149 A | 9/1998 |
| JP | 2002524150 A | 8/2002 |
| JP | 2002-275175 A | 9/2002 |
| JP | 2003125706 A | 5/2003 |
| JP | 2003526598 A | 9/2003 |
| JP | 2005506965 A | 3/2005 |
| JP | 2005515152 A | 5/2005 |
| JP | 2005534664 A | 11/2005 |
| JP | 2007501201 A | 1/2007 |
| JP | 2007501202 A | 1/2007 |
| JP | 2007513147 A | 5/2007 |
| JP | 2007533692 A | 11/2007 |
| JP | 2008024603 A | 2/2008 |
| JP | 2008504327 A | 2/2008 |
| JP | 2008528654 A | 7/2008 |
| JP | 2009523833 A | 6/2009 |
| JP | 2009531453 A | 9/2009 |
| JP | 2009537456 A | 10/2009 |
| JP | 2011504455 A | 2/2011 |
| JP | 2011506493 A | 3/2011 |
| JP | 2013536810 A | 9/2013 |
| JP | 2014505736 A | 10/2014 |
| JP | 2014528437 A | 10/2014 |
| KR | 1020060069832 A | 6/2006 |
| KR | 20070039041 A | 4/2007 |
| KR | 20070111510 A | 11/2007 |
| KR | 20090085312 A | 8/2009 |
| KR | 20100111303 A | 10/2010 |
| KR | 20110016921 A | 2/2011 |
| MX | 2007000008 A | 3/2007 |
| MX | 2007000009 A | 3/2007 |
| MX | 2007009393 A | 8/2007 |
| MX | 2010008138 A | 8/2010 |
| MX | 2010012039 A | 11/2010 |
| NO | 20061054 A | 3/2006 |
| NO | 20070578 A | 1/2007 |
| NO | 20074412 A | 11/2007 |
| NZ | 528302 A | 2/2007 |
| PT | 1699440 E | 12/2004 |
| PT | 1658054 E | 5/2006 |
| PT | 1658055 E | 7/2007 |
| PT | 1515702 E | 12/2008 |
| RU | 2131244 C1 | 6/1999 |
| RU | 2198197 C2 | 2/2003 |
| RU | 2220715 C2 | 1/2004 |
| RU | 2396944 C2 | 7/2004 |
| RU | 2326654 C2 | 9/2005 |
| RU | 2339365 C2 | 12/2007 |
| RU | 2354357 C2 | 12/2007 |
| RU | 2007103712 A | 9/2008 |
| RU | 2007103707 A | 11/2008 |
| RU | 2007132975 A | 4/2009 |
| RU | 2567723 C2 | 11/2015 |
| SI | 1515702 T1 | 4/2009 |
| SI | 1699440 T1 | 11/2009 |
| SK | 10612003 A3 | 1/2004 |
| SU | 1759445 A1 | 9/1992 |
| TW | 1254634 B | 5/2006 |
| WO | WO 1980/000841 A1 | 5/1980 |
| WO | WO 1989/005624 A1 | 6/1989 |
| WO | WO 1990/003776 A1 | 4/1990 |
| WO | WO 1993/006723 A1 | 4/1993 |
| WO | WO 93/10765 A1 | 6/1993 |
| WO | WO 1993/010758 A1 | 6/1993 |
| WO | WO 1993/011749 A1 | 6/1993 |
| WO | WO 1993/023017 A1 | 11/1993 |
| WO | WO 1994/006414 A1 | 3/1994 |
| WO | WO 1994/008567 A1 | 4/1994 |
| WO | WO 1995/017174 A1 | 6/1995 |
| WO | WO 1995/020947 A1 | 8/1995 |
| WO | WO 1995/022319 A1 | 8/1995 |
| WO | WO 1995/030422 A1 | 11/1995 |
| WO | WO 1996/000066 A1 | 1/1996 |
| WO | WO 1996/003979 A1 | 2/1996 |
| WO | WO 1996/014058 A1 | 5/1996 |
| WO | WO 1997/000673 A1 | 1/1997 |
| WO | WO 1997/033566 A2 | 9/1997 |
| WO | WO 1997/049384 A1 | 12/1997 |
| WO | WO 1998/035655 A3 | 2/1998 |
| WO | WO 1998/020073 A2 | 5/1998 |
| WO | WO 1998/028698 A1 | 7/1998 |
| WO | WO 1998/035655 A2 | 8/1998 |
| WO | WO 1998/051758 A1 | 11/1998 |
| WO | WO 1999/012864 A1 | 3/1999 |
| WO | WO 1999/032120 A1 | 7/1999 |
| WO | WO 1999/044591 A1 | 9/1999 |
| WO | WO 1999/045887 A2 | 9/1999 |
| WO | WO 1999/048481 A1 | 9/1999 |
| WO | WO 2000/013647 A1 | 3/2000 |
| WO | WO 2000/033835 A1 | 6/2000 |
| WO | WO 2000/040205 A2 | 7/2000 |
| WO | WO 2001/008661 A2 | 2/2001 |
| WO | WO 2001/012230 A1 | 2/2001 |
| WO | WO 2001/015667 A1 | 3/2001 |
| WO | WO 2001/052651 A2 | 7/2001 |
| WO | WO 2001/058451 A1 | 8/2001 |
| WO | WO 2001/097783 A1 | 12/2001 |
| WO | WO 2002/026061 A1 | 4/2002 |
| WO | WO 2002/026262 A2 | 4/2002 |
| WO | WO 2002/026928 A1 | 4/2002 |
| WO | WO 2002/035991 A2 | 5/2002 |
| WO | WO 2002/071860 A1 | 9/2002 |
| WO | WO 2002/088217 A1 | 11/2002 |
| WO | WO 2002/094254 A2 | 11/2002 |
| WO | WO 2003/006723 A1 | 1/2003 |
| WO | WO 2003/013433 A2 | 2/2003 |
| WO | WO 2003/013476 A1 | 2/2003 |
| WO | WO 2003/013479 A1 | 2/2003 |
| WO | WO 2003/013538 A1 | 2/2003 |
| WO | WO 2003/015531 A2 | 2/2003 |
| WO | WO 2003/018015 A1 | 3/2003 |
| WO | WO 2003/024426 A1 | 3/2003 |
| WO | WO 2003/024430 A1 | 3/2003 |
| WO | WO 2003/026624 A1 | 4/2003 |
| WO | WO 2003/026743 A2 | 4/2003 |
| WO | WO 2003/028698 A1 | 4/2003 |
| WO | WO 2003/028990 A1 | 4/2003 |
| WO | WO 2003/031546 A1 | 4/2003 |
| WO | WO 2003/035029 A1 | 5/2003 |
| WO | WO 2003/035053 A1 | 5/2003 |
| WO | WO 2003/035054 A1 | 5/2003 |
| WO | WO 2003/035177 A2 | 5/2003 |
| WO | WO 2003/039561 A1 | 5/2003 |
| WO | WO 2003/049689 A2 | 6/2003 |
| WO | WO 2003/053417 A2 | 7/2003 |
| WO | WO 2003/068392 A1 | 8/2003 |
| WO | WO 2003/070191 A1 | 8/2003 |
| WO | WO 2003/092648 A1 | 11/2003 |
| WO | WO 2003/094812 A1 | 11/2003 |

(56) References Cited

FOREIGN PATENT DOCUMENTS

| | | |
|---|---|---|
| WO | WO 2003/105808 A1 | 12/2003 |
| WO | WO 2004/004693 A1 | 1/2004 |
| WO | WO 2004/043967 A1 | 2/2004 |
| WO | WO 2004/026262 A2 | 4/2004 |
| WO | WO 2004/026263 A2 | 4/2004 |
| WO | WO 2004/026280 A2 | 4/2004 |
| WO | WO 2004/037230 A1 | 5/2004 |
| WO | WO 2004/037259 A1 | 5/2004 |
| WO | WO 2004/037260 A1 | 5/2004 |
| WO | WO 2004/066910 A2 | 8/2004 |
| WO | WO 2004/078212 A1 | 9/2004 |
| WO | WO 2004/084869 A1 | 10/2004 |
| WO | WO 2004/093801 A2 | 11/2004 |
| WO | WO 2004/093819 A2 | 11/2004 |
| WO | WO 2004/098567 A2 | 11/2004 |
| WO | WO 2004/100894 A2 | 11/2004 |
| WO | WO 2005/016313 A1 | 2/2005 |
| WO | WO 2005/016314 A1 | 2/2005 |
| WO | WO 2005/032524 A2 | 2/2005 |
| WO | WO 2005/041968 A2 | 5/2005 |
| WO | WO 2005/053587 A1 | 6/2005 |
| WO | WO 2005/053656 A1 | 6/2005 |
| WO | WO 2005/055981 A2 | 6/2005 |
| WO | WO 2005/060942 A1 | 7/2005 |
| WO | WO 2005/063214 A1 | 7/2005 |
| WO | WO 2005/065646 A2 | 7/2005 |
| WO | WO 2005/066183 A1 | 7/2005 |
| WO | WO 2005/079760 A1 | 9/2005 |
| WO | WO 2005/102286 A1 | 11/2005 |
| WO | WO 2005/102294 A2 | 11/2005 |
| WO | WO 2005/102294 A3 | 11/2005 |
| WO | WO 2005/105036 A1 | 11/2005 |
| WO | WO 2006/002883 A1 | 1/2006 |
| WO | WO 2006/002884 A1 | 1/2006 |
| WO | WO 2006/002886 A1 | 1/2006 |
| WO | WO 2006/002884 B1 | 3/2006 |
| WO | WO 2006/039692 A2 | 4/2006 |
| WO | WO 2006/058249 A2 | 6/2006 |
| WO | WO 2006/082097 A1 | 8/2006 |
| WO | WO 2006/082099 A1 | 8/2006 |
| WO | WO 2006/105615 A1 | 10/2006 |
| WO | WO 2006/128471 A2 | 12/2006 |
| WO | WO 2007/005716 A2 | 1/2007 |
| WO | WO 2007/008752 A2 | 1/2007 |
| WO | WO 2007/014061 A2 | 2/2007 |
| WO | WO 2007/048233 A1 | 5/2007 |
| WO | WO 2007/053698 A2 | 5/2007 |
| WO | WO 2007/085024 A2 | 7/2007 |
| WO | WO 2007/085024 A3 | 7/2007 |
| WO | WO 2007/103105 A2 | 9/2007 |
| WO | WO 2007/103286 A2 | 9/2007 |
| WO | WO 2007/112273 A2 | 10/2007 |
| WO | WO 2007/112285 A2 | 10/2007 |
| WO | WO 2007/112286 A2 | 10/2007 |
| WO | WO 2007/131357 A1 | 11/2007 |
| WO | WO 2008/023261 A1 | 2/2008 |
| WO | WO 2008/033523 A1 | 3/2008 |
| WO | WO 2008/069941 A2 | 6/2008 |
| WO | WO 2008/086804 A2 | 7/2008 |
| WO | WO 2008/107149 A2 | 9/2008 |
| WO | WO 2008/107149 A3 | 9/2008 |
| WO | WO 2008/109462 A2 | 9/2008 |
| WO | WO 2008/132707 A1 | 11/2008 |
| WO | WO 2008/142627 A2 | 11/2008 |
| WO | WO 2008/148798 A2 | 12/2008 |
| WO | WO 2009/005803 A1 | 1/2009 |
| WO | WO 2009/014534 A1 | 1/2009 |
| WO | WO 2009/135680 A1 | 2/2009 |
| WO | WO 2009/034541 A2 | 3/2009 |
| WO | WO 2009/034541 A3 | 3/2009 |
| WO | WO 2009/034541 A9 | 3/2009 |
| WO | WO 2009/035474 A1 | 3/2009 |
| WO | WO 2009/051819 A1 | 4/2009 |
| WO | WO 2009/076764 A1 | 6/2009 |
| WO | WO 2009/092601 A1 | 7/2009 |
| WO | WO 2009/110005 A2 | 9/2009 |
| WO | WO 2009/112273 A2 | 9/2009 |
| WO | WO 2010/022193 A2 | 2/2010 |
| WO | WO 2010/044842 A1 | 4/2010 |
| WO | WO 2010/057036 A2 | 5/2010 |
| WO | WO 2010/066034 A1 | 6/2010 |
| WO | WO 2010/069050 A1 | 6/2010 |
| WO | WO 2010/083843 A1 | 7/2010 |
| WO | WO 2010/083894 A1 | 7/2010 |
| WO | WO 2010/088911 A1 | 8/2010 |
| WO | WO 2010/105672 A1 | 9/2010 |
| WO | WO 2010/140007 A2 | 12/2010 |
| WO | WO 2010/140007 A9 | 12/2010 |
| WO | WO 2010/149169 A2 | 12/2010 |
| WO | WO 2011/008298 A2 | 1/2011 |
| WO | WO 2011/009602 A1 | 1/2011 |
| WO | WO 2011/009603 A1 | 1/2011 |
| WO | WO 2011/009604 A1 | 1/2011 |
| WO | WO 2011/095314 A2 | 8/2011 |
| WO | WO 2011/095314 A3 | 8/2011 |
| WO | WO 2011/128630 A2 | 10/2011 |
| WO | WO 2011/154414 A1 | 12/2011 |
| WO | WO 2012/028317 A1 | 3/2012 |
| WO | WO 2012/028318 A1 | 3/2012 |
| WO | WO 2012/028319 A1 | 3/2012 |
| WO | WO 2012/061779 A1 | 5/2012 |
| WO | WO 2012/076907 A2 | 6/2012 |
| WO | WO 2012/119727 A1 | 9/2012 |
| WO | WO 2012/166474 A1 | 12/2012 |
| WO | WO 2013/003845 A1 | 1/2013 |
| WO | WO 2013/017234 A1 | 2/2013 |
| WO | WO 2013/017242 A1 | 2/2013 |
| WO | WO 2013/030177 A1 | 3/2013 |
| WO | WO 2013/050539 A2 | 4/2013 |
| WO | WO 2013/072395 A1 | 5/2013 |
| WO | WO 2013/084059 A1 | 6/2013 |
| WO | WO 2013/127830 A1 | 9/2013 |
| WO | WO 2013/127831 A1 | 9/2013 |
| WO | WO 2013/128276 A2 | 9/2013 |
| WO | WO 2013/156453 A1 | 10/2013 |
| WO | WO 2013/167735 A1 | 11/2013 |
| WO | WO 2014/059512 A1 | 4/2014 |
| WO | WO 2014/190440 A1 | 12/2014 |
| WO | WO 2014/191396 A1 | 12/2014 |
| WO | WO 2014/191397 A1 | 12/2014 |
| WO | WO 2015/004245 A1 | 1/2015 |
| WO | WO 2015/103379 A1 | 7/2015 |

OTHER PUBLICATIONS

Saleem et al. "Formulation and Evaluation of Tramadol hydrochloride Rectal Suppositories," Indian J. Pharm Sci. Sep.-Oct. 2008; 70(5), 640-544.

Tennant, "Simultaneous Use of Stimulants and Opioids," 2011 [online] retrieved on Jul. 7, 2016 from: http://www.practicalpainmanagement.com/treatments/pharmacological/opioids/simultaneous-use-stimulants-opioids; 7 pages.

The Merck Index, 14th Ed. (2006) No. 0006360 Nalefene.

The Merck Index, 14th Ed. (2006) No. 0006362 Naloxone.

The Merck Index, 14th Ed. (2006) No. 0006363 Naltrexone.

The Merck Index, 14th Ed. (2006) No. 0006959 Oxycodone.

2.9 Methoden der pharmazeutischen Technologie, European Pharmacopeia, 143-144, 1997. (Full English translation attached).

Abertini, B. "New spray congealing atomizer for the microencapsulation of highly concentrated solid and liquid substances" European Journal of Pharmaceutics and Biopharmaceutics 69 (2008) 348-357.

Almeida, A. et al., Ethylene vinyl acetate as matrix for oral sustained release dosage forms produced via hot-melt extrusion, European Journal of Pharmaceutics and Biopharmaceutics 77 (2011) 297-305.

Almeida, A. et al., Sustained release from hot-melt extruded matrices based on ethylene vinyl acetate and polyethylene oxide, European Journal of Pharmaceutics and Biopharmaceutics 82 (2012) 526-533.

(56) References Cited

OTHER PUBLICATIONS

Andre et al., "O-Demethylation of Opiod Derivatives With Methane Sulfonic Acid/Methoinine: Application to the Synthesis of Naloxone and Analogues" Synthetic Comm. 22(16), pp. 2313-2327, 1992.
Apicella A.et al., Biomaterials, vol. 14, No. 2, pp. 83-90,1993.
Application of a modelling system in the formulation of extended release hydrophilic matrices, Reprinted from Pharmaceutical Technology Europe, Jul. 2006.
Application of Opadry II, complete film coating system, on metformin HCI extended release matrices containing Polyox water soluble resin, Colorcon Apr. 2009.
Arnold C., "Teen Abuse of Painkiller OxyContin on the Rise," www.npr.org, Dec. 19, 2005.
Augustine, R.L., Catalytic Hydrogenation of a, B-Unsaturated Ketones. III The Effect of Quantity and Type of Catalysts, J.Org Chem. 28(1), pp. 152-155, Abstract 1963.
Avis, Kenneth, Parenteral Preparations. Chapter 85. pp. 1518-1541In Remington's Pharmaceutical Sciences, 17th Ed, 1985.
Bailey, F.E., et al., "Some properties of poly(ethylene oxide) in aqueous solution," Journal of Applied Polymer Science, vol. 1, Issue No. 1, pp. 56-62. 1959.
Bauer et al. Lehrbuch der Pharmazeutischen Technologie. Eight Edition 2006. Stutt art, pp. 343-352.
Bauer et al. Lehrbuch der Pharmazeutischen Technologie. Sixth Edition 1999. Stull art, pp. IX-XV, Table of contents. (Full English translation attached).
Bauer, Kurt H., et al., Coated Pharmaceutical Dosage Forms— Fundamentals, Manufacturing Techniques, Biopharmaceutical Aspects, Test Methods and Raw Materials, 1st edition, 1998, CRC Press, Medpharm Scientific Publishers. (Preface, Table of Content, List of Abbreviations, Explanation of Terms only).
Baum et al.,"The impact of the addition of naloxone on the use and abuse of pentazocine", Public Health Reports, Jul.-Aug. 1987, vol. 102, No. 4, p. 426-429.
Bingwen et al, 2008, p. 367. (full translation attached).
Block, Lawrence. Medicated Applications. Chapter 88. In Remington's Pharmaceutical Sciences, 17th Ed, 1985.
Borquist et al., "Simulation of the release from a multiparticulate system validated by single pellet and dose release experiements," J. Controlled Release, 97: 453-465 (2004).
Braun, et al. A study of Bite Force. Part 2: Relationship to Various cephalometric Measurements. Angel Orthodontist, vol. 65 (5) pp. 373-377, 1995.
Brown, The Dissolution Procedure: Development and Validation, heading "Study Design", "Time Points" US Pharmacopoeia (USP), vol. 31(5), General Chapter 1092, pp. 1-15, 2006.
Bruce et al, Properties of hot-melt extuded tablet formulations for the colonic delivery of 5-aminosalicylic acid, European Journal of Pharmaceutics and Biopharmaceutics, 59 (2005) 85-97.
Caraballo, Journal of Controlled Release, vol. 69, pp. 345-355, 2000.
Carbopol 71G, retrieved Mar. 10, 2014 from http://www.lubrizol.com/LifeScience/Products/Carbopol71G-NF.html.
Cawello, "Parameters for Compartment-free Pharmacokinetics— Standardization of Study Design, Data Analysis and Reporting" 1999, pp. XI-XIII (Table of contents).
Chibuzor et al. "Formulation Development and Evaluation of Drug Release Kinetics from Colon-Targeted Ibuprofen Tablets Based on Eudragit RL 100—Chitosan Interpolyelectrolyte Complexes," Hindawi Publ. Corporation ISRN Pharmaceutics, vol. 2013, Article ID 838403.
Committee for Proprietary Medicinal Products. Note for Guidance on the Investigation of Bioavailability and Bioequivalence. 2001. pp. 1-18.
Coppens et al., "Hypromellose, Ethylcellulose, and Polyethylene Oxide Use in Hot Melt Extrusion"; Pharmaceutical Technology, 62-70, Jan. 2005.
Cornish, P. "Avoid the Crush": hazards of medication administration in patients with dysphagia or a feeding tube, CMA Media Inc., CMAJ. 172(7), pp. 871-872, 2005.
Costa et al. "Modeling and comparison of dissolution profiles"; European Journal of Pharmaceutical Sciences 13 (2001) 123-33.
Crowley M.M. et al., "Stability of polyethylene oxide in matrix tablets prepared by hot-melt extrusion," Biomaterials 23, 2002, pp. 4241-4248.
Crowley MM, Drug Dev Ind Pharm. Sep. 2007; 33(9):909-26. (Abstract only).
Dachille et al., "High-pressure Phase Transformations in Laboratory Mechanical Mixers and Mortars", Nature, vol. 186, Apr. 2, 1960, pp. 34 and 71.
Dachille, F. et al., "High-Pressure Phase Transformation in Laboratory Mechanical Mixers and Mortars", 1960., Nature, vol. 186, pp. 1-2 (abstract).
Davies, et al; European Journal of Pharmaceutics and Biopharmaceutics, 67, 2007, pp. 268-276.
Dean, D.A., E.R. Evans, I.H. Hall, Pharmaceutical Packaging Technology, Taylor & Francis, 1st Edition, Nov. 30, 2000 (Publisher description dated Oct. 22, 2010).
Deighan, C.J. et al., Rhabdomyolysis and acute renal failure resulting from alcohol and drug abuse, Q.J. Med, vol. 93, 2000, pp. 29-33.
Dejong (Pharmaceutisch Weekblad Scientific Edition) 1987, p. 24-28.
Dexheimer, Terahertz Spectroscopy: Principles and Applications (Optical Science and Engineering Series), CRC; 1 edition 2007. (Table of content only).
Dierickx et al., "Co-extrusion as manufacturing technique for fixed-dose combination mini-matrices," European Journal of Pharmaceutics and Biopharmaceutics 81 (2012), 683-689.
Disanto, Anthony. Bioavailability and Bioequivalency Testing. Chapter 77. In Remington's Pharmaceutical Sciences, 17th Ed, 1985.
Dow Chemical Company, "Using Dow Excipients for Controlled Release of Drugs in Hydrophilic Matrix Systems", Sep. 2006, pp. 1-36.
Dow Excipients Chem. of Poly. Water Soluble-Resin 2004, pp. 1-2.
Dow Technical Data, POLYOX WSR Solid Dosage Formulation via Melt Extrusion, Feb. 2003, pp. 1-3.
Efentakis M et al. "Evaluation of High Molecular Weight Poly(Oxyethylene) (Polyox) Polymer: Studies of Flow Properties and Release Rates of Furosemide and Captopril from controlled-Release hard Gelatin Capsules", Pharmaceutical Development and Technology, 5 (3), pp. 339-346, 2000.
Eggleston, "The seat of the emetic action of various drugs," J. Pharmacol. Exp. Ther. 7, 225-253 (1915).
El-Egakey, Adel et al, "Hot extruded dosage forms Part I Technology and dissolution kinetics of polymeric matrices" Pharmacerutica Acta Helvetiae, vol. 46, pp. 31-53,Mar. 19, 1970.
El-Sherbiny I.M. et al "Preparation, characterization, swelling and in vitro drug release behaviour of poly[N-acryloylglycine-chitosan] interplymeric pH and thermally-resposive hydrogels", European Polymer Journal, vol. 41, pp. 2584-2591, 2005.
Encyclopedia of Pharmaceutical Technology, Third Edition, vol. 1, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 2, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 3 edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 4, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 5, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 6, edited by James Swarbrick PharmaceuTech, Inc., Pinehurst, North Carolinia, USA (Table of Contents only), Oct. 25, 2006.

(56) References Cited

OTHER PUBLICATIONS

Encyclopedia of Pharmacological Technology, Informa Healthcare, 1st Ed., 1996, vol. 14 (Table of Content only).
Erskine, Jr., Clyde. Quality Assurance and Control. Chapter 83. pp. 1487-1491 In Remington's Pharmaceutical Sciences, 17th Ed, 1985.
Eudragit NE40D web page from Evonik website; downloaded Feb. 24, 2015.
Eudragit RS PO web page from Evonik website; downloaded Feb. 24, 2015.
European Pharmacopeia 5.0; Glyceryl behenate monograph; dated Jan. 2005; downloaded Feb. 24, 2015.
European Pharmacopoeia 2.9.40 "Uniformity of Dosage Units", 2006, pp. 3370-3373.
European Pharmacopoeia 5.0, 2.9.8 "Resistance to Crushing of Tablets", 2005, p. 235.
European Pharmacopoeia, Third Edition Supplement 2000, Council of Europe, Strasbourg, 2000, pp. 85-107.
European Pharmacopoeia, Third Edition, Council of Europe, Strasbourg, 1997, pp. 127-152.
European Search Report and Opinion Application No. 12002708.1-1219, dated Sep. 24, 2012.
European Search Report and Opinion Application No. 14176277.3-1460, dated Dec. 15, 2014.
European Search Report and Opinion, Application No. 11006253.6-2112, dated Dec. 16, 2011.
European Search Report and Opinion, Application No. 11006254.4-2112, dated Dec. 16, 2011.
European Search Report and Opinion, Application No. 11008131.2-1219, dated Feb. 24, 2012.
European Search Report and Opinion, Application No. 11009129.5-2112, dated Apr. 10, 2012.
,European Search Report and Opinion, Application No. 12001296.8-1219, dated Jun. 26, 2012.
European Search Report and Opinion, Application No. 12001301.6-1219, dated Jun. 26, 2012.
European Search Report and Opinion, Application No. 12003743.7-1219, dated Sep. 24, 2012.
European Search Report and Written Opinion for EP Application No. 13169658.5, dated Aug. 6, 2013.
European Search Report and Written Opinion for EP Application No. 13169659.3, dated Aug. 6, 2013.
European Search Report and Written Opinion for EP Application No. 13176309.9-1460, dated Oct. 9, 2013.
European Search Report and Written Opinion for EP Application No. 13197503.-1460, dated Feb. 18, 2014.
European Search Report and Written Opinion for EP Application No. 13425151.1-1460, dated Mar. 11, 2014.
European Search Report and Written Opinion for EP Application No. 14169801.9-1455 dated Oct. 20, 2014.
Evaluation of Verapamil HCI (240 mg) Extended Release Matrix Formulation Using USP Apparatus III in Biorelevant Dissolution Media, Jul. 2009.
Evonik Industries, Eudragit Application Guidelines, 10th Edition, 2008, (Table of Contents only).
Evonik Rohm GmbH product brochure: EUDRAGIT acrylic polymers for solid oral dosage forms (2009).
Extended European Search Report and Opinion for Application No. EP 15153679.4-1455, dated Jun. 30, 2015.
Extended European Search Report and Opinion for Application No. EP 15165064.5-1455, dated Oct. 16, 2015.
Extended European Search Report and Opinion for Application No. EP 15165065.2-1455, dated Nov. 2, 2015.
Extended European Search Report and Opinion for Application No. EP 15165067.8-1455, dated Nov. 2, 2015.
Extended European Search Report and Opinion for Application No. EP 15165069.4-1455, dated Nov. 2, 2015.
Extended European Search Report and Opinion for Application No. EP 15165070.2-1455, dated Nov. 2, 2015.

Fell J.T., et al, "Determinination of Tablet Strength by the Diametral-Compression Test" Journal of Pharmaceutical Sciences, vol. 59, No. 5, May 1970, pp. 688-691.
Follonier N. et al., "Evaluation of hot-melt extrusion as a new technique for the production of polymer-based pellets for sustained release capsules containing high loadings of freely soluble drugs," Drug Development and Industrial Pharmacy, 20(8), pp. 1323-1339, 1994.
Follonier, N. et al., "Various ways of modulating the release of dltiazem hydrochloride from hot-melt extruded sustained release pellets prepared using polymeric materials" Journal of Controlled Release 36, pp. 243-250, 1995.
Formulation of Polyox ER Matrices for a Highly Soluble Active, Colorcon Jul. 2009.
Foye, W., Principles of Medicinal Chemistry; Analgesics pp. 241-242, at 241 (1989).
Foye, W., Principles of Medicinal Chemistry; Structural Features and Pharmacologic Activity, pp. 63-66 at 65 (1989).
Freed et al., "pH Control of Nucleophilic/electrophilic oxidation", International Journal of Pharmaceutics, vol. 357, pp. 180-188 (2008).
Giles R. et al. Plastic Packaging Materials. Chapter 81. pp. 1473-1477 In Remington's Pharmaceutical Sciences, 17th Ed, 1985.
Goodman and Gilman, "The Pharmacological Basis of Therapeutics, Seventh Edition", MacMillan Publishing Company, Table of Contents. 1985.
Goodman and Gilman, 1985, 7th edition, chapter 22, 491-530.
Goodman and Gilman, 1985, 7th edition, chapter 23, 533-579.
Graham N.B., Poly(Ethylene Glycol) Chemistry: Biotechnical and Biomedical pplications, p. 263-291 Chapter 17, 1992.
Griffin W, "Classification of Surface-Active Agents by HLB" Journal of the Society of Cosmetic Chemists, Atlas Powder Company, 1949, pp. 311-326.
Griffith, et al. "Tablet Crushing and the Law: The Implications for Nursing" Professional Nurse 19(1), pp. 41-42, 2003.
Gryczke et al, "Development and evaluation of orally disintegrating tablets (ODTs) containing Ibuprofen granules prepared by hot melt extrusion", Colloids and surfaces., B, Biointerfaces, Elsevier, Amsteram, NL, vol. 86, No. 2, Apr. 5, 2011, pp. 275-284.
Guidance for Industry—Bioavailability and Bioequivalence—Studies for Orally Aministered Drug Products—General Considerations, FDA, BP, Announced in the Federal Register: vol. 68, No. 53/Mar. 19, 2003.
Guidance for Industry—Statistical Approaches to Establishing Bioequivalence, FDA, BP, Jan. 2001.
Handbook of Pharmaceutical Excipients, 1986, American Pharmaceutical Association, Washington, DC and London (Table of Content Only).
Handbuch der Kunststoff-Extrusionstechnik 1, "Grundlagen" in Chapter 1.2 "Klassifizierun von Extrudern", pp. 3-7. 1989. (Full english translation attached).
Hanning C.D.et al. "The Morphone Hydrogel Suppository. A New Sustained release Rectal Preparation", British Journal of Anaesthesia, 61, pp. 221-227, 1988.
Hartauer, Kerry J. "Influence of Peroxide Impurities in Povidone and Crospovidone on the Stability of Raloxife" Pharma. Dev. & Tech, 5 (3) 303-310 (2002).
Henriest D. et al. In vitro and in vivo evaluation of starch-based hot stage extruded double matrix systems. Journal of Controlled Release. 2001, vol. 75, pp. 391-400.
Hoepfner et al. Fiedler Encyclopedia of Excipients. Sixth Edition, 2007, Aulendorf, Germany; Table of Contents only.
Hong S. et al. Dissolution kinetics and physical characterization of three-layered tablet with poly(ethylene oxide) core matrix capped by Carbopol. Int .J. Pharmacal. 2008, vol. 356, pp. 121-129.
Inert gas—Wikipedia, Dec. 2009, pp. 1-3.
Investigation of a Directly Compressible Metformin HCI 500mg Extended Release Formulation Based on Hypromellose, Colorcon Jul. 2009.
James, A. "The legal and clinical implications of crushing tablet medication", Nurse Times 100(50), 28-33, 2004.
Janicki S. et al. "Slow-Release Microballs: Method of Preparation", Acta Pharm. Technol. 33 (3) 154-155, 1987.

(56) References Cited

OTHER PUBLICATIONS

Jannetto, P. et al, "Oxycodone: Recognition and Pharmacogenomics," Toxicology News, Mar. 2003, 1-7.

Kalant H. et al., Death in Amphetamine Users: Caues and Rates, CMA Journal, vol. 112 (Feb. 8, 1975): 299-304.

Katz N. et al. "Challenges in the development of prescription opioid abuse-deterrent formulations", Clin. J. Pain, 23(8): 648-660 (Oct. 2007).

Kim C.-J. "Drug Release from Compressed Hydrophilic Polyox-WSR Tablets" J Pharm. Sciences 1995, 84(3): pp. 303-306.

Kim N et al. "Preparation and Evaluation of Eudragit Gels. V. Rectal Gel Preparations for Sustained Release and Avoidance of First-Pass Metabolism of Lidocaine", Chem. Pharm Bull. 1992, 40(10) , 2800-2804.

King et al. Oral Solid Dosage Forms. Chapter 90. pp. 163-1632 In Remington's Pharmaceutical Sciences, 17th Ed, 1985.

King, R, "Tablets, Capsules, and Pills" Remington's Pharmaceutical Sciences, pp. 1553-1593, Ch. 89, 1980, 16$^{th}$ Edition.

King, Remington's Pharmaceutical Sciences 17th ed., Chapter 78, p. 1418 (1985).

Knevel, Adelbert. Separation. Chapter 78. pp. 1432-1442 In Remington's Pharmaceutical Sciences, 17th Ed, 1985.

Kolter, K., "Compression Behaviour of Kollidon SR," APV/ APGI 2002, Florence, Apr. 11, 2002.

Kondrat, T. , "Technology dosage forms" Moscow 1991, p. 96.

Lee, Y.-S. et al., Principles of Terahertz Science and Technology (Lecture Notes in Physics), Springer; 1 edition 2008. (Table of Contents Only).

Lenindzer, A., "The molecular basis of the structure and functions of cells" Moscow 1974, p. 68.

Levina et al., "The Effect of Ultrasonic Vibration on the Compaction Characteristics of Ibuprofen" Drug Development and Industrial Pharmacy, vol. 28, No. 5, pp. 495-514, 2002.

Levina M. et al "The Effect of Ultrasonic Vibration on the Compaction Characteristics of Paracetamol", Journal of Pharmaceutical Sciences, vol. 89, No. 6, pp. 705-723, Jun. 2000.

Li et al, "Characterization of Poly(Ethylene Oxide) as a Drug Carrier in Hot-Melt Extrusion", Drug Development and Industrial Pharmacy, vol. 32, No. 8, Jan. 1, 2006, pp. 991-1002.

Lieberman, Herbert A., Pharmaceutical Dosage Forms, Tablets, Second Edition, Revised and Expanded, 1990. vol. 2 (Cover and Table of Content only).

Lintner, Carl. Stability of Pharmaceutical Products. Chapter 82. pp. 1478-1486 In Remington's Pharmaceutical Sciences, 17th Ed, 1985.

Liu J. et al., "Properties of Lipophilic Matrix Tables Containing Phenylpropanolamine Hydrochloride Prepared by Hot-Melt Extrusion", EJPB, 52 (2001), pp. 181-190.

Lockhart H. et al, "Packaging of Pharmaceuticals and Health Care Products"; Blackie Academic & Professional; First Edition 1996. (Table of contents only).

Longer et al. Sustained-Release Drug Delivery Systems. Chapter 92. pp. 1611-1661 In Remington's Pharmaceutical Sciences, 17th Ed, 1985.

Madorsky S.L. "Thermal degradation of Polyethylene Oxide and Polypropylene Oxide", Journal of Polymer Science, pp. 183-194 vol. 36, No. 3, Mar. 1959.

Maggi et al., "Dissolution behavior of hydrophilic matrix tablets containing two different polyethylene oxides (PEOs) for the controlled release of a water-soluble drug. Dimensionality study" Biomaterials, 2002, 23, 1113-1119.

Maggi L.et al, "High molecular weight polyethylene oxides (PEOs) as an alternative to HPMC in controlled release dosage form", 2000, International Journal of Pharmaceutics, 195 pp. 229-238.

Maggi, C.. Therapeutic Potential of Capsaicin-like Molecules. Life Sciences, vol. 51, pp. 1777-1781, 1992.

Mank R. et al., "Darstellung wirkstoffhaltiger Extrusionsformlinge auf der Basis von hermoplasten. Teil 1: Untersuchung zur Wirkstoffliberation" Pharmazie 44, H. 11, pp. 773-776, 1989. English language translation of relevant paragraph provided.

Mank R., "Darstellung wirkstoffhaltiger Extrusionsformlinge auf der Basis von hermoplasten. Teil 2: Unersuchungen zur Optimierung der Wirkstofffreigabe" Pharmazie 45, H. 8, pp. 592-593 1990. English language translation of relevant paragraph provided.

Marques, Tablet breaking force, 2008.

Matos, Dr. Rick, Ph.D—Letter Jan. 6, 2011.

McGary, C.W.. Jr. "Degradation of Poly(ethylene Oxide)", Journal of Polymer Science olume XLVI,1960, pp. 51-57.

McGinity et al., Hot-Melt Extrusion as a Pharmaceutical Process, American Pharmaceutical Review, vol. 4 (2), pp. 25-36, 2001.

McGinity, J.W.—Letter of Jan. 26, 2009, pp. 1-4.

McNeill M. et al. Properties controlling the diffusion and release of water-soluble solutes from poly(ethylene oxide) hydrogels. 4. Extended constant rate release from party-coated spheres. Journal Biomat. Sci. Polymer. Ed. 1996, vol. 7, pp. 953-963.

Mesiha M.S. et al "A Screening Study of Lubricants in Wet Powder Passes Suitable for extrusio-spheronization", Drug Development and Industrial Pharmacy, 19(8), pp. 943-959, 1993.

Metformin Hydrochloride 1000 mg Extended Release Tablets, Lubrizol Advanced Materials, Inc., Nov. 20, 2009, Previous Edition Dec. 19, 2008.

Metformin Hydrochloride 750 mg Extended Release Tablets, Lubrizol Advanced Materials, Inc., Sep. 2010.

Miles, R.E. et al., Terahertz Frequency Detection and Identification of Materials and Objects (NATO Science for Peace and Security Series B: Physics and Biophysics), Springer; 1 edition 2007. (Table of contents ).

Miller "To crush or not to crush? What to consider before giving medications to a stent with a tube or who has trouble swallowing", Nursing, pp. 50-52, Feb. 2000.

Mises à jour cumulatives, Vidal, Jan./Oct. 2002 (full translation attached).

Mitchell, "Oral Dosage Forms That Should Not Be Crushed: 2000 Update" Hospital Pharmacy 35(5), 553-557, 2000.

Monolithic: retrieved from internet: http:/merriam-webster.com/dictionary/monolithic. Retrieved on Sep. 2, 2015.

Moorman-Li, R. et al, "A Review of Abuse-Deterrent Opioids for Chronic Nonmalignant Pain." Pharmacy and Therapeutics, vol. 37 No. 7, Jul. 2012, pp. 412-421.

Morissette et al. Advanced Drug Delivery Review 26 (2004), 275-300.

Moroni A. et al, "Application of Poly(Oxyethylene) Homopolymers in Sustained release Solid formulations" Drug Development and Industrial Pharmacy, 21(12) pp. 1411-1428, 1995.

Mullins, John. Ophthalmic Preparations. Chapter 87. pp. 1553-1563; In Remington's Pharmaceutical Sciences, 17th Ed, 1985.

Munjal M. et al., "Polymeric Systems for Amorphous Delta$^\Lambda$ 9—Tetrahydrocannabinol Produced by a Hot-Melt Method. Part II: Effect of Oxidation Mechanisms and Chemical Interactions on Stability" Journal of Pharmaceutical Sciences vol. 95 No. 11, Wiley InterScience, 2006, pp. 2473-2485.

Munsell Color Company, "The Munsell Book of Color: Glossy Collection", X-Rite, Originally published in 1966, pp. 1-7.

Nairn, J.G., Solutions, Emulsion, Suspensions and Extractives. Chapter 84. pp. 1492-1517, In Remington's Pharmaceutical Sciences, 17th Ed, 1985.

Note for Guidance on Stability Testing, EMEA, Aug. 2003, pp. 1-20.

Note for Guidance on the Investigation of Bioavailability and Bioequivalence, EMEA, London, Jul. 26, 2001 (CPMP/EWP/QWP/1401/98).

Ohnishi N. et al., Effect of the Molecular Weight of Polyethylene Glycol on the Bioavailability of Indomethacin Sustained-Release suppoositories Prepared with Solid Dispersion, Chem. Pharm. Bull, 35(8), pp. 3511-3515, 1987.

Oliveira et al., "Production and characterization of laminar coextrudates at room temperature in the absence of solvents," AAPS Annual Meeting and Exposition, Oct. 14-18, 2012, Chicago, USA.

Oxicotin: Balancing Risks and Benefits, United States Senate, Hearing, Feb. 12, 2002.

(56) References Cited

OTHER PUBLICATIONS

Oxycodon (Oxygesic): Missbrauch, Abhaengigkeit and toedliche Folgen durch Injection zerstossener Retardtabletten, Deutsches Ärzteblatt, vol. 36, A2326-A2326, Sep. 5, 2003.
Ozeki T. et al. "Control of Medicine Release From Solid Dispersion Through Poly(ethylene oxide)-Carboxyvinylpolymer Interaction", International Journal of Pharmaceutics, 165, 1998, pp. 239-244.
Ozeki T. et al. "Controlled Release From Solid Dispersion Composed of Poly(ethylene oxide)-Carbopol Interpolymer Complex With Various Cross-Linking Degrees of Carbopol", Journal of Controlled Release. 63, 2000. pp. 287-295.
Ozeki T. et al., "Control of medicine release from solid dispersion composed of the poly(ethylene oxide)-carboxyviylpolymer interpolymer complex by varying molecular wight of poly(ethylene oxide)"Journal of Controlled Release 58, pp. 87-95, 1999.
PCT International Search Report and Written Opinion for PCT Application No. PCT/EP2010/004459 dated Dec. 1, 2010.
PCT International Search Report and Written Opinion for PCT Application No. PCT/EP2009/003290 dated Jul. 9, 2009.
PCT International Search Report and Written Opinion for PCT Application No. PCT/EP2013/053894 dated Mar. 22, 2013.
PCT International Search Report and Written Opinion for PCT Application No. PCT/EP2013/057851 dated Jun. 12, 2013.
PCT International Search Report and Written Opinion for PCT Application No. PCT/EP2013/059728 dated Aug. 6, 2013.
PCT International Search Report and Written Opinion for PCT Application No. PCT/EP2014/064830 dated Aug. 6, 2014.
PCT International Search Report and Written Opinion for PCT Application No. PCT/EP2014/075618 dated Feb. 11, 2015.
PCT International Search Report and Written Opinion for PCT Application No. PCT/EP2014/0777748 dated Feb. 12, 2015.
PCT International Search Report and Written Opinion for PCT Application No. PCT/EP2015/060377 dated Jul. 23, 2015.
PCT International Search Report and Written Opinion for PCT Application No. PCT/EP2015/061343 dated Jul. 21, 2015.
PCT Second Written Opinion for PCT Application No. PCT/EP2013/053893 dated Feb. 21, 2014.
PCT Second Written Opinion for PCT Application No. PCT/EP2013/057851 dated Apr. 15, 2014.
Pentoxifylline 400 mg Extended Release Tablets, Lubrizol Advanced Materials, Inc., Mar. 3, 2011, Previous Edition Nov. 19, 2009.
Perez-Marcos, B., Usefulness of certain varieties of Carbomer in the formulation of hydrophilic furosemide matrices, International Journal of Pharmaceutics, 67 (1991) 113-121.
Pharm. Research, Official Journal of the American Association of Pharmaceutical Scientists, Sep. 1989, 6(9), S-98.
Pharm. Research, Official Journal of the American Association of Pharmaceutical Scientists, Oct. 1991, 8(10), S-192.
Phillips, G. Briggs. Sterilization. Chapter 79. pp. 1443-1454, In Remington's Pharmaceutical Sciences, 17th Ed, 1985.
Physico-mechanical Characterization of Polyox for Table Manufacture, Colorcon Jul. 2009.
Pillay V. et al. A novel approach for constant rate delivery of highly soluble bioactives from a simple monolithic system. Journal of Controlled Release. 2000, vol. 67, pp. 67-78.
Pinto, Joao F. et al.,"Evaluation of the Potential Use of Poly(ethylene oxide) as Tablet- and Extrudate-Forming Material," AAPS PharmSci, 2004; 6 (2), Article 15, pp. 1-10, (http://www.aapspharmsci.org).
Piringer, O.G.and A.L. Baner, Plastic Packaging: Interactions with Food and Pharmaceuticals, Wiley VCH, 2nd Completely Revised Edition, Feb. 13, 2008. (Table of Contents only).
Polyox water soluble resins 2003. http://www.dow.com/webapps/lit/litorder.asp?filepath=polyox/pdfs/noreg/326-00002.pdf.
POLYOX water-soluble resins (DOW Mar. 2002); see http://msds-search.dow.com/PublishedLiteratureDOWCOM/dh_0031/0901b80380031a4a.pdf?filepath=/326-00001.pdf &fromPage=GetDoc).

POLYOX WSR-303, retrieved Mar. 10, 2014 from URL htitp://www.dow.com/dowwolff/en/industrial_solutions/polymers/polyethylene.
POLYOX, COLORCON, Application Data (Apr. 2009) downloaded from http://www.colorcon.com/literature/marketing/mr/Extended%20Release/POLYOX/English/ads_PEO_Antioxidant.pdf.
Pontier, C. et al, "Use of cycles of compression to characterize the behavior of apatitic phosphate powders," Journal of the European Ceramic Society 22 (2002), 1205-1216.
Porter, S. Coating of Pharmaceutical Dosage Forms. Chapter 91. pp. 1633-1643 In Remington's Pharmaceutical Sciences, 17th Ed, 1985.
Prapaitrakul W. et al, "Release of Chlorpheniramine Maleate from Fatty Acid Ester Matrix disks Prepared by Melt-extrusion" J. Pharm. Pharmacol. 43, pp. 377-381, 1991.
Proeschel, P.A. et al., "Task-dependence of activity / bite-force Relations and its impact on estimation of chewing force from EMG"; J. Dent. Res., vol. 81, No. 7, pp. 464-468, 2002.
Purdue News, "Purdue Pharma Provides Update on Development of New Abuse-Resistant Pain Medications; FDA Cites Patient Needs as First Priority; New Drug Application Delayed," www.headaches.about.com, Jun. 18, 2002, pp. 1-6.
Quintavalle et al., "Preparation of sustained release co-extrudates by hot-melt extrusion and mathematical modelling of in vitro/in vivo drug release profiles," European 'Journal of Pharmaceutical Sciences 33 (2008), 282-293.
Radko S.et al., Applied ad Theoretical Electrophoresis 5, pp. 79-88, 1995.
Ravin, L. Preformulation. Chapter 76, pp. 1409-1423, In Remington's Pharmaceutical Sciences, 17th Ed, 1985.
Remington, The Science and Practice of Pharmacy, 19th ed., vol. II, p. 1457 (1995) (providing a table of DFA-approved commercially marketed salts).
Repka M. et al., Bioadhesive Properties of Hydroxypropylcellulose Topical Films Produced by Hot-Melt Extrusion, Journal of Controlled Release, 70 (2001), pp. 341-351.
Repka MA, Drug Dev Ind Pharm. Oct. 2007; 33(10):1043. (Abstract).
Riippi M. et al., The effect of compression force on surface structure, crushing strength, friability and disintegration time of erythromycin acistrate tablets, Eur J Pharm Biopharm, vol. 46, 1998, pp. 339-345.
Rippie E.G. et al, "Regulation of Dissolution Rate by Pellet Geometry" Journal of Pharmaceutical Sciences, Vo. 58, No. 4, pp. 428-431, Apr. 1969.
Rippie, E. Powders. Chapter 89, pp. 1585-1602, In Remington's Pharmaceutical Sciences, 17th Ed, 1985.
Ritschel et al. Die Tablette: Handbuch der Entwicklung, Herstellung und Qualitatssicherung. 2nd Edition, 2002, Ch 6, pp. 515-519. (Full English translation attached).
Ritschel et al. Die Tablette: Handbuch der Entwicklung, Herstellung und Qualitatssicherung. 2nd Edition, 2002, Ch 6, pp. 69-82 and 115-136.
Ritschel et al. Die Tablette: Handbuch der Entwicklung, Herstellung und Qualitatssicherung. 2nd Edition, 2002, Table of content.
Rosiaux et al. "Ethanol-resistant ethylcellulose/guar gum coatings—Importance for formulation parameters" European Journal of Pharmaceutics and Biopharmaceutics, vol. 85, No. 3, (Jul. 25, 2013). pp. 1250-1258.
Rowe C et al. Handbook of Pharmaceutical Excipients. Sixth Edition. 2009, Edition Cantor Verlag Aulendorf, pp. V-IX, Table of Contents.
Rowe C et al., Handbook of Pharmaceutical Excipients, 7th Edition, 2012, Table of Contents.
Salomies et al., "Determination of Oxycodone Hydrochloride in Oral Solutions by High-Performance Thin-Layer Chromatography/Densitometry," Journal of AOAC International, 83: 1497-1501 (2000).
Satish et al. "Formulation and Characterization of Matrix and Triple Layer Matrix Tablets for Controlled Delivery of Tramadol Hydrochloride," International Journal of Pharmaceutical Sciences; 5(4) (2013) 458-464.

(56) References Cited

OTHER PUBLICATIONS

Sax et al., Hawley's Condensed Chemical Dictionary, 11th ed., 1987, p. 1233, definition of "wax".
Scheirs J., et al."Characterizing the Solid-State Thermal Oxidation of Poly (ethylene oxide) Powder", pp. 2014-2019, Polymer, vol. 32, No. 11, 1991.
Schier et al. "Fatality from Administration of Labetalol and Crushed Extended-Release Nifedipine" The Annals of Pharmacotherapy vol. 37, 1420-1423, Oct. 2003.
Schroeder J., et al. Granulierung hydrophober Wirkstoffe im Planetwalzenextruder, Pharm. Ind. 2003, vol. 65, No. 4, 367-372. (Full English translation attached).
Sciarra et al. Aerosols. Chapter 93., pp. 1662-1677, In Remington's Pharmaceutical Sciences, 17th Ed, 1985.
Search result conducted on http://www.unitconversion.org/force/newtons-to-kiloponds-convresion.html, on Jul. 5, 2011 (Conversion of 18.8 kiloponds to newtons).
Shivanand P et al., "Factors Affecting Release of KCl From Melt extruded Polyethylene Disks", Pharmaceutical Research, Oct. 1991, vol. 8, No. 10, p. S-192.
Sidhu et al., "Watch for nonpsychotropics causing psychiatric side effects," Current Psychiatry, vol. 7, No. 4, 2008, 61-74.
Siegel, P. Tonicity, Osmoticity, Osmolality, and Osmolarity. Chapter 80. pp. 1454-1472 In Remington's Pharmaceutical Sciences, 17th Ed, 1985.
Silver, J. "Painkiller OxyContin most commonly abused prescription drug on the streets of Western Pennsylvania", Pittsburg Post-Gazette, Apr. 8, 2001.
Spassov et al., Stereochemistry of Diastereomeric 3-Dialkylaminopropanols and O-Derivatives, J.f. prakt. Chemie, 323:5, 793-800 (1981).
Sprockel O.L et al. "Permeability of Cellulose Polymers: Water Vapour Transmission Rates"., J. Pharma. Pharmacol. 42, pp. 152-157, 1990.
Sreenivasa, B. et al, Design and Evaluation of Ethylene Vinyl Acetate Sintered Matrix Tablets, Indian Journal of Pharmaceutical Sciences, Sep.-Oct. 2003, 65(5): 496-502.
Stafford J., überzogene feste Formen, 1991, 347-67. (English translation attached).
Strang, Abuse of buprenorphie (Temgesic) by snorting, Letter to the editor, British Med. J., 302: 969 (1991).
Stringer J.L., et al "Diffusion of small molecular weight drugs in radiation-crosslinked poly(ethylene oxide) hydrogels", Journal of Controlled Release 42, pp. 195-202, 1996.
Summers et al; "Influence of Crystal Form on Tensile Strength of Compacts of Pharmaceutical Materials" Journal of Pharmaceutical Sciences, vol. 66, No. 8, Aug. 1977, pp. 1172-1175.
Swarbrick, Encyclopedia of Pharmaceutical Technology, Informa Healthcare, 1988, 1st edition, vol. 1, table of contents.
Swarbrick, Encyclopedia of Pharmaceutical Technology, Informa Healthcare, 1988, 1st edition, vol. 10, table of contents.
Swarbrick, Encyclopedia of Pharmaceutical Technology, Informa Healthcare, 1988, 1st edition, vol. 11, table of contents.
Swarbrick, Encyclopedia of Pharmaceutical Technology, Informa Healthcare, 1988, 1st edition, vol. 12, table of contents.
Swarbrick, Encyclopedia of Pharmaceutical Technology, Informa Healthcare, 1988, 1st edition, vol. 13, table of contents.
Swarbrick, Encyclopedia of Pharmaceutical Technology, Informa Healthcare, 1988, 1st edition, vol. 14, table of contents.
Swarbrick, Encyclopedia of Pharmaceutical Technology, Informa Healthcare, 1988, 1st edition, vol. 15, table of contents.
Swarbrick, Encyclopedia of Pharmaceutical Technology, Informa Healthcare, 1988, 1st edition, vol. 16, table of contents.
Swarbrick, Encyclopedia of Pharmaceutical Technology, Informa Healthcare, 1988, 1st edition, vol. 18, table of contents.
Swarbrick, Encyclopedia of Pharmaceutical Technology, Informa Healthcare, 1988, 1st edition, vol. 19, table of contents.
Swarbrick, Encyclopedia of Pharmaceutical Technology, Informa Healthcare, 1988, 1st edition, vol. 2, table of contents.
Swarbrick, Encyclopedia of Pharmaceutical Technology, Informa Healthcare, 1988, 1st edition, vol. 20, table of contents.
Swarbrick, Encyclopedia of Pharmaceutical Technology, Informa Healthcare, 1988, 1st edition, vol. 3, table of contents.
Swarbrick, Encyclopedia of Pharmaceutical Technology, Informa Healthcare, 1988, 1st edition, vol. 4, table of contents.
Swarbrick, Encyclopedia of Pharmaceutical Technology, Informa Healthcare, 1988, 1st edition, vol. 5, table of contents.
Swarbrick, Encyclopedia of Pharmaceutical Technology, Informa Healthcare, 1988, 1st edition, vol. 6, table of contents.
Swarbrick, Encyclopedia of Pharmaceutical Technology, Informa Healthcare, 1988, 1st edition, vol. 7, table of contents.
Swarbrick, Encyclopedia of Pharmaceutical Technology, Informa Healthcare, 1988, 1st edition, vol. 8, table of contents.
Swarbrick, Encyclopedia of Pharmaceutical Technology, Informa Healthcare, 1988, 1st edition, vol. 9, table of contents.
Tablet, www.docstoc.com (2011).
Third Party Observations filed with EPO for Patent EP658055B1, Feb. 2, 2009, pp. 1-8.
Thoma V.K. et al. "Bestimmung der In-vitro-Freigabe von schwach basischen Wirkstoffen aus Ratardarzneiformen", pp. 299-301, Pharm. Ind. 51, Nr. 3, 1989.
Tikhonov, A. et al, Biopharmacy. The Manual for Students of Pharmaceutical Universities and Departments, 2003, pp. 40-41, Kharkov, Ukraine (Full English translation attached).
Tipler, et al, Physics for Scientists and Engineers, vol. I, 6th Edition, pp. 234-235, 2003.
Tompkins et al., "Human abuse liability assessment of oxycodone combined with ultra-low-dose natrexone," Psychopharma., 210: 471-480 (2010).
Tramadol Hydrochloride 100 mg Extended Release Tablets, Lubrizol Advanced Materials, Inc., Sep. 2010.
Tranquilan-Aranilla et al., "Kappa-carrageenan-polyethylene oxide hydrogel blends prepared by gamma irradiation," Radiation Physics and Chemistry vol. 55, pp. 127-131, 1999.
Turco et al. Intravenous Admixtures. Chapter 86. Pages 1542-1552, In Remington's Pharmaceutical Sciences, 17th Ed, 1985.
US Pharmacopoeia, Chapter 1217, Aug. 12, 2008.
Varma et al, Factors Affecting Mechanism and Kinetics of Drug Release from Matrix-Based Oral Controlled Drug Delivery Systems, Am. J. Drug Deliv. 2004: 2 (1): 43-57.
Verhoeven et al., "Influence of polyethylene glycol/polyethylene oxide on the release characteristics of sustained-release ethylcellulose mini-matrices produced by hot-melt extrusion: in vitro and in vivo evaluations," European Journal of Pharmaceutics and Biopharmaceutics 72 (2009) 463-470.
Verhoeven, et al. "Xanthan gum to tailor drug release of sustained-release ethylcellulose mini-matrices prepared via hotmelt extrusion: in vitro and in vivo evaluation," European Journal of Pharmaceutics and Biopharmaceutics, 63 (2006) 320-330.
Vippagunta et al. Crystalline Solids, Advanced Drug Delivery Review 48 (2001), 3-26.
Vynckier et al.,"Hot-melt co-extrusion for the production of fixed-dose combination products with a controlled release ethylcellulose matrix core," International Journal of Pharmaceutics 464 (2014), 65-74.
Wade and Weller, "Handbook of Pharmaceutical Excipients: 2nd Edition", The American Pharmaceutical Association and the Pharmaceutical Press, Washington and London, Table of Contents pp. v-vi, 1994.
Wagner, Pharmazeutische Biologie—Drogen und ihre Inhaltsstoffe—Scharfstoffdrogen, 2nd., revised edition, Gustav Fischer Verlag, Stuttgart—N.Y., 1982, pp. 82-92 (Full English Translation attached).
Wagner, Pharmazeutische Biologie—Drogen und ihre Inhaltsstoffe—Scharfstoffdrogen, 2nd., revised edition, Gustav Fischer Verlag, Stuttgart—N.Y., 1982,Table of Content.
Waltimo, et al, "A novel bite force recorder and maximal isometric bite force values for healthy young adults", Scandinavian Journal of Dental Research 1993; 101: 171-175.
Waltimo, et al, "Maximal bite force and its association with signs and symptoms of craniomandibular disorders in young Finnish non-patients", Acta Odontol Scand 53 (1995): 254-258.

(56) References Cited

OTHER PUBLICATIONS

Waterman et al., "Stabilization of Pharmaceuticals to Oxidative Degradation", Pharmaceutical Development and Technology, vol. 7(1), pp. 1-32, (2002).
Waters et al., "Intravenous Quetiapine-Cocaine Use ("Q-Ball")", Letter to the Editor, Am. J. Psychiatry, 164(1): pp. 173-174 (2007).
Weiss, U., "Derivatives of Morphine. I 14-Dihydroxydihydromorphinone," J. Am. Chem. Soc. 77, pp. 5891-5892, Nov. 20, 1955.
West, Anthony R., Solid state chemistry and its applications, Wiley, New York, 1988, pp. 358 and 365.
Wikipedia—Dextromethorphan Aug. 12, 2013 (and attached related English-language entry dated Dec. 11, 2013).
Woodburn, K.R. et al., Vascular complications of injecting drug misuse, Br. J. of Surgery, vol. 83, 1996, pp. 1329-1334.
Wu N, et al. Mathematical modeling and in vitro study of controlled drug release via a highly swellable and dissoluble polymer matrix: polyethylene oxide with high molecular weights, J Control Release. Feb. 16, 2005;102(3):569-581.
Yang et al., "Zero-Order Release Kinetics from a Self-Correcting Floatable Asymmetric Configuration Drug Delivery System", Journal of Pharmaceutical Sciences, vol. 85, No. 2, Feb. 1996, pp. 170-173.
Yang, et al; "Characterization of Compressibility and Compactibility of Poly(ethylene oxide) Polymers for Modified Release Application by Compaction Simulator"; Journal of Pharmaceutical Sciences, vol. 85, No. 10, pp. 1085-1090, Oct. 1996.
Yarbrough et al, Letters to Nature "Extraordinary effects of mortar-and-pestle grinding on microstructure of sintered alumina gel", Nature 322, pp. 347-349 (Abstract only) (Jul. 24, 1986).
Yeh et al., Stability of Morphine in Aqueous Solution III: Kinetics of Morphine Degradation in Aqueous Solution, Wiley Subscription Services, Inc., Journal of Pharmaceutical Sciences, 50(1): 35-42 (1961).
Zeeshan, F and N. Bukhari, "Development and Evaluation of a Novel Modified-Release Pellet-Based Tablet System for the Delivery of Loratadine and Pseudophedrine Hydrochloride as Model Drugs," AAPS PharmaSciTech 11(2); 910-916 (available online May 22, 2010).
Zhang et al., "Properties of Sustained-Release Tablets Prepared by Hot-Melt Extrusion" Pharmaceutical Development and Technology, 1999, 4(2), 241-250.
Cuesov, Drug Production Technology, Khar'kov, 1999, pp. 351-352.
Decision of the United States District Court for the Southern District of New York, in *In re Endo Pharmaceuticals Inc. and Grünenthal GmbH v. Amneal Pharmaceuticals, LLC et al.*, Findings of Fact and Conclusions of Law, District Judge Thomas P. Griesa, New York, New York, Jan. 14, 2015.
Decision of the United States District Court for the Southern District of New York, in *In re Oxycontin Antitrust Litigation, Purdue Pharma LP v. Teva Pharmaceuticals*, Findings of Fact and Conclusions of Law, District Judge Sidney H. Stein, New York, New York, Jan. 14, 2014.
U.S. Court of Appeals, Federal Circuit, *Purdue Pharma L.P. v. Epic Pharma, LLC*, 117 USPQ2d 1733 (Fed. Cir. 2016).
Al-Angari, A. et al. "The compaction properties of polyethylene glycols," J Pharm. Pharmacol. (1985) 37:151-153.
Al-Nasassrah et al., "The effect of an increase in chain length on the mechanical properties of polyethylene glycols," European Journal of Pharmaceutics and Biopharmaceutics 46 (1998) 31-38.
Anderson, S.L. et al., "A Model for Antiplasticization in Polystyrene," Macromolecules 28:2944-54 (1995).
Back, D.M. et al., "Ethylene Oxide Polymers", in Kirk-Othmer Encyclopedia of Chemical Technology. 2000, John Wiley & Sons, Inc., vol. 10, 673-696.
Bailey, F.E., et al., "High Molecular Weight Polymers of Ethylene Oxide" Solution Properties Industrial and Engineering Chemistry 1958. 50(1): 8-11.

Balogh, E., "Tastes in and Tastes of Paprika," in Taste: Proceedings of the Oxford Symposium on Food and Cookery 28 (Tom Jaine Ed.) 1988, pp. 25-40.
Baumann, T., "Pain Management," Pharmacotherapy: A Pathophysiologic Approach (J.T. DiPiro et al. eds., McGraw-Hill 4th ed. 1999), Ch. 56, 1014-1026.
Baumrucker, S.J., "OxyContin, the Media, and Law Enforcement", American Journal of Hospice & Palliative Care, 18:3 (May/Jun. 2001), 154-156.
Choi, S., et al., "Development of a Directly Compressible Poly(Ethylene Oxide) Matrix for the Sustained-Release of Dihydrocodeine Bitartrate", Drug Development and Industrial Pharmacy, vol. 29, No. 10, pp. 1045-1052, 2003.
Choi, S., et al., "Hydrophilic Matrix Formulations of Dihydrocodeine Bitartrate with Polyethylene Oxide by Direct Compression," Proceedings of the $29^{th}$ Annual Meeting of the Controlled Release Society, in collaboration with the Korea Society for Biomaterials, Minneapolis, $1^{st}$ Edition, 2002, 984-985.
Ciccone, P. E., "Attempted Abuse of Concerta," Letters to the Editor, J. Am. Acad. Child Adolesc. Psychiatry, 41:7 (Jul. 2002).
Controversies in ADHD: A Breakfast Symposium—Concerta.
Crowley, M. et al., Pharmaceutical Applications of Hot-Melt Extrusion: Part I. Drug Dev. & Indus. Pharmacy (2007) 33:909-926.
Crowley, M. et al., "Properties of Hot-Melt Extruded CPM Tablets Using Hydrophilic Polymers," poster presentation, (2000).
Crowley, M., "Physicochemical and Mechanical Characterization of Hot-Melt Extruded Dosage Forms." Dissertation presented to the Faculty of the Graduate School of the University of Texas at Austin. (May 2003).
Crowley, M., et al,, "Evaluation of a Hot Melt Extrusion Technique using a Hydrophilic Thermal Polymer and Retardant for the Preparation of Extended Release Chlorpheniramine Maleate Tablets," in American Association of Pharmaceutical Scientists: Indianapolis, IN (2000).
Crowley0000001—Crowley0000127.
Davies, N. "Sustained Release and Enteric Coated NSAIDs: Are They Really GI Safe?" J. Pharm. & Pharmaceut. Sci., 2(1):5-14, 1999.
Declaration of Dr. James W. McGinity, dated Oct. 28, 2009; online, retrieved from: http://www.accessdata.fda.gov/dmgsatfda_docs/labeV2013/021121s032lbl.pdf.
Dimitrov, M, et al., "Study of Verapamil hydrochloride release from compressed hydrophilic Polyox-Wsr tablets." Int'l J Pharmaceutics (1999) 189:105-111.
Dittmer, D.K., et al., "Glue-Sniffing Neuropathies," Canadian Family Physician 39:1965-1971 (1993).
Donnelly, C.L., "ADHD Medications: Past and Future," Behavioral Health Management, May/Jun. 2002, 28 & 30.
Dow, "Material Safety Data Sheet: POLYOX(TM) WSR 30" (effective date: Sep. 18, 2001).
Dow, "POLYOX Water-Soluble Resins: Degradation of Water-Soluble Resins," Technical Data (Oct. 2002).
Drug Bank "Oxymorphone," 2015; online, available at: www.dmgbank.ca/chugs/db01192 printed Jul. 1, 2015.
*Endo Pharmaceuticals Inc. v. Teva Pharmaceuticals USA, Inc.* (S.D.N.Y 2015)—Redacted Version.
FDA News Release, "FDA approves abuse-deterrent labeling for reformulated OxyContin," Apr. 16, 2013, available at http://www.fda.gov/NewsEvents/Newsroom/Press.Announcements/ucm348252.htm.
FDA, "Notice of Determination that OxyContin Drug Products Covered by NDA 20-553 Were Withdrawn From Sale for Reasons of Safety or Effectiveness." Federal Register, vol. 78, No. 75, Apr. 18, 2013, 23273-23274.
Final Draft Labeling for Concerta Extended-Release Tablets Attachment to a Approval Letter (2000); available at: http://www.accessdata.fda.gov/drugsatfda_docs/label/2000/2112lbl.pdf.
Greenhill, L.L., et al., "Practice Parameter for the Use of Stimulant Medications in the Treatment of Children, Adolescents, and Adults," J. Am. Acad. Child Adolesc. Psychiatry, 41:2 Supplement, 26S-49S (Feb. 2002).
Griffith, D., "Potential new ADHD drug creating lots of big hopes," Sacramento Bee (California), Oct. 30, 2002.

(56) References Cited

OTHER PUBLICATIONS

Huang, H. et al., "Preparation of Controlled Release Oral Dosage Forms by Low Temperature. Melt Extrusion," AAPS PharmSci. 2000 2(S1).
Jaffe, S.L., "Failed Attempts at Intranasal Abuse of Concerta," Letters to the Editor, J. Am. Acad. Child Adolesc. Psychiatry, 41:1 (Jan. 2002).
Jannsen Pharmaceuticals, Inc. Concerta Labeling Revisioins, Dec. 12, 2013; online, retrieved from: http://www.accessdata.fda.gov/dmgsatfda_docs/labeV2013/021121s032lbl.pdf.
Joint Claim Construction and Prehearing Statement, dated Jul. 11, 2014. *Janssen Pharmaceuticals, Inc.* and *Grünenthal GMBH* v. *Actavis Elizabeth LLC* and *Alkem Laboratories Limited*, Civil Action No. 2:13-cv-04507 CCC-MF (D.N.J.), *Janssen Pharmaceuticals, Inc.* and *Grünenthal GMBH* v. *Roxane Laboratories, Inc.*, Civil Action No. 2:13-cv-06929 CCC-MF (D.N.J.), and *Janssen Pharmaceuticals, Inc.* and *Grünenthal GMBH* v. *Alkem Laboratories Limited*, Civil Action No. 2:13-cv-07803 CCC-MF (D.N.J.).
Kibbe, Coloring Agents, in Handbook of Pharmaceutical Excipients (3d ed. 2000).
Kidokoro, M. et al., "Properties of Tablets Containing Granulations of Ibuprofen and Acrylic Copolymers Prepared by Thermal Processes," Pharm Dev. and Tech. 6:263-275 (2001).
Kinjo, N. et al, "Antiplasticization in the Slightly Plasticized Poly(vinyl chloride)," Polymer Journal 4(2):143-153 (1973).
Larhib, H. et al., "Compressing polyethyelene glycols: the effect of compression pressure and speed," Int 'l J Pharmaceutics (1997) 147: 199-205.
Lieberman, H., et al., Pharmaceutical Dosage Forms: Tablets, vol. 2, Ch. 5: Granulation Technology and Tablet Characterization (1990), Table of contents and 245-348.
Lyons et al., "Twitch Interpolation in the Assessment of the Maximum Force-Generating Capacity of the Jaw-Closing Muscles in Man," Arch. Oral. Biol. 41:12, 1161-1168 (1996).
Makki, A, et. Al., Eds., A Dictionary of American Idioms, 4th Ed. Barron's, New York (2004), 342-343.
Markovitz, H., et al. "Calculations of Entanglement Coupling Spacings in Linear Polymers." Journal of Physical Chemistry, 1962. 66(8): 1567-1568.
McCrum, N., et al., Principles of Polymer Engineering. 2nd ed., New York: Oxford University Press. 447(1997), Chapter 7, 296-351.
McGinity, J.W. et al., "Melt-Extruded Controlled-Release Dosage Forms" in Pharmaceutical Extrusion Technology, Ghebre-Sellassie, I. and Martin, C., Eds., Marcel Dekker, Inc., New York, 2003, Chapter 10, 183-208.
McQuay, H. et a. "Methods of Therapeutic Trials," Textbook of Pain 1125-1138 (P.D. Wall & R. Melzack eds., Elsevier 4th ed. 1999), Table of Contents and 1125-1138.
Miura et al., "Comparison of Maximum Bite Force and Dentate Status Between Healthy and Frail Elderly Persons," J. Oral Rehabilitation, vol. 28 (2001), pp. 592-595.
Miyagawa, Y. et al., "Controlled-release of diclofenac sodium from wax matrix granulate," Int 'l J. Pharmaceutics (1996) 138:215-224.
National Drug Intelligence Center Information Bulletin "OxyContin Diversion and Abuse" Jan. 2001.
Payne, H. et al., Denatonium Benzoate as a Bitter Aversive Additive in Ethylene Glycol and Methanol-Based Automotive Products, SAE Technical Paper 930589, Abstract (1993).
Pilpel, N., et al. "The effect of temperature on the tensile strength and disintegration of paracetamol and oxytetracylcine tablets," J Pharm Pharmac., 29:389-392 (1977).
POLYOX Water-Soluble Resins NF in Pharmaceutical Applications, Dow Chemical Company, Aug. 2002.
Purdue Pharma LP Material Safety Data Sheet, OxyContin Tablets, 10 mg, 15 mg, 20 mg, 30 mg, 40 mg, 60 mg, Version 16—Sep. 16, 2010; available at www.purduephruma.com/msdss/oxycontin_msds.pdf.
Rauwendaal, Chris, PHD, Responsive Expert Report of Chris Rauwendaal, Ph.D., Regarding Expert Report of Michael M. Crowley, Ph.D., dated Jul. 17, 2015.
Repka, M. et al. Pharmaceutical Applications of Hot-Melt Extrusion: Part II. Drug Dev. & Indus, Pharmacy (2007) 33:1043-1057.
Saravanan, M. et al., "The Effect of Tablet Formulation and Hardness on in Vitro Release of Cephalexin from Eudragit L100 Based Extended Release of Tablets," Biol. Pharm. Bull. (2002) 25(4):541-545.
Seitz, J.A.; et al., "Evaluation of the Physical Properties of Compressed Tablets 1: Tablet Hardness and Friability," J. of Pharm. Sci., 54:1353-1357 (1965).
Shah, et al., "Some Effects of Humidity and Heat on the Tableting Properties of Microcrystalline Cellulose Formulations 1," J. of Pharm. Sci., 57:181- 182 (1967).
Singhal, et al., Handbook of Indices of Food Quality and Authenticity (1997), "Capsicum" p. 398-299.
Smith, K.L. et al. "High Molecular Weight Polymers of Ethylene Oxide—Plastic Properties." Industrial and Engineering Chemistry, 1958. 50(1): 12-16.
Tapentadol Pre-Review Report, Fifth Meeting on Drug Dependency Thirty-Fifth Meeting Hammamet, Tunisia, Jun. 4-8, 2012, available at http ://www.who.int/medicines/areas/quality_safety/5. 2Tapentadolpre-review.pdf.
Tiwari, D., et al., "Evaluation of polyoxyethylene homopolymers for buccal bioadhesive drug delivery Article formulations," AAPS Pharmsci, 1999. 1(3): Article 13.
Wilkins, J.N., "Pharmacotherapy of Schizophrenia Patients with Comorbid Substance Abuse," Schizophrenia Bulletin, 23:215-228 (1997).
World Health Org., Cancer Pain Relief With a Guide to Opioid Availability (2d ed. 1996).
Yin, T.P., et al., "Viscoelastic Journal of Physical Chemistry, Properties of Polyethylene Oxide in Rubber-Like State." 1961. 65(3): 534-538.
Zacny, J. et al. Drug & Alcohol Dependence (2003) 69:215-232.
Zhang, F., "Hot-Melt Extrusion as a Novel Technology to Prepare Sustained-Release Dosage Forms," Dissertation University of Texas at Austin, Dec. 1999.
Baxter, J.L. et al., "Hydrodynamics-induced variability in the USP apparatus II dissolution test," International Journal of Pharmaceutics 292 (2005) 17-28.
Bellmann et al., "Development of an advanced in vitro model of the stomach and its evaluation versus human gastric psychology." Food Research International 88 (2016) 191-198.
Extended European Search Report for Application No. EP 16183922.0-1460, dated Oct. 31, 2016.
Fathima, N. et al. "Drug-excipient interaction and its importance in dosage form development," Journal of Applied Pharmaceutical Science 01 (06); 2011, pp. 66-71.
Koziolek, M. et al., "Development of a bio-relevant dissolution test device simulating mechanical aspects present in the fed stomach," European Journal of Pharmaceutical Sciences 57 (2014) 250-256.
Meyer et al., "Awareness Topic: Mitigating the Risks of Ethanol Induced Dose Dumping from Oral Sustained/Controlled Release Dosage Forms," FDA ACPS Meeting, Oct. 2005, p. 1-4.
Remington, Chapter 45, pp. 996-1035. (Full Translation Attached).
Schilling, et al., "Novel application of hot-melt extrusion for the preparation of monolithic matrices containing enteric-coated particles." International Journal of Pharmaceutics 400 (2010) 34-31.
Starch 1500, Partially Pregelatinized Maize Starch, technical data from Colorcon, Feb. 2016, 6 pages.
Dabbagh, et al. "Release of Propranolol Hydrochloride from Matrix Tablets Containing Sodium Carboxymethylcellulose and Hydroxypropylmethylcellulose"; 1999; Pharmaceutical Development and Technology, 4(3), 313-324.
COMPAP 90 technical data sheet Mar. 2014; 1 page.
Extended European Search Report for Application No. EP 16182124.4-1455, dated Jan. 17, 2017.
USP Expert Council, US Pharmacopoeia, Chapter 1092, 2007, 1-15.
M. Xu et al., "Evaluation of the coat quality of sustained release pellets by iindividual pellet dissolution methodology," Int. J. Pharm. 478 (2015) 318-327.

(56) References Cited

OTHER PUBLICATIONS

Furu et al. "use of ADHD drugs in the Nordic countries: a population-based comparison study," Acta Psychiatrica Scandinavia, May 2010.
PCT International Search Report and Written Opinion for PCT Application No. PCT/EP2017/070396 dated Sep. 8, 2017.

* cited by examiner

TAMPER RESISTANT IMMEDIATE RELEASE CAPSULE FORMULATION COMPRISING TAPENTADOL

This application is a continuation of U.S. patent application Ser. No. 14/709,124, filed May 11, 2015, now pending, which claims priority of European Patent Applications EP 14 167 923.3, filed on May 12, 2014, and EP 14 176 277.3, filed on Jul. 9, 2014, the entire contents of which patent applications are incorporated herein by reference.

The claimed invention was made by, on behalf of, and/or in connection with the following parties to a joint research agreement: Grünenthal GmbH and R.P. Scherer Technologies, LLC. The agreement was in effect on and before the date the claimed invention was made, and the claimed invention was developed and made as a result of activities undertaken within the scope of the agreement.

The invention relates generally to an immediate release capsule formulation that is resistant to parenteral abuse of Tapentadol or a physiologically acceptable salt thereof.

Many active pharmaceutical ingredients, in addition to having an excellent activity in their appropriate application, also have potential for abuse, i.e. they can be used by an abuser to bring about effects other than those intended. For example, opioid analgesics, which are highly active in combating severe to very severe pain, are frequently used by abusers to induce a state of narcosis or euphoria. Typically, a particular dose of an opioid analgesic is more potent when administered parenterally as compared to the same dose administered orally. One popular mode of abuse of oral opioid formulations involves the extraction of the opioid from the dosage form, and the subsequent injection of the opioid (using any suitable vehicle for injection such as an insulin syringe) in order to achieve a "high".

This abuse problem is well known to the pharmaceutical and medical industries. Various methods of obviating such abuse have been devised.

GB 2 238 478 is directed to a pharmaceutical unit dosage form which comprises a soft gelatin capsule shell or a two-piece hard gelatin capsule filled with a benzodiazepine in a gel comprising at least 63% of polyethylene glycol 600, at least 4% by weight of polyethylene glycol 4000 or 6000 and at least 21% by weight of an intermediate polyethylene glycol. This purports to solve the abuse problem by using a formulation that is too viscous to be expelled from a syringe.

U.S. Pat. No. 7,230,005 is directed to solving the abuse problem discussed above by converting the active pharmaceutical ingredient to a poorly absorbed ester pro drug or other prodrug derivative prior to formulation. Mechanical processing of tablet or caplets containing the prodrug does not release the active API. The tablets and capsule beads containing prodrugs or other drugs can be formulated with a sufficient amount of a thickening agent to impede inappropriate intravenous administration of formulations that are not indicated for these modes of administration.

U.S. Pat. No. 7,399,488 is directed to an abuse-deterrent pharmaceutical composition wherein a drug is modified to increase its lipophilicity. In preferred embodiments the modified drug is homogeneously dispersed within microparticles composed of a material that is either slowly soluble or not soluble in water. In some embodiments the drug containing microparticles or drug particles are water insoluble, but enzymatically degradable by enzymes present in the human gastrointestinal tract.

U.S. Pat. No. 7,510,726 relates to an abuse deterrent dosage form of opioids, wherein an analgesically effective amount of opioid analgesic is combined with a polymer to form a matrix. The formation of a high-viscosity gel is a result of exposing the solid dosage form to water.

U.S. Pat. No. 7,776,314 relates to a solid administration form, protected from parenteral abuse and containing at least one viscosity-increasing agent in addition to one or more active substances that have parenteral abuse potential. The agent forms, when a necessary minimum amount of an aqueous liquid is added, on the basis of an extract obtained from the administration form, a preferably injectable gel that remains visually distinct when introduced into another quantity of an aqueous liquid.

U.S. Pat. No. 7,842,307 discloses oral dosage form comprising a therapeutically effective amount of an opioid analgesic, an opioid antagonist and one or more physiologically acceptable excipients. The dosage form further includes a gelling agent in an effective amount to impart a viscosity unsuitable for administration selected from the group consisting of parenteral and nasal administration to a solubilized mixture formed when the dosage form is crushed and mixed with from about 0.5 to about 10 ml of an aqueous liquid. The active pharmaceutical ingredient active pharmaceutical ingredient that is suspended in high viscosity solutions is unsuitable for abuse via intravenous injections.

U.S. Pat. No. 8,202,542 discloses a modified release tablet formulation of an opioid drug bound to an ion exchange resin, coated with a hybrid coating comprising a barrier coating containing a polyvinyl acetate polymer and a plasticizer and an enteric polymer mixed therewith.

U.S. 2005/152843 relates to a solid administration form, protected from parenteral abuse and containing at least one viscosity-increasing agent in addition to one or more active substances that have parenteral abuse potential. The agent forms, when a necessary minimum amount of an aqueous liquid is added, on the basis of an extract obtained from the administration form, a preferably injectable gel that remains visually distinct when introduced into another quantity of an aqueous liquid.

U.S. 2008/152595 relates to an abuse deterrent formulation of an oral dosage form of a therapeutically effective amount of any active drug substance that can be subject to abuse combined with a gel forming polymer, a nasal mucosal irritating surfactant and a flushing agent. Such a dosage form is intended to deter abuse of the active drug substance via injection, nasal inhalation or consumption of quantities of the dosage unit exceeding the usual therapeutically effective dose.

U.S. 2008/280975 discloses methods for preventing or minimizing the intensity of the serotonin syndrome in humans and lower animals which comprises administering proserotonergic agents and serotonin surge protectors.

U.S. 2009/0215808 is directed to oral pharmaceutical composition that is abuse-resistant, and its use to deliver the active pharmaceutical ingredient.

U.S. 2010/0099696 is directed to an oral dosage formulation containing a therapeutically effective amount of a drug susceptible to abuse and an effective amount of an embolizing agent which causes the production of a solid or semi-solid embolus or blockage alter tampering. The embolizing agent is a pH dependent polymer such as methacrylate, cellulose based polymer, and phthalate.

U.S. 2010/0249045 is directed to tamper resistant pharmaceutical compositions of opioids and extended release pharmaceutical compositions. All of the formulations appear to be for caplets.

EP 1 611 880 is directed to overcoming the abuse problem by providing pharmaceutical compositions of drugs known as replacement narcotics used in drug addiction therapy, such as methadone and/or its salts, preferably its hydrochloride, in a uniform soft-gel matrix to be taken orally without chewing, whereby the uniform matrix has the shape and size of a pill or capsule of a certain formulation. The formulation is entirely gelatinized, i.e., uniformly incorporated within the soft-gel matrix.

WO 2010/044842 is directed to solving the abuse problem by including an effective amount of embolizing agent (i.e., coagulating agent) which causes the production of a solid or semi-solid embolus or blockage alter tampering. Suitable examples of embolic agents are thrombin, cellulose diacetate polymer, albumin, gelatin, fibrinogen, 5 lactoglobulin, immunoglobulin, actin, acrylamide, polyacrylonitrile, polyurethane, polyvinylacetate, nitrocellulose and copolymers of urethane/carbonate and copolymers of styrene/maleic acid and pH sensitive polymers consisting of copolymers of methyl and butyl methacrylate and dimethylaminoethylmethacrylates.

WO 2010/066034 is directed to novel narcotic formulations having a decreased injection abuse potential. An oral pharmaceutical formulation is provided that makes the extraction of the active pharmaceutical ingredient more difficult, in particular in aqueous and alcohol solvents, and therefore prevents, or at least significantly reduces, the potential for abuse, while purportedly allowing the pharmaceutical formulation to release the active pharmaceutical ingredient in the gastrointestinal tract upon ingestion to allow for the desired pharmacological effect. The drug formulation is in form of a tablet, comprising a salt of the pharmaceutical active ingredient, and an alkalizing agent for reducing the solubility of the drug in no-acidic solutions.

WO 2010/105672 relates to a controlled release pharmaceutical composition, comprising a core, comprising a pharmaceutical active ingredient, whereby the core is coated by an ethanol resistance conferring coating layer which has the effect of conferring the release profile of the pharmaceutical active ingredient to be resistant against the influence of ethanol. The various coating techniques and formulations related thereto are taught.

WO 2011/128630 relates to an oral pharmaceutical composition comprising a physiologically tolerable gelled oil-in-water emulsion containing a drug of abuse.

WO 2013/003845 is directed to oral drug dosage forms designed to reduce the abuse potential of an oral dosage form of an opioid analgesic. The oral drug dosage form comprises a first population of drug-resin complex particles comprising an analgesically effective amount of an opioid drug coated with a water-permeable diffusion barrier coating; and a second population of ion exchange-resin complex particles comprising an aversive agent coated with a polymer coating sufficient to substantially prevent release of the aversive agent under normal use conditions. The abuse problem is addressed by using two different particles within the liquid or solid dosage form.

The abuse problem that the invention overcomes is based on illicitly obtaining the active pharmaceutical ingredient from a dosage form such as a capsule that comprises a capsule filling which in turn comprises the active pharmaceutical ingredient. Many drug abusers are able to separate the capsule filling from the capsule shell and to extract the active pharmaceutical ingredient by further treatment. Such treatment typically includes solubilizing the capsule filling with a small amount of water, such as about 5 mL of water per 1 capsule. This mixture is then heated, optionally boiled, and filtered through a filter, such as a cigarette filter, into a hypodermic syringe. Such a syringe may be an insulin syringe equipped with a needle. The syringes that are used for insulin injections typically comprise 20 to 31 gauge needles. Typically, due to viscosity challenges, the drug abuser will select a relatively thicker gauge needle such as a 20 gauge needle (about 0.91 mm outer diameter, 0.60 mm inner diameter).

There are many different methods how drug abusers recover the active pharmaceutical ingredients from capsules. Most of these techniques are neither well studied nor documented, due to their illicit nature.

It is an object of the invention to provide a tamper resistant pharmaceutical dosage form containing Tapentadol or a physiologically acceptable salt thereof having advantages compared to the dosage forms of the prior art. In particular, it is an object of the invention to provide a tamper resistant capsule comprising a capsule filling which when mixed with water and heated, results in a turbid, bubbling mixture that is not injectable with a standard insulin syringe.

This object has been achieved by the subject-matter of the patent claims.

A first aspect of the invention relates to a tamper resistant pharmaceutical capsule comprising a capsule filling and a capsule shell, wherein said capsule filling is encapsulated by said capsule shell and wherein said capsule filling comprises
(a) Tapentadol or a physiologically acceptable salt thereof in an amount within the range of from 10 mg to 400 mg, as equivalent weight relative to Tapentadol free base; and
(b) a liquid excipient blend comprising a solvent, a surfactant, and a viscosity enhancer; and
wherein the capsule provides immediate release of Tapentadol or the physiologically acceptable salt thereof upon oral administration.

The invention is directed to the development of an immediate release capsule formulation. More specifically, the invention is directed to an immediate release capsule formulation, which mitigates the abuse of Tapentadol or physiologically acceptable salt thereof by direct intravenous injection.

The invention addresses any of the above described illicit treatments of capsules that include heating or boiling of the capsule filling or of the capsule or of a dilution of the same, to obtain a mixture comprising Tapentadol or physiologically acceptable salt thereof, which can then be injected.

For illustrative purposes, the principles of the invention are described by referencing various exemplary embodiments. Although certain embodiments of the invention are specifically described herein, one of ordinary skill in the art will readily recognize that the same principles are equally applicable to, and can be employed in other systems and methods. Before explaining the disclosed embodiments of the invention in detail, it is to be understood that the invention is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

According to a preferred embodiment of the invention, the Tapentadol or physiologically acceptable salt thereof is dissolved or suspended in a self-emulsifying drug delivery system such as a lipophilic self-emulsifying drug delivery system that is not injectable with a standard insulin syringe.

The pharmaceutical capsule according to the invention comprises an outer capsule shell that encapsulates an inner capsule filling (inner core). Typically, the capsule shell completely surrounds the capsule filling so as hold the capsule filling. As the capsule filling comprises a liquid component, namely the liquid excipient blend, the capsule shell inter alia serves the purpose of containing the liquid excipient blend as well as the active pharmaceutical ingredient, namely Tapentadol or a physiologically acceptable salt thereof, and providing the capsule with a rigid outer shape such that is may be orally administered by a patient.

The tamper resistant capsule of the invention comprises the capsule shell and the capsule filling. The "capsule filling" is a liquid or semiliquid fluid that is encapsulated by the capsule shell. The composition of the capsule filling is formulated so that the capsule filling is tamper resistant thereby rendering the entire pharmaceutical capsule tamper resistant.

In a preferred embodiment, the pharmaceutical capsule according to the invention has a total weight within the range of from 200 to 2500 mg, more preferably 300 to 2000 mg, still more preferably 400 to 1800 mg, even more preferably 600 to 1600 mg, most preferably 700 to 1400 mg, and in particular 900 to 1300 mg.

In another preferred embodiment, the pharmaceutical capsule according to the invention has a total weight within the range of from 200 to 2500 mg, more preferably 300 to 2200 mg, still more preferably 700 to 1900 mg, even more preferably 900 to 1700 mg, most preferably 1100 to 1500 mg, and in particular 1200 to 1400 mg.

The parenteral tamper resistant capsule comprises a capsule shell that may comprise any suitable material that is known to form a capsule.

According to a preferred embodiment of the invention, the capsule is a soft capsule, such as a soft gelatin capsule. The shell may be formed from a combination of gelatin, water, and a plasticiser. Additional optional ingredients include an opacifier.

According to another embodiment of the invention, the capsule is a hard gelatin capsule. The hard gelatin capsule comprises two sections, one slipping over the other, thus completely enclosing the capsule filling. The hard gelatin capsule may be formed and filled by the capsule filling in any manner as known in the art. According to a preferred embodiment, the hard gelatin capsule is one that is exclusively designed to optimize liquid filling.

The composition of the capsule shell is such that it is compatible with the capsule filling.

Gelatin is a substantially pure protein food ingredient, obtained by the thermal denaturation of collagen, which is the most common structural material and most common protein in animals. Gelatin forms thermally reversible gels with water, and the gel melting temperature (<35° C.) is below that of human body temperature (37° C.), which gives gelatin products unique properties, such as reversible sol-gel transition states at near physiologic temperatures. Gelatin is an amphoteric protein with an isoionic point between 5 and 9, depending on raw material and method of manufacture. Type A gelatin, with an isoionic point of 7 to 9, is derived from Collagen with acid pretreatment. Type B gelatin, with an isoionic point of 4.8 to 5.2, is the result of alkaline pretreatment of the Collagen.

Examples of plasticizers include propylene glycol, glycerol, glycerin, sorbitol, and Anidrisorb.

Under another embodiment of the invention the shell is composed of a material that does not include gelatin. Exemplary components of non-gelatin capsules include modified starch, modified cellulose, substances derived from seaweed, and carrageenan.

The shell may be composed of substances that meet the ethical, cultural, dietary, or religious restrictions of the target consumer of the capsule. According to a preferred embodiment of the invention, the shell meets the Kosher standards. Under another embodiment of the invention the shell meets the Halal standards.

The pharmaceutical capsule according to the invention is filled with a capsule filling comprising Tapentadol or a physiologically acceptable salt thereof and a liquid excipient blend. The liquid excipient blend comprises a solvent, a surfactant, and a viscosity enhancer and optionally additional physiologically acceptable components so as to solubilize or miscibilize the Tapentadol or the physiologically acceptable salt thereof.

Preferably, the capsule filling consists of the Tapentadol or a physiologically acceptable salt thereof and the liquid excipient blend, i.e. does not contain any additional ingredients.

The mixture of Tapentadol or a physiologically acceptable salt thereof and the liquid excipient blend, i.e. the capsule filling, itself is preferably a liquid or semiliquid fluid. Said mixture may be a solution or dispersion. Dispersions may include suspensions, water in oil emulsions and oil in water emulsions. Solutions and suspensions are preferred. Emulsions (o/w and w/o) are included but less preferred.

In a preferred embodiment, the liquid excipient blend, i.e. the capsule filling, is a solution or a suspension wherein in case of a suspension the liquid phase thereof is preferably a single phase, e.g. is not further divided into an aqueous phase and an oil phase.

In a preferred embodiment, the liquid excipient blend, preferably the capsule filling, does not contain an oil in water emulsion.

In a preferred embodiment, the liquid excipient blend, preferably the capsule filling, does not contain a lipoid, lipid or oil. Thus, the liquid excipient blend, preferably the capsule filling, preferably does not contain a lipid phase or oil phase.

The liquid excipient blend comprises a solvent, a surfactant, and a viscosity enhancer. Optionally, the liquid excipient blend may comprise a plasticizer. Optionally, the liquid excipient blend may comprise an ion exchange resin.

Preferably, the capsule filling contained in the pharmaceutical capsule according to the invention has a total weight within the range of from 50 to 2000 mg, more preferably 100 to 1750 mg, still more preferably 250 to 1500 mg, even more preferably 500 to 1400 mg, most preferably 700 to 1200 mg, and in particular 900 to 1000 mg.

As discussed in the Experimental section below, the 1000 mg of excipients mixture has an excellent correlation to the tamper resistance characteristics of the capsule of capsule filling weight 950 mg. All excipient mixtures, which fulfilled tamper resistance showed good dispersibility, and worked with both amounts 250 and 1000 mg.

The pharmaceutical capsule according to the invention is tamper resistant (abuse resistant, abuse deterrent). For the purpose of the invention, "tamper resistant" means that the Tapentadol or physiologically acceptable salt thereof that is contained in the pharmaceutical capsule according to the invention may not be easily isolated from the pharmaceutical capsule and provided in a form suitable for parenteral administration by an abuser. The degree of tamper resistance is to at least impede parenteral abuse, preferably to make parenteral abuse practically impossible by means of techniques and devices that are typically available to an abuser. Preferably, "tamper resistant" means that it is difficult for an average drug abuser to take the necessary steps to isolate the Tapentadol or physiologically acceptable salt thereof from the capsule to the level necessary to administer the Tapentadol or physiologically acceptable salt thereof parenterally. The degree of difficulty in obtaining the Tapentadol or physiologically acceptable salt thereof ranges from impossibility (0% of the Tapentadol or physiologically acceptable salt thereof is delivered parenterally) to challenging (up to 33% of the Tapentadol or physiologically acceptable salt thereof is delivered parenterally). According to a preferred embodiment of the invention, the tamper resistant capsule filling provides no more than 33% of the Tapentadol or physiologically acceptable salt thereof for parenteral delivery.

The term "parenteral" as used in the phrase "parenteral tamper resistant capsule" means that the Tapentadol or physiologically acceptable salt thereof is introduced into the human body via a parenteral route. The term "parenteral" includes introduction of the Tapentadol or physiologically acceptable salt thereof into the body via an injection. Such injection may be intradermal, subcutaneous, transdermal, intravenous, or intramuscular. According to a preferred embodiment of the invention the term "parenteral" refers to "intravenous".

To test the tamper resistance, a weighed aliquot corresponding to the amount of capsule filling material is transferred to a metal tablespoon and mixed with 5 mL of purified water to create a mixture. This mixture is stirred with a spatula and then briefly heated to boiling over an open flame. After allowing the mixture to cool for about 1 minute, the mixture may be filtered through a cigarette filter. The filtrate is then aspirated into a 5 mL disposable syringe equipped with a 20 gauge, 25 mm long needle. Alternatively, the aqueous mixture (5 mL purified water) may be boiled and directly aspirated into the 5 mL syringe without prior filtering through a cigarette filter.

There are several different characteristics that may render the pharmaceutical capsule, particularly the capsule filling tamper resistant. One characteristic that renders the capsule filling tamper resistant is that its viscosity increases upon heating or boiling of the formulation in water. The viscosity of the mixture is increased to such a level that it is at least very difficult or even impossible to fill the insulin syringe with the mixture. According to a preferred embodiment of the invention, the viscosity of the heated mixture increases to a level that it may not be deliverable even through needles with the largest diameters commonly used in delivery of insulin.

The second characteristic that may render the pharmaceutical capsule, particularly the capsule filling tamper resistant is that upon heating or boiling the mixture of the capsule filling with water, bubbles occur in the mixture. The presence of such bubbles makes it more difficult to draw the mixture into the syringe. The bubbles also have a deterrent effect in that intravenous drug users tend to avoid introduction of air bubbles into their bloodstream due to their fear about air embolism.

Another aspect of the invention is a capsule comprising a parenteral tamper resistant capsule filling which when mixed with water and heated, results in a mixture which when filtered, the liquid extract preferably comprises at most 33 wt.-%, more preferably at most 25 wt.-%, still more preferably at most 20 wt.-%, even more preferably at most 15 wt.-%, most preferably at most 10 wt.-%, and in particular at most 5 wt.-% of the dosage of Tapentadol or a physiologically acceptable salt thereof originally contained in the pharmaceutical capsule.

Although there are many combinations of the capsule filling components that may work well to deliver the Tapentadol or physiologically acceptable salt thereof upon prescribed oral administration, it has been surprisingly found that only certain combinations of the capsule filling components additionally provide parenteral tamper resistance.

Preferably, the tamper resistant capsule according to the invention comprises a capsule shell and a capsule filling that in turn comprises
(a) Tapentadol or a physiologically acceptable salt thereof in an amount within the range of from 10 mg to 400 mg, as equivalent weight relative to Tapentadol free base; and
(b) a liquid excipient blend comprising a solvent, a surfactant, and a viscosity enhancer, such that a mixture of 250 milligrams of the liquid excipient blend with 5 milliliters of water at the mixture's boiling point forms a viscous phase which cannot pass through a 25 millimeter long needle having an inner diameter of 0.60 millimeters;
wherein the capsule provides immediate release of Tapentadol or the physiologically acceptable salt thereof upon oral administration.

Preferably, the tamper resistant capsule according to the invention comprises a capsule shell and a capsule filling that in turn comprises
(a) Tapentadol or a physiologically acceptable salt thereof in an amount within the range of from 10 mg to 400 mg, as equivalent weight relative to Tapentadol free base; and
(b) a liquid excipient blend comprising a solvent, a surfactant, and a viscosity enhancer, such that a mixture of 250 milligrams to 1000 milligrams of the liquid excipient blend with 5 milliliters of water at the mixture's boiling point forms a viscous phase which cannot pass through a 25 millimeter long needle having an inner diameter of 0.60 millimeters;
wherein the capsule provides immediate release of Tapentadol or the physiologically acceptable salt thereof upon oral administration.

Tapentadol is 3-[(1R,2R)-3-(Dimethylamino)-1-ethyl-2-methylpropyl]phenol having the following general formula:

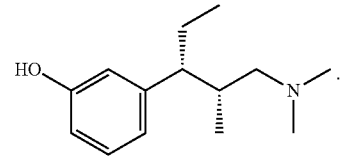

For the purpose of the specification, "Tapentadol or physiologically acceptable salt thereof" also includes a prodrug. The term "prodrug" means a compound that is a metabolic precursor to Tapentadol or a physiologically acceptable salt thereof. This precursor is transformed in vivo to provide Tapentadol or a physiologically acceptable salt thereof which has the desired therapeutic effect.

For the purpose of the specification, "physiologically acceptable salt" means a salt that is physiologically tolerable and that possesses the desired pharmacological activity of Tapentadol. Such salts include: acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and salts formed when an acidic proton present in the parent compound either is replaced by a metal ion, e.g., an alkali metal ion, an alkaline earth ion, or an aluminum ion; or coordinates with an organic Base such as ethanolamine, diethanolamine, triethanolamine, tromethamine, N-methylglucamine, and the like. Tapentadol hydrochloride is preferred.

For the purpose of the specification, "physiologically acceptable" means that which is useful in preparing a pharmaceutical composition that is generally safe, non-toxic, and neither biologically nor otherwise undesirable and includes that which is acceptable for human pharmaceutical use.

Furthermore, in addition to the above compounds, for the purpose of the specification, "Tapentadol or physiologically acceptable salt thereof" also includes a solvate of any of these compounds. The term "solvate" refers to an aggregate that comprises one or more molecules of Tapentadol or physiologically acceptable salt thereof with one or more molecules of a solvent. The solvent may be water, in which case the solvate may be a hydrate. Alternatively, the solvent may be an organic solvent. According to one definition, the term "solvate" refers to the Tapentadol or physiologically acceptable salt thereof in its state prior to the dissolution in the liquid excipient blend. According to another definition, the solid particles of the Tapentadol or physiologically acceptable salt thereof suspended in the liquid excipient blend may comprise a co-precipitated solvent.

The pharmaceutical capsule according to the invention comprises Tapentadol or a physiologically acceptable salt thereof, preferably Tapentadol hydrochloride, in an amount within the range of from 10 mg to 400 mg, as equivalent weight relative to Tapentadol free base. The amount of Tapentadol or a physiologically acceptable salt thereof is expressed as equivalent weight relative to Tapentadol free base. Thus, for example, an amount of 100 mg Tapentadol or a physiologically acceptable salt thereof correspond to about 116.48 mg Tapentadol hydrochloride.

Preferably, the amount of Tapentadol or a physiologically acceptable salt thereof, expressed as equivalent weight relative to Tapentadol free base, is within the range of 25±5 mg, 50±5 mg, 75±5 mg, 100±5 mg, 150±5 mg, 200±5 mg, or 250±5 mg.

Preferably, the total content of Tapentadol or physiologically acceptable salt thereof, as equivalent weight relative to Tapentadol free base, is within the range of from 0.1 to 25 wt.-%, more preferably 2.5 to 22.5 wt.-%, still more preferably 5 to 20 wt.-%, even more preferably 7.5 to 17.5 wt.-%, most preferably 10 to 15 wt.-%, and in particular 12 to 13 wt.-%, relative to the total weight of the capsule filling.

In a preferred embodiment, Tapentadol is present as the hydrochloride salt and the total content of Tapentadol hydrochloride is within the range of from 0.1 to 25 wt.-%, more preferably 2.5 to 22.5 wt.-%, still more preferably 5 to 20 wt.-%, even more preferably 7.5 to 17.5 wt.-%, most preferably 10 to 15 wt.-%, and in particular 12 to 13 wt.-%, relative to the total weight of the capsule filling.

The pharmaceutical capsule according to the invention provides immediate release of Tapentadol or a physiologically acceptable salt thereof. In this regard, immediate release is preferably understood as the opposite of prolonged release. Preferably, "immediate release" means within 30 minutes after oral administration a release of at least 80 wt.-%, more preferably at least 85 wt.-%, most preferably at least 90 wt.-% and in particular at least 95 wt.-% of the Tapentadol or physiologically acceptable salt thereof that was originally contained in the pharmaceutical capsule. The release profile may be tested under physiological conditions in simulated gastric fluid (e.g. in 900 ml 0.1 N HCl, at 75 rpm).

Preferably, the capsule filling comprises an ion exchange resin that creates an ion exchange complex with the Tapentadol or physiologically acceptable salt thereof that dissociates within 30 minutes within the gastrointestinal tract.

It has been surprisingly found that capsules comprising capsule fillings that show acceptable solubility properties and that comprise a colloidal anhydrous silica and a gum exhibit tamper resistant properties.

The parenteral tamper resistant capsule of the invention comprises a liquid excipient blend.

The term "excipient" as used herein refers to a compound that is useful in preparing a pharmaceutical composition, generally safe, non-toxic and neither biologically nor otherwise undesirable, and includes compounds that are acceptable for veterinary use as well as human pharmaceutical use.

The phrase "liquid excipient blend" means the capsule filling of the capsule except for Tapentadol or physiologically acceptable salt thereof. The liquid excipient blend comprises selected physiologically acceptable components such as a solvent, a surfactant, and a viscosity enhancer.

The liquid excipient blend may also comprise another active pharmaceutical ingredient that is not Tapentadol or physiologically acceptable salt thereof.

The liquid excipient blend comprises any physiologically acceptable components so as to solubilize or miscibilize the Tapentadol or physiologically acceptable salt thereof. The liquid excipient blend of the invention solubilizes or suspends the Tapentadol or physiologically acceptable salt thereof. The solubility of the Tapentadol or physiologically acceptable salt thereof must be sufficient to solubilize a therapeutically effective amount of the Tapentadol or physiologically acceptable salt thereof. Alternatively, the Tapentadol or physiologically acceptable salt thereof may form a stable suspension. The solubility of the Tapentadol or physiologically acceptable salt thereof may be determined by mixing equivalent of 25% of the therapeutically effective amount of Tapentadol or physiologically acceptable salt thereof in the liquid excipient blend. After stirring for 18 hours at 20 to 25° C., additional 25% of the Tapentadol or physiologically acceptable salt thereof is added. This last step is repeated until the saturation solubility is reached.

The liquid excipient blend of the invention balances at least three different properties: (1) solubilization; (2) tamper resistance; and (3) immediate release. Other additional considerations include long term stability, and ease of processing.

One of the components of the liquid excipient blend is a solvent or a carrier. The capsule filling may comprise more than one solvent. The solvent is any physiologically acceptable solvent that solubilizes the Tapentadol or physiologically acceptable salt thereof and the excipients.

The solvent is generally hydrophilic or amphiphilic. Exemplary solvents include water, polyethylene glycol, propylene glycol, medium chain triglycerides, corn oil monoand diglycerides, refined soybean oil, refined sesame oil, ethanol, phospholipid concentrates, poloxamers and medium chain partial glycerides.

The combination of water and polyethylene glycol is particularly preferred, wherein the relative weight ratio of water to polyethylene glycol is preferably within the range of from 1:100 to 1:10, more preferably 1:60 to 1:30.

Preferably, the total content of solvent is within the range of from 10 to 90 wt.-%, more preferably 20 to 85 wt.-%, still more preferably 30 to 80 wt.-%, yet more preferably 35 to 75 wt.-%, even more preferably 40 to 70 wt.-%, most preferably 45 to 65 wt.-% and in particular 50 to 60 wt.-%, relative to the total weight of the capsule filling.

When the solvent comprises water, the water content is preferably within the range of from 0.1 to 20 wt.-%, more preferably 0.3 to 15 wt.-%, still more preferably 0.5 to 10 wt.-%, yet more preferably 0.7 to 7.5 wt.-%, even more preferably 0.8 to 5.0 wt.-%, most preferably 0.9 to 2.5 wt.-% and in particular 1.0 to 1.5 wt.-%, relative to the total weight of the capsule filling.

Another component of the liquid excipient blend of the invention is a surfactant. The liquid excipient blend may comprise more than one surfactant. The surfactant is selected from any physiologically acceptable surfactants.

Preferably, the surfactant has a HLB value within the range of from 14±7, more preferably 14±5, most preferably 14±3, and in particular 14±1.

Preferably, the surfactant is nonionic.

In a preferred embodiment, the surfactant is a nonionic surfactant selected from the group consisting of glycerol monoesters with $C_{6-18}$-fatty acids, glycerol diesters with identical or different $C_{6-18}$-fatty acids, glycerol triesters with identical or different $C_{6-18}$-fatty acids, polyethylene glycol monoesters with $C_{6-18}$-fatty acids, polyethylene glycol diesters with identical or different $C_{6-18}$-fatty acids, and mixtures of any of the foregoing.

In another preferred embodiment, the surfactant is selected from the group consisting of polyoxyethylene (20) sorbitanmonolaurate, polyoxyethylene (20) sorbitanmonopalmitate, polyoxyethylene (20) sorbitanmonostearate, and polyoxyethylene (20) sorbitanmonooleate.

Exemplary surfactants include but are not limited to Polysorbate 20, Polysorbate 80, Tween 20, Tween 80, Macrogolglycerolhydroxystearate, Cremophor RH 40®, Macrogolglycerolricinoleate, Cremophor EL®, glycerolmonooleate 40, Peceolo, Macrogolglyceryl, Labrafil M 2125 CS, propyleneglycolmonolaurate FCC, Lauroglycol FCC®, Polyglycerol-b-Dioleate, propylenglycolmonocaprylate, Capryol 900, sorbitanmonolaurate, Span 200, sorbitanmonooleate, Span 800, Vitamin E-polyethylenglycolsuccinate, caprylocaproyl macrogol-8-glycerides, Labrasol®, macrogol-32-glycerol-laurate, Gelucire 44/14, glycerylmonocaprate, glycerylcaprylate, and Capmul MCM.

Preferably, the total content of surfactant is within the range of from 0.1 to 35 wt.-%, more preferably 1.0 to 32.5 wt.-%, still more preferably 5.0 to 30 wt.-%, yet more preferably 7.5 to 27.5 wt.-%, even more preferably 10 to 25 wt.-%, most preferably 12.5 to 22.5 wt.-%, and in particular 15 to 20 wt.-%, relative to the total weight of the capsule filling.

Another component of the liquid excipient blend of the invention is a viscosity enhancer, or a gelling agent. Exemplary viscosity enhancers include but are not limited to colloidal anhydrous silica, gum, and hard fat. Preferably, the viscosity enhancer comprises colloidal anhydrous silica and/or a gum.

Examples of gum include but are not limited to acacia, agar, tragacanth, guar gum, xanthan gum, locust bean gum, tara gum, karaya, gellan gum, welan gum, and rhamsan gum.

In a preferred embodiment, the liquid excipient blend comprises a combination of two viscosity enhancers, more preferably colloidal anhydrous silica in combination with a gum, more preferably colloidal anhydrous silica in combination with a gum selected from the group consisting of acacia, agar, tragacanth, guar gum, xanthan gum, locust bean gum, tara gum, karaya, gellan gum, welan gum, and rhamsan gum, and in particular colloidal anhydrous silica in combination with xanthan gum.

When the liquid excipient blend comprises a combination of colloidal anhydrous silica with a gum such as xanthan gum, the relative weight ratio of silica to gum is preferably within the range of from 1:1 to 20:1, more preferably 5:1 to 10:1.

Preferably, the total content of viscosity enhancer is within the range of from 0.1 to 10 wt.-%, more preferably, still more preferably relative to the total weight of the capsule filling.

In a preferred embodiment, the liquid excipient blend comprises an ion exchange resin. Preferably, the ion exchange resin is anionic, i.e. bears anionic functional groups that are linked, preferably covalently to a resin. Suitable anionic functional groups include but are not limited to carboxylic acid groups and sulfonic acid groups.

Preferably, the total content of ion exchange resin is within the range of from 0.1 to 25 wt.-%, more preferably 1.0 to 20 wt.-%, still more preferably 2.5 to 15 wt.-%, yet more preferably 5.0 to 12.5 wt.-%, even more preferably 6.0 to 11 wt.-%, most preferably 7.0 to 10 wt.-% and in particular 8.0 to 9.0 wt.-%, relative to the total weight of the capsule filling.

In a preferred embodiment, the liquid excipient blend comprises a plasticizer.

Examples of plasticizers include propylene glycol, glycerol, glycerin, sorbitol, and Anidrisorb. Glycerin is particularly preferred.

Preferably, the total content of plasticizer is within the range of from 0.1 to 25 wt.-%, more preferably 0.2 to 20 wt.-%, still more preferably 0.5 to 17.5 wt.-%, yet more preferably 1.0 to 15 wt.-%, even more preferably 2.0 to 12.5 wt.-%, most preferably 3.0 to 10 wt.-% and in particular 4.0 to 6.0 wt.-%, relative to the total weight of the capsule filling.

It is surprising that parenteral tamper resistant capsule fillings that show acceptable solubility properties and that comprise a colloidal anhydrous silica and a gum exhibit tamper resistant properties.

Such formulations include solvents such as medium chain triglycerides. Formulations that comprise medium chain triglycerides, colloidal anhydrous silica, and xanthan, preferably also include a polysorbate surfactant.

Other solvent and surfactant combinations in the liquid excipient blend that show surprising and unexpected tamper resistant properties when colloidal anhydrous silica and xanthan is present, include polyethylene glycol, and a surfactant selected from the group consisting of polyoxyl 40 hydrogenated castor oil, polysorbate surfactant, caprylocaproyl macrogol-8-glyceride, and glycerol. Examples of polyethylene glycol include Macrogol 400 and Macrogol 600.

Furthermore, it was unexpected and surprising to find that the liquid excipient blend comprising a phospholipid concentrate and a polysorbate surfactant also exhibit acceptable solubility and tamper resistance. The polysorbate surfactant in the formulation that exhibit the tamper resistant properties include polyoxyethylene (20) sorbitanmonolaurate, polyoxyethylene (20) sorbitanmonopalmitate, polyoxyethylene (20) sorbitanmonostearate, and polyoxyethylene(20) sorbitanmonooleate. Examples of phospholipid concentrates include Phosal 50 PG, and Lipoid PPL 600. For selected formulations, the use of a viscosity enhancer (colloidal anhydrous silica 0.5 to 1.5 wt %) was found to be helpful in order to achieve tamper resistance.

Yet another unexpected and surprising combination of liquid excipient blend components that exhibit solubility and abuse resistance is liquid excipient blend comprising polyethylene glycol, caprylocaproyl macrogol-8-glycerides, glycerol, and a viscosity enhancer. The viscosity enhancer may be a mixture of colloidal anhydrous silica and a gum.

Two examples of formulations that exhibit the desired properties are particularly preferred. One of the formulations comprises xanthan, the other pharmaceutical grade ion exchange resin such as Amberlite IR.P 64. The immediate release dissolution (in 0.1 N HCl, at 75 rpm) showed that more than 80% of Tapentadol from either of the formulations was dissolved after 30 minutes. Both formulations showed that not more than 33% of Tapentadol was detectable in syringe after boiling of the capsule filling with 5 ml water.

The formulations of Inventive Examples 16 and 18 comprise Medium Chain Triglycerides (27.3% and 28.2%, respectively), Polysorbate 80 (50.9%, 52.7%), Span 20 (12.7%, 13.2%), Colloidal anhydrous silica (4.5%, 3.5%), and xanthan gum (4.5%, 2.7%). These compositions are yellowish, homogeneous, liquid suspensions, which formed a gel and non-stable bubbles at boiling with water. 250 and 1000 g of the capsule filling could hardly be drawn up in the syringe and formed of a milky foam. Both formulations showed good dispersibility after disintegration of capsules (4.5 minutes). Approximately 80% of the Tapentadol was dissolved after 20 to 25 minutes and 100% after approx. 30 minutes.

Other solvent and surfactant combinations in the liquid excipient blend that show surprising and unexpected tamper resistant properties when colloidal anhydrous silica and xanthan is present, include polyethylene glycol, and a surfactant selected from the group consisting of polyoxyl 40 hydrogenated castor oil, polysorbate surfactant, caprylocaproyl macrogol-8-glyceride, and glycerol. Examples of polyethylene glycol include Macrogol 400 and Macrogol 600.

The 3:1 mixtures of Macrogol 400 with the surfactants Cremophor RH 40, Polysorbat 80 and Labrasol in Inventive Examples Nos. 30, 31, and 32 and Colloidal anhydrous Silica/Xanthan as gelling agents gave yellowish homogeneous suspensions, which formed a gel and a partially persisting foam at boiling in the water. The solution was not syringable but the dispersibility of the gel was poor due to formation of a compact mass after 6 minutes in the dispersion medium.

Tamper resistant properties were also observed with the use of replacing Macrogol 400 (see Comparative Example 35) by Macrogol 600 and xanthan. An intensive frothing milky emulsion resulted after boiling with water, which was not syringable. Both selected formulations of Examples 35 and 36 were easily dispersible in 0.1 N HCl at 100 rpm 80% of the capsule filling were dissolved after 20 minutes and 100% after 30 minutes.

Two examples of formulations according to the invention that exhibit the desired properties and that include Tapentadol or a physiologically acceptable salt thereof are particularly preferred. One of the formulations comprises xanthan (Formulation B), the other pharmaceutical grade ion exchange resin Amberlite IRP 64 (Formulation A). Preferred formulations comprise about 50% to 60% polyethylene glycol, 15% to 20% Caprylocaproyl Macrogol-8-glycerides, 3 to 6% colloidal anhydrous silica, 3 to 6% glycerol, 1% to 2% water. Formulation A comprises Macrogol 600 Ph. Eur. (479.02 mg/capsule, 51.0% of fill), Caprylocaproyl Macrogol-8-glycerides Ph.Eur. (160.00 mg, 17.0%), Colloidal anhydrous Silica Ph.Eur.(45.00 mg, 4.8%), Glycerol, anhydrous Ph. Eur. (47.00 mg, 5.0%), Water, purifed; Ph.Eur. (12.50 mg, 1.3%), and Amberlite IRP 64 (80.00 mg, 8.5%). Formulation B comprises Macrogol 600 Ph. Eur. (554.2 mg/capsule, 58.3% of fill), Caprylocaproyl Macrogol-8-glycerides Ph.Eur. (175.00 mg, 18.4%), Colloidal anhydrous Silica Ph.Eur.(40.00 mg, 4.2%), Glycerol, anhydrous Ph. Eur. (47.00 mg, 4.9%), Water, purified, Ph.Eur.(12.50 mg, 1.3%), and xanthan (5.00 mg, 0.5%). The capsule shell comprises Glycerol 85% Ph.Eur.: 106.43 mg (97.92-114.94 mg), Dry substance of Anidrisorb 85/70: 30.87 mg (28.40-33.34 mg); Gelatin 160 bloom. Ph.Eur. NF (bovine, kosher, Halal) 244.17 mg (224.64-263.70 mg).

It is hypothesized that in the above formulations each of the components has a specific function. Macrogol 600 is hydrophilic solvent agent for the water soluble drugs. Caprylocaproylmacrogol 8 glycerides are a hydrophilic surfactant (HLB 14) and solvent that improves dissolution and bioavailability, and causes bubbling at boiling of the capsule capsule filling with water. Colloidal anhydrous silica is a viscosity enhancer in order to stabilize the hydrophilic fall suspension. Glycerol is a plasticizer in the capsule filling to reduce migration effects from shell to the capsule filling.

Water increases drug solubility, reduces gelling agent concentration with positive effect on immediate release dissolution properties.

With respect to xanthan in formulation B, it is hypothesized that this hydrogelling agent is suspended in the capsule fill, but at boiling of the capsule capsule filling with hot water, it forms highly viscous gels as physical barrier. This reduces syringability and injectability.

With respect to Amberlite IRP 64 in formulation A, it is hypothesized that the HCl salt of the quarternary ammonium ion of the active substance forms a drug ion exchange complex with a weak acidic cationic resin (—COOH group) in Amberlite IRP 64. This ion pair complex is stable in the formulation, but is immediately released in the stomach environment, as the —COOH group of the resin has a high affinity to the $H^+$ Ions present in the stomach, Additionally to this fast release of the Tapentadol or physiologically acceptable salt thereof in 0.1 N HCl, an increase of the viscosity at boiling of the formulations containing the Polyacrilex resin was achieved. Amberlite IRP64 is inducted in the FDA inactive ingredients list under Polacrilin and already used in human drugs.

The following results of the relevant parameters in vitro dissolution and abuse resistance test (syringability) have been obtained. The immediate release dissolution (in 0.1 N HCl, at 75 rpm) showed that more than 80% of either of the formulations was dissolved after 30 minutes.

Another aspect of the invention relates to the capsule according to the invention as described above for use in the treatment of pain, preferably acute pain, preferably by oral administration.

Another aspect of the invention relates to a method of treating pain, preferably acute pain, comprising the preferably oral administration to a capsule according to the invention as described above to a subject in need thereof.

Another aspect of the invention relates to the use of the capsule according to the invention for preventing parenteral abuse of Tapentadol or a physiologically acceptable salt thereof.

EXAMPLES

The following examples further illustrate the invention but are not to be construed as limiting its scope.
Part a) Capsule Fillings—Liquid Excipient Blends Comparative Example 1

15.8 g of medium chain triglycerides, 2.5 g of hydrogenated soya bean oil, 41.7 g of hard fat, 3.3 g of Povidone K 30, and 3.3 g of polyoxyl 40 hydrogenated castor oil were mixed to obtain a homogenous mixture. The mixture was firm at room temperature, and flowable and pourable at 30° C. When the mixture is boiled with water (ca. 250 mg of the mixture in 5 mL of water), hard fat separates on cooling down. No air bubbles were formed at boiling. The aqueous phase was syringable with a 20 gauge needle, whereas small particles of hard fat were also observed in the syringe. After disintegration of the shell of lab filled capsules at about 25 minutes, the fall was dispersed with remaining fat particles in the dissolution medium and oil film on the surface.

Comparative Example 2

15.8 g of medium chain triglycerides, 2.5 g of hydrogenated soya bean oil, 41.7 g of hard fat, 3.3 g of Povidone K 30, and 3.3 g of polysorbate 80 h were mixed to obtain a homogenous mixture. 30 The mixture was firm at room temperature, and flowable and pourable at 30° C. When the mixture is boiled with water, hard fat separates on cooling down. No air bubbles were formed at boiling and the aqueous phase was syringable, whereas small particles of hard fat were also observed in the syringe. After disintegration of the shell at about 25 minutes, the capsule filling was dispersed with remaining fat particles in the dissolution medium and oil film on the surface.

Comparative Example 3

15.8 g of medium chain triglycerides, 2.5 g of hydrogenated soya bean oil, 41.7 g of hard fat, 3.3 g of Povidone K 30, and 3.3 g of polyoxyl 35 castor oil were mixed to obtain a homogenous mixture. The mixture was firm at room temperature, and flowable and pourable at 30° C. When the mixture is boiled with water, hard fat separates on cooling down. No air bubbles were formed at boiling and the aqueous phase was syringable, whereas small particles of hard fat were also observed in the syringe. After disintegration of the shell at about 25 minutes, the capsule filling was dispersed with remaining fat particles in the dissolution medium and oil film on the surface.

Comparative Example 4

45.0 g of medium chain triglycerides, 10.0 g of hydrogenated soya bean oil, and 10.4 g of polyoxyl 40 hydrogenated castor oil were mixed to obtain a homogenous mixture. The mixture was soft, flowable and pourable at room temperature. The sample exhibits a sheen of oil and sedimentation.

Comparative Example 5

45.0 g of medium chain triglycerides, 10.0 g of hydrogenated soya bean oil, and 10.0 g of polysorbate 80 were mixed to obtain a homogenous mixture. The mixture was soft, flowable and pourable at room temperature. The sample exhibits a sheen of oil and sedimentation.

Comparative Example 6

45.0 g of medium chain triglycerides, 10.0 g of hydrogenated soya bean oil, and 10.0 g of polyoxyl 35 castor oil were mixed to obtain a homogenous mixture. The mixture was soft, flowable and pourable at room temperature. The sample exhibits a sheen of oil and sedimentation.

Comparative Example 7

10.0 g of medium chain triglycerides and 40.0 g of polysorbate 80 were mixed to obtain a homogenous mixture. The mixture was a clear yellowish solution. When the solution is boiled with water, no frothing is observed.

Comparative Example 8

41.0 g of caprylocaproyl macrogol-8-glyceride, 6.5 g of medium chain triglycerides, and 2.5 g of polyglycerol-6-dioleate were mixed to obtain a clear yellowish solution. Upon addition of water, a white emulsion is obtained. No frothing is observed upon boiling with water.

Comparative Example 9

8.0 g of medium chain triglycerides, 25.6 g of polysorbate 80, and 6.4 g of sorbitanmonolaurate were mixed to obtain a homogenous mixture. The mixture was a clear yellowish solution. Upon addition of water, a turbid solution is obtained. Little frothing is observed upon boiling with water. The turbid solution can be drawn up into the syringe with little frothing.

Comparative Example 10

12.0 g of medium chain triglycerides, 22.4 g of polysorbate 80, and 5.6 g of sorbitanmonolaurate were mixed to obtain a homogenous mixture. The mixture was a clear yellowish solution. Upon addition of water, an almost clear solution is obtained. Little frothing is observed upon boiling with water. The solution can be drawn up into the syringe with little frothing.

Comparative Example 11

16.0 g of medium chain triglycerides, 19.2 g of polysorbate 80, and 4.8 g of sorbitanmonolaurate were mixed to obtain a homogenous mixture. The mixture was a clear yellowish solution. Upon addition of water, a turbid solution is obtained. Little frothing is observed upon boiling with water. The milky solution can be drawn up into the syringe with little frothing.

Comparative Example 12

20.0 g of medium chain triglycerides, 16.0 g of polysorbate 80, and 4.0 g of sorbitanmonolaurate were mixed to obtain a homogenous mixture. The mixture was a clear yellowish solution. Upon addition of water, a white emulsion is obtained. Little frothing is observed upon boiling with water. The milky emulsion can be drawn up into the syringe with little frothing.

Comparative Example 13

24.0 g of medium chain triglycerides, 12.8 g of polysorbate 80, and 3.2 g of sorbitanmonolaurate were mixed to obtain a homogenous mixture. The mixture was a clear yellowish solution. Upon addition of water, a white emulsion is obtained. Little frothing is observed upon boiling with water. The milky emulsion can be drawn up into the syringe with little frothing.

Inventive Example 14

12.0 g of medium chain triglycerides, 22.4 g of polysorbate 80, 5.6 g of sorbitanmonolaurate, 1.5 g of colloidal anhydrous silica, and 4.0 g of xanthan were mixed to obtain a homogenous yellowish suspension that is a pourable liquid. Upon addition of water, the suspension forms a gel. Upon boiling with water, frothing is observed, but the foam does not persist. The solution cannot be drawn up into the syringe. The yellowish suspension was used to fill a tube-shaped capsule. The capsule was then tested for dispersibility in 0.1 N HCl with the Paddle dissolution apparatus at 100 rpm, after about 20 minutes, about 40% if the capsule filling dispersed.

Comparative Example 15

12.0 g of medium chain triglycerides, 22.4 g of polysorbate 80, 5.6 g of sorbitanmonolaurate, and 2.0 g of colloidal anhydrous silica were mixed to obtain a yellowish gel that is almost clean. Upon addition of water, a white emulsion forms. Upon boiling with water, little frothing is observed. The milky solution can be drawn up into the syringe.

Inventive Example 16

12.0 g of medium chain triglycerides, 22.4 g of polysorbate 80, 5.6 g of sorbitanmonolaurate, 2.0 g of colloidal anhydrous silica, and 2.0 g of xanthan were mixed to obtain a homogenous yellowish suspension that is pourable. Upon addition of water, a gel forms. Upon boiling with water, frothing is observed and the foam does not persist. The milky solution can hardly be drawn up into the syringe. At higher concentration of the suspension (1 g in 5 mL of water), the resulting mixture exhibits very strong frothing, and the mixture cannot be drawn into the syringe. The yellowish suspension was tested for dispersibility. After about 4.5 minutes the capsule opened; after about 20 to 25 minutes about 80% of the capsule filling dissolved. After about 30 to 35 minutes 100% of the capsule filling was dissolved.

Inventive Example 17

12.0 g of medium chain triglycerides, 22.4 g of polysorbate 80, 5.6 g of sorbitanmonolaurate, 1.5 g of colloidal anhydrous silica, and 1.5 g of xanthan were mixed to obtain a homogenous yellowish suspension that is pourable. Upon addition of water, a gel forms. Upon boiling with water, frothing is observed and the foam does not persist. The milky solution can hardly be drawn up into the syringe. At higher concentration of the suspension, the resulting mixture exhibits very strong frothing, and the mixture can hardly be drawn into the syringe. The foam can be pressed out.

Inventive Example 18

12.0 g of medium chain triglycerides, 22.4 g of polysorbate 80, 5.6 g of sorbitanmonolaurate, 1.5 g of colloidal anhydrous silica, and 1.0 g of xanthan were mixed to obtain a homogenous yellowish suspension that is pourable. Upon addition of water, a gel forms. Upon boiling with water, frothing is observed and the foam does not persist. The milky solution can hardly be drawn up into die syringe. At higher concentration of the suspension, the resulting mixture exhibits very strong frothing, and the mixture can hardly be drawn into the syringe. The foam can be pressed out. The yellowish suspension was tested for dispersibility. After about 4.5 minutes the capsule opened; after about 20 to 25 minutes about 80% of the capsule filling dissolved. After about 30 to 35 minutes 100% of the fit was dissolved.

Comparative Example 19

42.5 g of macrogol 400, 6.3 g of medium chain triglycerides, 6.3 g of polysorbate 80, and 1.3 g of colloidal anhydrous silica were mixed to obtain an opalescent, yellowish solution. Upon addition of water, a white emulsion is obtained. Upon boiling with water, no frothing is observed.

Comparative Example 20

42.5 g of macrogol 400, 6.3 g of medium chain triglycerides, 6.3 g of polyoxyl 40 hydrogenated castor oil, and 1.3 g of colloidal anhydrous silica were mixed to obtain an opalescent, yellowish solution. Upon addition of water, a white emulsion is obtained. Upon boiling with water, no frothing is observed.

Comparative Example 21

42.5 g of macrogol 400, 6.3 g of medium chain triglycerides, 6.3 g of polyoxyl 35 castor oil, and 1.3 g of colloidal anhydrous silica were mixed to obtain an opalescent, yellowish solution. Upon addition of water, a white emulsion is obtained. Upon boiling with water, no frothing is observed.

Comparative Example 22

38.8 g of macrogol 400, 6.3 g of propylene glycol, 2.5 g of water, 6.3 g of polysorbate 80, and 2.5 g of Povidone K 30 were mixed to obtain a pale yellow, turbid solution that separated.

Comparative Example 23

38.8 g of macrogol 400, 6.3 g of propylene glycol, 2.5 g of water, 6.3 g of polysorbate 20, and 2.5 g of Povidone K 30 were mixed to obtain a homogenous pale yellow, turbid solution. Upon addition of water, a clean solution is obtained. Upon boiling with water, no frothing is observed.

Comparative Example 24

38.8 g of macrogol 400, 6.3 g of propylene glycol, 2.5 g of water, 6.3 g of polyoxyl 40 hydrogenated castor oil, and 2.5 g of Povidone K 30 were mixed to obtain a homogenous pale yellow, almost clear solution. Upon addition of water, a clear solution is obtained. Upon boiling with water, no frothing is observed.

Comparative Example 25

38.8 g of macrogol 600, 6.3 g of propylene glycol, 2.5 g of water, 6.3 g of polysorbate 80, and 2.5 g of Povidone K 30 were mixed to obtain a pale yellow, turbid solution that separated.

Comparative Example 26

38.8 g of macrogol 600, 6.3 g of propylene glycol, 2.5 g of water, 6.3 g of polysorbate 80, and 2.5 g of Povidone K 30 were mixed to obtain a pale yellow, turbid solution that separated.

Comparative Example 27

35.0 g of macrogol 600, 6.3 g of propylene glycol, 2.5 g of water, 6.3 g of polyoxyl 35 castor oil, and 6.3 g of xanthan gum were mixed to a mixture that separated and sedimented.

Comparative Example 28

35.0 g of macrogol 600, 6.3 g of propylene glycol, 2.5 g of water, 6.3 g of polysorbate 20, and 6.3 g of xanthan gum were mixed to a mixture that separated and sedimented.

Comparative Example 29

35.0 g of macrogol 600, 6.3 g of propylene glycol, 2.5 g of water, 6.3 g of polyoxyl 40 hydrogenated castor oil, and 6.3 g of xanthan gum were mixed to a mixture that separated and sedimented.

Inventive Example 30

30.0 g of macrogol 400, 10.0 g of polyoxyl 40 hydrogenated castor oil, 5.0 g of xanthan gum, and 1.0 g of colloidal anhydrous silica were mixed to obtain a homogeneous yellowish suspension that is pourable. The suspension forms a gel when mixed with water. Upon boiling, the gel froths, wherein the foam partially persists. The resulting solution cannot be drawn up in a syringe. The yellowish suspension was tested for dispersibility. After about 60 minutes the capsule filling is a compact mass, with less than 50% of the capsule filling dissolved.

Inventive Example 31

30.0 g of macrogol 400, 10.0 g of polysorbate 80, 5.0 g of xanthan gum, and 1.0 g of colloidal anhydrous silica were mixed to obtain a homogeneous yellowish suspension that is pourable. The suspension forms a gel when mixed with water. Upon boiling, the gel froths, wherein the foam does not persist. The resulting solution cannot be drawn up in a syringe. The yellowish suspension was tested for dispersibility as above. After about 60 minutes the capsule filling 25 is a compact mass, with less than 50% of the capsule filling dissolved.

Inventive Example 32

30.0 g of macrogol 400, 10.0 g of caprylocaproyl macrogol-8-glyceride, 5.0 g of xanthan gum, and 1.0 g of colloidal anhydrous silica were mixed to obtain a homogeneous yellowish suspension that is pourable. The suspension forms a gel when mixed with water. Upon boiling, the gel froths, wherein the foam partially persists. The resulting solution cannot be drawn up in a syringe. The yellowish suspension was tested for dispersibility as above. After about 60 minutes the capsule filling is a compact mass, with less than 50% of the capsule filling dissolved.

Comparative Example 33

30.0 g of macrogol 400, 10.0 g of polyxyl 40 hydrogenated castor oil, and 2.0 g of colloidal anhydrous silica were mixed to obtain a colorless gel that is pourable. The gel forms a white emulsion when mixed with water. Upon boiling, no frothing is observed. The resulting solution cannot be drawn up in a syringe. The formulation was tested for dispersibility as above. After about 20 minutes, about 90% of the capsule filling dispersed.

Comparative Example 34

30.0 g of macrogol 400, 10.0 g of polysorbate 80, and 2.0 g of colloidal anhydrous silica were mixed to obtain a turbid yellowish gel that is barely pourable. The gel forms a white emulsion when mixed with water. Upon boiling, no frothing is observed. The resulting solution can be drawn up in a syringe. The formulation was tested for dispersibility as above. After about 20 minutes, about 80% of the capsule filling dispersed.

Comparative Example 35

30.0 g of macrogol 400, 10.0 g of caprylocaproyl macrogol-8-glyceride, and 2.0 g of colloidal anhydrous silica were mixed to obtain a clear yellowish gel that is pourable. The gel forms a white emulsion when mixed with water. Upon boiling, strong frothing is observed. The resulting solution can be drawn up in a syringe. For the higher concentration of the formulation in water, the resulting milky emulsion exhibits strong frothing and can be drawn up into the syringe. The dispersibility test showed that after about 20 minutes 80% of the capsule filling was dissolved, and after 30 minutes, all of the capsule filling was dissolved.

Inventive Example 36

30.0 g of macrogol 400, 10.0 g of caprylocaproyl macrogol-8-glyceride, 2.0 g of colloidal anhydrous silica, and 0.8 g of xanthan were mixed to obtain a turbid yellowish gel that is barely pourable. The mixture forms a gel when mixed with water. Upon boiling, little frothing is observed. The resulting mixture can be drawn up in a syringe. For the higher concentration of the formulation in water, the resulting mixture cannot be drawn up into the syringe, with strong frothing

Inventive Example 37

30.0 g of macrogol 400, 10.0 g of caprylocaproyl macrogol-8-glyceride, 2.0 g of colloidal anhydrous silica, and 2.0 g of xanthan were mixed to obtain a turbid yellowish gel that is barely pourable. The mixture forms a gel when mixed with water. Upon boiling, little frothing is observed. The resulting mixture can be drawn up in a syringe. For the higher concentration of the formulation in water, the resulting mixture cannot be drawn up into the syringe, with strong frothing. The dispersibility test showed that after about 20 minutes 80% of the fall was dissolved, and after 30 minutes, all of the capsule filling was dissolved.

Comparative Example 38

33.8 g of medium chain partial glycerides, 6.3 g of polysorbate 80, and 3.8 g of Povidone K 30 were mixed to obtain a clear pale yellow solution. The mixture forms a grey emulsion when mixed with water. Upon boiling, no frothing is observed.

Comparative Example 39

33.8 g of medium chain partial glycerides, 6.3 g of polysorbate 20, and 3.8 g of Povidone K 30 were mixed to obtain a clear pale yellow solution. The mixture forms a grey translucent emulsion when mixed with water. Upon boiling, no frothing is observed.

Comparative Example 40

33.8 g of medium chain partial glycerides, 6.3 g of polyoxyl 40 hydrogenated Castor oil, and 3.8 g of Povidone K 30 were mixed to obtain a clear pale yellow solution. The mixture forms a white emulsion when mixed with water. Upon boiling, no frothing is observed.

Comparative Example 41

25.0 g of medium chain partial glycerides, 18.0 g of polysorbate 80, and 18.0 g of propylene glycol were mixed to obtain a clear pale yellow solution. The mixture forms a white emulsion when mixed with water. Upon boiling, no frothing is observed. The milky emulsion can be drawn up into the syringe.

Comparative Example 42

25.0 g of medium chain partial glycerides, 18.0 g of polysorbate 20, and 18.0 g of propylene glycol were mixed to obtain a clear pale yellow solution. The mixture forms a white emulsion when mixed with water. Upon boiling, no frothing is observed.

Comparative Example 43

25.0 g of medium chain partial glycerides, 6.3 g of polysorbate 20, and 3.8 g of Povidone K 30 were mixed to obtain a clear pale yellow solution. The mixture forms a grey translucent emulsion when mixed with water. Upon boiling no frothing is observed.

Comparative Example 44

35.0 g of medium chain partial glycerides and 15.0 g of lipoid PPL-600 were mixed to obtain a clear reddish brown solution. When mixed with water, the mixture spreads, but does not form an emulsion. Upon boiling, frothing is observed, but it does not persist. The milky emulsion can be drawn up into the syringe.

Comparative Example 45

25.0 g of medium chain partial glycerides, 15.0 g of lipoid PPL-600, and 10.0 g of propylene glycol were mixed to obtain a clean reddish brown solution. When mixed with water, the mixture spreads, but does not form an emulsion. Upon boiling, frothing is observed, but it does not persist. The milky emulsion can be drawn up into the syringe.

Comparative Example 46

20.0 g of medium chain partial glycerides, 10.0 g of lipoid PPL-600, and 20.0 g of propylene glycol were mixed to obtain a clear reddish brown solution. When mixed with water, the mixture spreads, but does not form an emulsion. Upon boiling, frothing is observed, but it does not persist. The milky emulsion can be drawn up into the syringe.

Comparative Example 47

25.0 g of lipoid PPL-600, and 25.0 g of macrogol 600 were mixed to obtain a mixture that separates and solids appear within one day of storage.

Comparative Example 48

25.0 g of lipoid PPL-600, and 25.0 g of macrogol 400 were mixed to obtain a mixture that separates alter one day of storage.

Comparative Example 49

25.0 g of lipoid PPL-600, and 25.0 g of propylene glycol were mixed to obtain a mixture that separates and solids appear within one day of storage.

Comparative Example 50

10.0 g of lipoid PPL-600, 10.0 g of macrogol 600, and 5.0 g of medium chain partial glycerides were mixed to obtain a mixture that separates.

Comparative Example 51

10.0 g of lipoid PPL-600, 10.0 g of macrogol 400, and 5.0 g of medium chain partial glycerides were mixed to obtain a mixture that separates.

Comparative Example 52

10.0 g of lipoid PPL-600, 10.0 g of propylene glycol, and 5.0 g of medium chain partial glycerides were mixed to obtain a clear reddish brown solution. When mixed with water, a yellowish emulsion forms. Upon boiling, frothing is observed, but it does not persist. The milky emulsion can be drawn up into the syringe.

Comparative Example 53

12.5 g of lipoid PPL-600, 18.8 g of polysorbate 80, and 18.8 g of propylene glycol were mixed to obtain a clear reddish brown solution. When mixed with water the mixture turns turbid. Upon boiling, little frothing is observed. The turbid emulsion can be drawn up into the syringe.

Comparative Example 54

25.0 g of lipoid PPL-600, 12.5 g of polysorbate 80, and 12.5 g of propylene glycol were mixed to obtain a clear yellow-brown solution. When mixed with water a white emulsion forms. Upon boiling, little frothing is observed, and the foam does not persist. The milky emulsion can be drawn up into the syringe.

Inventive Example 55

37.5 g of lipoid PPL-600, 6.3 g of polysorbate 80, and 6.3 g of propylene glycol were mixed to obtain a clean reddish-brown solution. When mixed with water a white emulsion forms. Upon boiling, frothing is observed, and the foam partially persists. It is very difficult to draw up the milky emulsion into the syringe.

Inventive Example 56

20.0 g of Phosal 50 PG and 2.0 g of polysorbate 80 were mixed to obtain a clear yellow solution. A yellowish emulsion forms when mixed with water, partially forming a gel. Upon boiling, frothing is observed, and the foam partially persists. Although it is possible to draw the frothy milky emulsion obtained after boiling into the syringe, for the higher concentration, very strong frothing is observed, and the milky emulsion cannot be drawn into the syringe. The dispersibility test showed that after about 10 to 15 minutes 100% of the capsule filling was finely dispersed.

Comparative Example 57

20.0 g of Phosal 50 PG and 2.0 g of polyoxyl 40 hydrogenated castor oil were mixed to obtain a clear yellow solution. A yellowish emulsion forms when mixed with water, partially forming a gel. Upon boiling, frothing is observed, and the foam partially persists. The resulting milky emulsion can be drawn into the syringe. The dispersibility test showed that after about 15 minutes 100% of the capsule filling was dispersed.

Comparative Example 58

20.0 g of Phosal 50 PG and 2.0 g of sorbitanmonolaurate were mixed to obtain a clear yellow solution. A yellowish emulsion forms when mixed with water, partially forming a gel. Upon boiling, frothing is observed, and the foam partially persists. The resulting milky emulsion can be drawn into the syringe. The dispersibility test showed that after about 15 minutes 100% of the capsule filling was dispersed.

Inventive Example 59

20.0 g of Phosal 50 PG, 2.0 g of polysorbate 80, and 1.5 g of colloidal anhydrous silica were mixed to obtain a clear yellow solution. A yellowish emulsion forms when mixed with water, partially forming a gel. Upon boiling, frothing is observed, and the foam partially persists. It is difficult to draw the milky emulsion into the syringe.

Inventive Example 60

20.0 g of Phosal 50 PG, 2.0 g of polysorbate 80, 1.5 g of colloidal anhydrous silica, and 1.5 g of xanthan were mixed to obtain a yellow suspension. A yellowish emulsion forms when mixed with water, partially forming a gel. Upon boiling, frothing is observed, and the foam partially persists. It is difficult to draw the milky emulsion into the syringe. At the higher concentrations, the formulation separates, and the aqueous phase can be drawn into the syringe.

Inventive Example 61

9.0 g of Phosal 50 PG, 1.0 g of polysorbate 80, and 1.0 g of water were mixed to obtain a turbid yellow suspension. A yellowish emulsion forms when mixed with water, partially forming a gel. Upon boiling, frothing is observed, and the foam partially persists. Although it is possible to draw the frothy milky emulsion obtained after boiling into the syringe, for the higher concentration, very strong frothing is observed, and the milky emulsion cannot be drawn into the syringe. The dispersibility test showed that after about 20 minutes 100% of the capsule filling was finely dispersed.

Comparative Example 62

9.0 g of Phosal 50 PG, 1.0 g of polysorbate 80, 0.75 g of water, and 0.25 g of ethanol were mixed to obtain an almost clear yellow solution. A yellowish emulsion forms when mixed with water, partially forming a gel. Upon boiling, frothing is observed, and the foam partially persists. The milky emulsion can be drawn into the syringe.

Inventive Example 63

9.0 g of Phosal 50 PG, 1.0 g of polysorbate 80, 0.5 g of water, and 0.5 g of ethanol were mixed to obtain a clear yellow suspension. A yellowish emulsion forms when mixed with water, partially forming a gel. Upon boiling, frothing is observed, and the foam partially persists. Although it is possible to draw the frothy milky emulsion obtained after boiling into the syringe, for die higher concentration, very strong frothing is observed, and the milky emulsion cannot be drawn into the syringe. The dispersibility test showed that after about 10 minutes 100% of the capsule filling was finely dispersed.

Comparative Example 64

20.0 g of Phosal 50 PG, 2.0 g of sorbitanmonoloaurate, and 1.5 g of colloidal anhydrous silica were mixed to obtain an almost clean yellow suspension. A yellowish emulsion forms when mixed with water, partially forming a gel. Upon boiling, frothing is observed, and the foam partially persists. It is very difficult to draw the frothy milky emulsion into the syringe.

Comparative Example 65

20.0 g of Phosal 50 PG, 2.0 g of sorbitanmonoloaurate, and 1.5 g of colloidal anhydrous silica and 1.5 g of xanthan were mixed to obtain a yellow suspension. A yellowish emulsion forms when mixed with water, partially forming a gel. Upon boiling, frothing is observed, and the foam partially persists. It is very difficult to draw the frothy milky emulsion into the syringe.

Comparative Example 66

10.0 g of propylene glycolmonolaurate and 5.0 g of Polyoxyl 40 hydrogenated castor oil were mixed to obtain a white, turbid mixture, which separated after approximately 2 days. A flocculent emulsion forms when mixed with water. No frothing is observed upon boiling.

Comparative Example 67

10.0 g of propylene glycolmonolaurate and 5.0 g of labrafil M 2125 CS were mixed to obtain a clear yellowish solution. The solution separates when mixed with water. No frothing is observed upon boiling.

Comparative Example 68

10.0 g of propylene glycolmonolaurate and 5.0 g of polysorbate 80 were mixed to obtain a clear yellowish solution. A white emulsion forms when the solution is mixed with water. No frothing is observed upon boiling.

Comparative Example 69

10.0 g of propylene glycolmonolaurate and 5.0 g of caprylocaproylmacrogol-8-glyceride were mixed to obtain a clear colorless solution. A white emulsion forms when the solution is mixed with water. No frothing is observed upon boiling.

Comparative Example 70

10.0 g of propylene glycolmonolaurate and 5.0 g of lipoid PPL-600 were mixed to obtain a clear yellowish solution. Upon addition of water, the solution partially formed a gel and separated. No frothing is observed upon boiling.

Comparative Example 71

10.0 g of propylene glycolmonolaurate and 5.0 g of macrogol-32-glycerollarate were mixed to obtain a white solid mass.

Comparative Example 72

2.0 g of gelucire 44114 and 8.0 g of Lipoid PPL-600 were mixed to obtain a yellow-brown solid mass.

Comparative Example 73

2.0 g of gelucire 44114 and 8.0 g of Labrafil M 2125 CS were mixed to obtain a turbid, yellowish, pasty liquid that separated. Upon addition of water, a white emulsion forms. No frothing is observed upon boiling.

Comparative Example 74

2.0 g of gelucire 44114 and 8.0 g of medium chain partial glycerides were mixed to obtain a clear yellowish solution. Upon addition of water, a white emulsion forms. No frothing is observed upon boiling.

Comparative Example 75

2.0 g of gelucire 44114 and 8.0 g of macrogol 600 were mixed to obtain a white solid mass.

Comparative Example 76

2.0 g of gelucire 44/14 and 8.0 g of propylene glycolmonolaurate were mixed to obtain a white, turbid solution that separated. Upon addition of water, a white emulsion forms. No frothing is observed upon boiling.

Comparative Example 77

2.0 g of gelucire 44/14 and 8.0 g of corn oil mono-1 di-1 tri-glycerides were mixed to obtain a clear yellowish solution that solidifies after 1 to 2 days. Upon addition of water, a white emulsion forms. No frothing is observed upon boiling.

Comparative Example 78

25.0 g of polysorbate 80, 12.5 g of ethanol, and 12.5 g of propylene glycol were mixed to obtain a clear yellowish solution. Upon addition of water, a clear solution forms. Frothing is observed upon boiling, but the foam does not persist.

Comparative Example 79

5.0 g of macrogol-32-glycerollaurate, 37.5 g of polyglycerol-6-diolate, and 20.0 g of propylene glycol were mixed to obtain a mixture that separates.

Comparative Example 80

10.0 g of macrogol-32-glycerollaurate, 10.0 g of polyglycerol-6-diolate, and 20.0 g of propylene glycol were mixed to obtain a mixture that separates, and partly solidifies.

Comparative Example 81

15.0 g of macrogol-32-glycerollaurate, 5.0 g of polyglycerol-6-diolate, and 20.0 g of propylene glycol were mixed to obtain a mixture that separates, and partly solidifies.

Comparative Example 82

25.0 g of polysorbate 80 and 25.0 g of glyceryl-monocapratel-caprylate were mixed to obtain a clear yellowish solution. Upon mixing with water, a white emulsion if obtained. Little frothing is observed upon boiling.

Part b) Capsule Fillings—Liquid Excipient Blends in Combination with Tapentadol Hydrochloride Inventive Example 83

A Macrogol formulation with Amberlite IRP 64 having the following composition was prepared:

|  | mg/capsule |
|---|---|
| Macrogol 600 | 479.02 |
| Caprylocaproyl Macrogol-glycerides | 160.00 |
| Colloidal Silicon Dioxide | 45.00 |
| Glycerol anhydrous | 47.00 |
| Water, purified | 12.50 |
| Amberlite IRP 64 | 80.00 |
| Tapentadol HCl | 116.48 |
| Fill weight | 940.00 |

Density: 1.173
Volume: 12.98 minims
Capsule shape: 13 oblong
For the purpose of the specification, the unit "minims" is to be regarded as "imperial minims" (U.K.), 1 imperial minim corresponding to about 59.19 µl.
Visual homogeneity up to 7 days storage:
The white homogeneous fill suspension was stable and proper flowable directly after preparation up to 7 days storage. After 2 days up to 7 day storage a slight sedimentation was observed. After homogenization the fill suspension was good flowable and homogenous. Based on these properties of the fill we decided to use the 30 l stirrable machine container as transfer vessel for manufacture of the pilot batch in order to enable continuous stirring before and during the encapsulation process.
Flowability:
Strength 10 s to 19 s: 1.01 (Claim: 0.1-2.0). The data prove the food flowability of the fill mass.

Viscosity at 25° C.:

The viscosity of the Amberlite formulation after 1 day (1001 mPas) and 7 days (1679 mPas) comply with the requirements (750-2000 mPas). No increase of viscosity at storage of the fill was observed. The results prove the suitability of the fill for encapsulation. Possible interactions with the shell were tested with manufacture of a placebo batch.

The properties of the capsules were further investigated:
Within manufacturing process of the capsules, the following parameters were tested.
  Determination of IPC fill weight at the encapsulation step
  Drying profile with overdrying for 7 days
  Migration profile of Glycerol during manufacturing, drying and overdrying
The dried capsules were tested regarding the following parameters:
  Appearance
  Seam thickness
  Fill and shell weight
  Mechanical stability
  Disintegration
  Capsule dimensions.
Results of investigation on dried capsules:

a) Appearance: The specification of a light pink 13 oblong capsule containing a white fill suspension was met.

b) Viscosity of the Jill: The viscosity of the fill mass after preparation of the fill mass was 705 mPas. It is slightly lower than the data of the fill lab sample (840 mPas).Nevertheless the data comply with the specification (500-2000 mPas) and prove the suitability for encapsulation.

c) Seam thickness: Average seam thickness of the lower and upper seams ($^{12}/_{1000}$ inch upper seam, $^{14}/_{1000}$ inch lower seam) are above the specified limits (min. $^{4}/_{1000}$ inch).

d) Fill and shell weight: Total fill and shell weight of 20 dried capsules was determined. The standard deviation for the fill is 3.8% for the shell 5.7%. Due to migration of water and Glycerol from fill to shell, the average capsule fill weight 1033.7 mg is about 8,8% (corresponding to 83.7 mg) above the nominal fill weigh 950 mg. The shell weight is within the specified limits documented in the Formula Certificate (average 405.6 mg/363.9-427.2 mg). This phenomenon is typical for Macrogol formulations.

e) Disintegration and dispersibility
Disintegration in water at 37° C.: After 3 minutes all 6 capsules were open, after 6 minutes the shell was disintegrated and finally after 15 minutes completely dissolved. The fill was fine dispersed in the disintegration medium.

Dispersibility: The dispersibility of the fill was tested in the Paddle dissolution apparatus at 100 rpm (test medium: 0.1N HCl) within performance of the dissolution profile. After 5-10 minutes the capsule shell was opened, after 20 minutes the fill was dissolved. After 45 minutes only small particles remain in the turbid dissolution medium.

f) Capsule dimensions: The dimensions of 50 dried capsules were determined. The following results were obtained:
  length: min. 20.45 mm, max. 20.89 mm, mean value: 20.71 mm
  diameter: min. 9.96 mm, max. 10.06 mm, mean value: 9.94 mm After 6 weeks storage at 30° C. and 40° C. all capsules were intact and the seam quality corresponded to the requirements. Due to decrease of hardness at 40° C. the capsules tended to stick slightly together. After 2 weeks at 40° C., the hardness decreased about 3-4 N/20 sec., which is typical for soft gelatin capsules at this storage temperature. Up to 6 weeks an increase of the hardness about 1-1.5 N/20 sec. was observed. This increase of the hardness is due to migration of Glycerol from the shell into the fill.

Inventive Example 84

A Macrogol formulation with Xanthan having the following composition was prepared:

|  | mg/capsule |
| --- | --- |
| Macrogol 600 Ph. Eur. NF | 554.020 |
| Caprylocaproyl Macrogolglyceride | 175.000 |
| Colloidal anhydrous Silica | 40.000 |
| Glycerol Ph. Eur., USP | 47.000 |
| Purified water Ph. Eur., USP | 12.500 |
| Xanthan Ph. Eur. | 5.000 |
| Tapentadol HCl | 116.480 |
| Fill weight | 950.000 |

Density: 1.152
Volume: 13.36 minims
Capsule shape: 13 oblong
Visual homogeneity up to 7 days storage:
The white suspension was homogeneous and flowable after preparation. After 1, 2 and 7 days storage a slight sedimentation was observed. After stirring and re-homogenization a homogeneous and flowable fill suspension was resulting. This fill suspension should be stored under stirring until starting of encapsulation process. If this is not possible a rehomogenization is necessary. The fill will be stirred during the encapsulation process too (routinely for all fill suspensions).

Flowability:
Strength after 10 s to 19 s: 2.72. The data comply with the specification and prove the food flowability.

Viscosity:
The viscosity decreases slightly from 840 mPas after 1 day to 793.9 mPas after 7 days storage. All results are within the specified limits (500-2000 mPas). The data prove the physical stability and suitability of the fill formulation for the encapsulation process.

The properties of the capsules were further investigated:
Within manufacturing process of the capsules, the following parameters were tested.
  Determination of IPC fill weight at the encapsulation step
  Drying profile with overdrying for 7 days
  Migration profile of Glycerol during manufacturing, drying and overdrying
The dried capsules were tested regarding the following parameters:
  Appearance
  Seam thickness
  Fill and shell weight
  Mechanical stability
  Disintegration
  Capsule dimensions.

Within the temperature challenge test the capsules were stored for 6 weeks at 30° C. and 40° C. with testing of appearance, hardness and stickiness for every 2 weeks. Additionally glycerol content of fill and shell will be tested after 6 weeks storage.

Results of investigations on dried capsules:
a) Appearance: The specification of 13 oblong capsules with a pink capsule shell containing a white fill suspension was met.

b) Viscosity of the fill: The viscosity of the fill mass after preparation of the fill mass was 1384 mPas. The viscosity complies with the viscosity of the fill of Pseudoephedrin Capsules, but is slightly lower than the data of the fill lab sample (1601 mPas). Nevertheless the data comply with the specification (500-2000 mPas) that is suitable for encapsulation.

c) Seam thickness: The seam thickness (13/1000 inch for upper seam, 14/1000 inch for lower seam) of the dried capsules is widely above the specified limits (min. 4/1000 inch) and prove the physical stability of the selected formulation.

d) Fill and shell weight: Total fill and shell weight of 20 dried capsules were determined. The standard deviation of fill weight of 6.4% of shell weight is 7.2% The shell weight complies weight the shell weight documented in the Formula Certificate. The average fill weight (1025.6 mg) is increased about 9.1% due to migration of water from fill to shell (release with water content 8.2%).

e) Disintegration and dispersibility of the fill

Disintegration: The capsules were open within 3 minutes, after 6 minutes the shell was disintegrated and dissolved after 5 minutes with fine dispersion of the fill. The fill dispersibility was additionally tested with the dissolution profile.

Dispersibility: The dispersibility of the fill was tested in the Paddle dissolution apparatus at 100 rpm (test medium: 0.1N HCl) within performance of the dissolution profile. After 5-10 minutes the capsule shell was opened, after 20 minutes the fill was dissolved. After 45 minutes only small particles remain in the turbid dissolution medium.

f) Capsule dimensions: The dimensions of 50 dried capsules were determined. The following results were obtained:

length: min. 20.22 mm, max. 20.58 mm, mean value: 20.43 mm diameter: min. 9.86 mm, max. 10.02 mm, mean value: 9.93 mm After 6 weeks storage at 30° C. and 40° C. all capsules were intact and the seam quality corresponded to the requirements. Due to decrease of hardness at 40° C. the capsules tended to stick slightly together. After 2 weeks at 40° C., the hardness decreased about 3-4 N/20 sec., which is typical for soft gelatin capsules at this storage temperature. Up to 6 weeks an increase of the hardness about 1-1.5 N/20 sec. was observed. This increase of the hardness is due to migration of Glycerol from the shell into the fill. This effect is observed too at 30° C. storage. After initial decrease (2 weeks) of hardness about 1-1.5 N/20 sec., the hardness increases in the same range up to 6 weeks storage. This phenomenon is typical for soft gelatin capsules containing amphiphilic or hydrophilic fill masses based on Macrogol.

The results prove the physical stability of the formulation.

Results of dissolution profile and syringability testing: The two critical parameters to evaluate the success of the formulation development and manufacture of both pilot batches of Tapentadol 100 mg capsules are:

immediate release dissolution
>80% after 30 minutes
dissolution profile in 0.1 NHCl comparable with Tapentadol 100 mg tablets syringability (TRF test):
not more than 33% detectable in syringe after boiling of the capsule fill with 5 ml water in order to meet the requirements on abuse resistance of the formulation

|  | Dissolution rate after 30 minutes, 75 rpm, 0.1N HCl | Syringability |
| --- | --- | --- |
| Inventive Example 83 | 104.5% (n = 6, RSD = 1.9%) | 6.8% (n = 6) (7.8; 3.8; 1.9; 5.2; 11.0; 10.9%) |
| Inventive Example 84 | 103.1% (n = 6, RSD = 1.3%) | 3.9% (n = 6) (5.9; 1.6; 3.7; 2.6; 1.1; 8.7%) |

Therefore both capsules fully comply with the requirements and objectives for development and of an immediate release abuse resistant softgel formulation.

The remaining residue of the fill mass after boiling in the syringe with water was maximum 1 ml.

The specified minimum 80% Tapentadol HCl were released from the amphiphilic fill suspension after 15 minutes. After 25 minutes 100% of the active substance were detected in the dissolution medium.

The invention claimed is:

1. A tamper resistant pharmaceutical capsule comprising a capsule filling and a capsule shell, wherein said capsule filling is encapsulated by said capsule shell and comprises:
   (a) Tapentadol or a physiologically acceptable salt thereof in an amount within the range of from 10 mg to 400 mg, as equivalent weight relative to Tapentadol free base; and
   (b) a liquid excipient blend comprising a solvent, a surfactant, and a viscosity enhancer;
   wherein the viscosity enhancer comprises colloidal anhydrous silica and a gum;
   wherein a mixture of 250 milligrams of the liquid excipient blend with 5 milliliters of water at the mixture's boiling point forms a viscous phase which cannot pass through a 25 millimeter long needle having an inner diameter of 0.60 millimeters; and
   wherein the capsule provides immediate release of Tapentadol or the physiologically acceptable salt thereof upon oral administration.

2. The capsule according to claim 1, wherein the gum is selected from the group consisting of acacia, agar, tragacanth, guar gum, xanthan gum, locust bean gum, tara gum, karaya, gellan gum, welan gum, and rhamsan gum.

3. The capsule according to claim 1, wherein the total content of viscosity enhancer is within the range of from 0.1 to 10 wt.-%, relative to the total weight of the capsule filling.

4. The capsule according to claim 1, wherein the total content of solvent is within the range of from 10 to 90 wt.-%, relative to the total weight of the capsule filling.

5. The capsule according to claim 1, wherein the liquid excipient blend comprises an ion exchange resin.

6. The capsule according to claim 5, wherein the ion exchange resin is anionic.

7. The capsule according to claim 5, wherein the total content of ion exchange resin is within the range of from 0.1 to 25 wt.-%, relative to the total weight of the capsule filling.

8. The capsule according to claim 1, wherein the surfactant is nonionic.

9. The capsule according to claim 8, wherein the nonionic surfactant is selected from the group consisting of glycerol monoesters with $C_{6-18}$-fatty acids, glycerol diesters with identical or different $C_{6-18}$-fatty acids, glycerol triesters with identical or different $C_{6-18}$-fatty acids, polyethylene glycol monoesters with $C_{6-18}$-fatty acids, polyethylene glycol diesters with identical or different $C_{6-18}$-fatty acids, and mixtures of any of the foregoing.

10. The capsule according to claim 1, wherein the total content of surfactant is within the range of from 0.1 to 35 wt.-%, relative to the total weight of the capsule filling.

11. The capsule according to claim 1, wherein the total content of Tapentadol or physiologically acceptable salt thereof, as equivalent weight relative to Tapentadol free base, is within the range of from 0.1 to 25 wt.-%, relative to the total weight of the capsule filling.

12. A method for treating pain in a patient in need of such treatment, said method comprising administering to said patient at least one capsule according to claim 1.

13. A method for preventing parenteral abuse of Tapentadol or a physiologically acceptable salt thereof, said method comprising providing the Tapentadol or a physiologically acceptable salt thereof in the form of a capsule according to claim 1.

* * * * *